US012729204B2

(12) United States Patent
Li et al.

(10) Patent No.: US 12,729,204 B2
(45) Date of Patent: Sep. 8, 2026

(54) TRPC5 INHIBITOR COMPOUNDS AND INTERMEDIATE THEREOF, PREPARATION METHOD THEREFOR AND USE THEREOF

(71) Applicant: WUHAN LL SCIENCE AND TECHNOLOGY DEVELOPMENT CO., LTD., Wuhan (CN)

(72) Inventors: Jinping Li, Wuhan (CN); Jun Lou, Wuhan (CN); Zhanying Wang, Wuhan (CN); Li Liu, Wuhan (CN); Xiaodan Guo, Wuhan (CN); Feng Zhou, Wuhan (CN); Yihan Zhang, Wuhan (CN); Yongkai Chen, Wuhan (CN); Chaodong Wang, Wuhan (CN)

(73) Assignee: WUHAN LL SCIENCE AND TECHNOLOGY DEVELOPMENT CO., LTD., Wuhan (CN)

( * ) Notice: Subject to any disclaimer, the term of this patent is extended or adjusted under 35 U.S.C. 154(b) by 464 days.

(21) Appl. No.: 18/274,727

(22) PCT Filed: Jan. 28, 2022

(86) PCT No.: PCT/CN2022/074649

§ 371 (c)(1),
(2) Date: Jul. 28, 2023

(87) PCT Pub. No.: WO2022/166817

PCT Pub. Date: Aug. 11, 2022

(65) Prior Publication Data

US 2024/0317755 A1 Sep. 26, 2024

(30) Foreign Application Priority Data

Feb. 7, 2021 (CN) ........................ 202110169176.X
Jan. 19, 2022 (CN) ......................... 202210062324.2

(51) Int. Cl.

*C07D 487/04* (2006.01)
*A61K 31/501* (2006.01)
*C07F 9/6561* (2006.01)

(52) U.S. Cl.

CPC .......... *C07D 487/04* (2013.01); *A61K 31/501* (2013.01); *C07F 9/6561* (2013.01)

(58) Field of Classification Search

CPC ... A61K 31/501; C07D 487/04; C07F 9/6561; A61P 13/12; A61P 25/00; A61P 21/00; A61P 35/00; A61P 25/08; A61P 25/18; A61P 25/16; A61P 25/22; A61P 25/28
See application file for complete search history.

(56) References Cited

U.S. PATENT DOCUMENTS

2023/0257382 A1 8/2023 Li et al.

FOREIGN PATENT DOCUMENTS

| | | | |
|---|---|---|---|
| CN | 113880843 | A | 1/2022 |
| EP | 4470540 | A1 | 12/2024 |
| TW | 202202505 | A | 1/2022 |
| WO | 2019055966 | A2 | 3/2019 |
| WO | 2019212937 | A1 | 11/2019 |
| WO | 2020061162 | A1 | 3/2020 |
| WO | 2023143316 | A1 | 8/2023 |

OTHER PUBLICATIONS

Dec. 15, 2023 First Office Action issued in Australian Patent Application No. 2022216707.
Jan. 30, 2024 First Office Action issued in Chinese Patent Application No. 202210107183.1.
Jan. 29, 2024 Search Report issued in Chinese Patent Application No. 202210107183.1.
Apr. 26, 2022 International Search Report issued in International Patent Application No. PCT/CN2022/074649.
Apr. 26, 2022 Written Opinion of the International Searching Authority issued in International Patent Application No. PCT/CN2022/074649.
Mar. 27, 2023 First Office Action issued in Taiwanese Patent Application No. 111104050.
Berge et al., Pharmaceutical Salts, Journal of Pharmaceutical Sciences, vol. 66, pp. 1-19, 1977.
P. Heinrich Stahl and Camille G. Wermuth, Handbook of Pharmaceutical Salts: Properties, Selection, and Use, Wiley-VCH, 2002.
Raymond C Rowe et al., Handbook of Pharmaceutical Excipients, Sixth Edition, 2009.
Shang-Zhong Xu et al., TRPC channel activation by extracellular thioredoxin, Nature 451 (7174): 69-72, 2008.

(Continued)

*Primary Examiner* — Sarah Pihonak
*Assistant Examiner* — Padmaja S Rao

(57) ABSTRACT

Disclosed are a heterocyclic compound, and an intermediate thereof, a preparation method therefor and the use thereof. Namely, provided are a heterocyclic compound as shown in formula I-a, and a tautomer and a pharmaceutically acceptable salt thereof, wherein the compound has a good water solubility and pharmacokinetic properties.

I-a

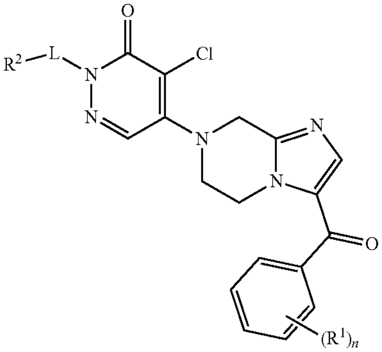

22 Claims, 1 Drawing Sheet

(56) References Cited

OTHER PUBLICATIONS

Michael Dattilo et al., Inhibition of TRPC5 Channels by Intracellular ATP, Mol Pharmacol. 73 (1): 42-49, 2008.
Marcus Semtner et al., Potentiation of TRPC5 by Protons, J Bio Chem. 282 (46): 33868-33878, 2007.
Min Ji Kim et al., Molecular determinant of sensing extracellular PH in classical transient receptor potential channel 5, Biochem and Biophys Res Commun. 365 (2): 239-245, 2008.
Erik W. Bush et al., Canonical Transient Receptor Potential Channels Promote Cardiomyocyte Hypertrophy through Activation of Calcineurin Signaling, J Biol Chem. 281 (44): 33487-33496, 2006.
Junko Yoshida et al., Capacitative Ca2+ entries and mRNA expression for TRPC1 and TRPC5 channels in human epidermoid carcinoma A431 cells, Eur J Pharmacol. 510 (3): 217-222, 2005.
Philippa K. Flemming et al., Sensing of Lysophospholipids by TRPC5 Calcium Channel, J Biol Chem. 281 (8): 4977-4982, 2006.
D. J. Beech, Bipolar phospholipid sensing by TRPC5 calcium channel, Biochem Soc Trans. 35 (Pt 1): 101-104, 2007.
D. J. Beech, Canonical Transient Receptor Potential 5, Handb Exp Pharmacol. 179: 109-123, 2007.
Li-Ping He et al., A Functional Link between Store-operated and TRPC Channels Revealed by the 3,5-Bis (trifluoromethyl)pyrazole Derivative, BTP2, J Biol Chem. 280 (12): 10997-11006, 2005.
Shunichi Shimizu et al., Ca2+-calmodulin-dependent myosin light chain kinase is essential for activation of TRPC5 channels expressed in HEK293 cells, J Physiol. 570 (Pt 2): 219-235, 2006.
Anna Greka et al., TRPC5 is a regulator of hippocampal neurite length and growth cone morphology, Nat Neurosci. 6: 837-845, 2003.
Dec. 19, 2024 The extended European search report issued in the counterpart European application No. 22749096.8.

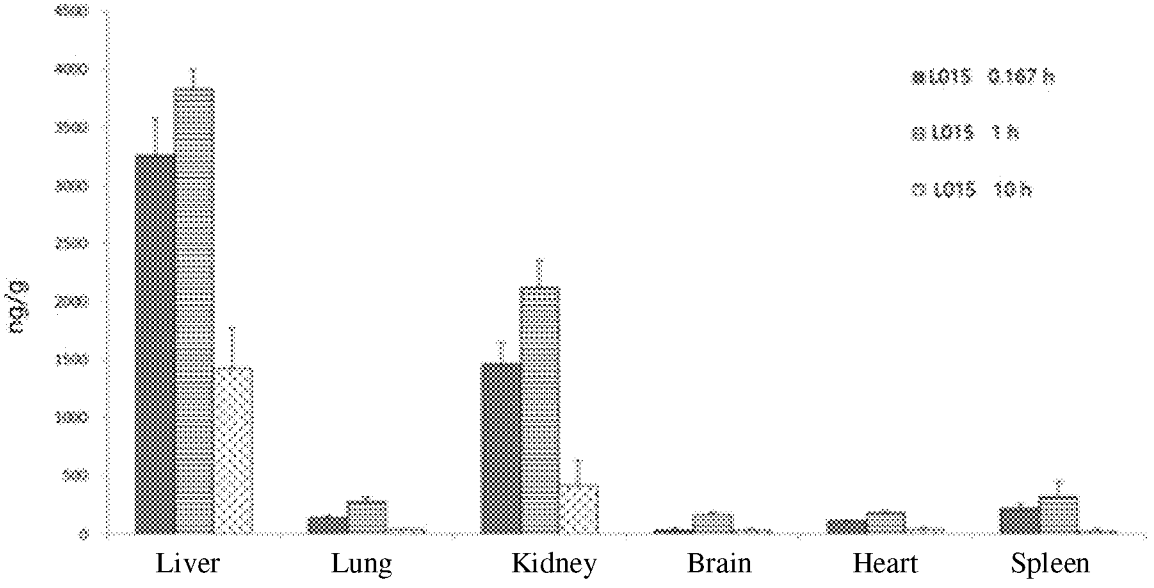
L015 0.167 h
L015 1 h
L015 10 h
ng/g
Liver
Lung
Kidney
Brain
Heart
Spleen

TRPC5 INHIBITOR COMPOUNDS AND INTERMEDIATE THEREOF, PREPARATION METHOD THEREFOR AND USE THEREOF

The present application is a National Stage of International Application No. PCT/CN2022/074649, filed on Jan. 28, 2022, which claims the right of the priorities of Chinese patent application 202110169176X filed on Feb. 7, 2021, and Chinese patent application 2022100623242 filed on Jan. 19, 2022. The contents of the above Chinese patent application are incorporated herein by reference in its entirety.

TECHNICAL FIELD

The present disclosure relates to TRPC5 inhibitor compounds and intermediate thereof, preparation method therefor and use thereof.

BACKGROUND

A variety of ion channel proteins exist to regulate the flow of ions through cell membranes. The proper expression and function of ion channel proteins are important for the maintenance of cell function and intracellular communication. Many diseases are caused by abnormal regulation of membrane potential or abnormal calcium handling. Considering the central importance of ion channels in the regulation of membrane potential and ion flow in cells, the identification of agents that can promote or inhibit specific ion channels is of great interest as research tools and as possible therapeutic agents.

TRPC (Transient receptor potential canonical) is one of the most important subfamilies in the TRP superfamily, including TRPC1-7, wherein TRPC2 is a pseudogene and is not expressed in humans. According to the homology and structural characteristics of amino acid sequences, TRPCs can be divided into two subclasses: TRPC1, 4, 5 are classified into one subclass, and TRPC3, 6, 7 are classified into one subclass. According to the activation mode, functional TRPC can be divided into store-operated calcium channel and receptor-operated calcium channel. TRPC channels activated by both modes behave as nonspecific cation channels, which can mediate sodium and calcium influx and potassium efflux.

Cation channels (such as transient receptor potential (TRP) cation channel subfamily C, member 5 (TRPC5)) regulate the flow of calcium and sodium ions through cell membranes. The influx of sodium and calcium leads to depolarization of cells. This increases the likelihood that voltage-gated ion channels will reach the threshold required for activation. Thus, activation of non-selective cation channels can increase electrical excitability and increase the frequency of voltage-dependent events. Voltage-dependent events include, but are not limited to, neuronal action potentials, cardiac action potentials, smooth muscle contractions, cardiac muscle contractions, and skeletal muscle contractions.

Calcium influx caused by activation of non-selective cation channels (such as TRPC5) also alters intracellular free calcium concentration. Calcium is a ubiquitous second messenger molecule in cells, and the change in intracellular calcium level has a profound effect on signal transduction and gene expression. Therefore, activation of non-selective cation channels (such as TRPC5) can lead to changes in gene expression and cell phenotype. Gene expression events include, but are not limited to, the production of mRNA encoding cell surface receptors, ion channels, and kinases. These changes in gene expression can lead to the hyperexcitability in this cell.

Homomeric TRPC5 ion channels are signal transduction gated, $Ca^{2+}$-permeable channels predominantly expressed in the neurons. TRPC5 forms homomultimeric structures (such as tetramers (i.e., TRPC5 homomultimers)) and heteromultimeric structures (such as tetramers (i.e., TRPC5-TRPC1 heteromultimers)). Unless otherwise specified, when the term TRPC5 is used herein (for example, when identifying a modulator of TRPC5 such as a TRPC5 antagonist), the term TRPC5 is used generically so as to include either or both of a TRPC5 homomultimer or a heteromultimer (such as TRPC5-TPRC1 or TRPC5-TRPC4 heteromultimer). Examples of TRPC5 in the literature include the following: Nature. Jan. 3, 2008; 451(7174): 69-72; Mol Pharmacol. January 2008; 73(1): 42-9; J Biol Chem. Nov. 16, 2007; 282(46): 33868-78; Biochem Biophys Res Commun. Jan. 11, 2008; 365(2): 239-45; J Biol Chem. Nov. 3, 2006; 281(44): 33487-96; Eur J Pharmacol. Mar. 14, 2005; 510(3): 217-22; J Biol Chem. Feb. 24, 2006; 281(8): 4977-82; Biochem Soc Trans. February 2007; 35 (Pt 1): 101-4; Handb Exp Pharmacol. 2007; (179): 109-23; J Biol Chem. Mar. 25, 2005; 280(12): 10997-1006; J Physiol. Jan. 15, 2006; 570 (Pt 2): 219-35; and Nat Neurosci. (2003) 6: 837-45.

Modulating the function of the TRPC5 protein provides a method for modulating calcium homeostasis, sodium homeostasis, membrane polarization, and/or intracellular calcium levels, and compounds that can modulate TRPC5 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis.

Compounds that inhibit TRPC5 containing ion channels are, for example, suitable for treating diseases by modulating the activity of transient receptor potential cation channel subfamily C, member 5 (TRPC5) which can be in the form of homomultimer and heteropolymer with other ion channels (such as TRPC1 or TRPC3), i.e., TRPC5-TRPC1 and TRPC1-TRPC3-TRPC5.

Focal segmental glomerulosclerosis (FSGS) is a clinicopathological syndrome, clinically manifested as massive proteinuria or nephrotic syndrome, and it is pathologically characterized by foot process fusion or disappearance caused by focal segmental distribution of glomerulosclerosis lesions and podocyte degeneration. FSGS accounts for about 5% to 10% of adult nephrotic syndrome in China, and patients are more common in young adult males. 50% or more of patients with persistent nephrotic syndrome progress to end-stage nephropathy within 5 to 10 years.

In healthy glomeruli, TRPC5 is isolated in cytoplasm, maintaining normal filtration barrier, and when podocytes are injured, podocyte injury activates RAC1, causing TRPC5 to transfer from cytoplasm to cell membrane, which promotes the influx of calcium ions through TRPC5 channel induced by AT1 receptor, and further promotes RAC1 activity, and RAC1 activation induces actin recombination and podocyte detachment from glomerulus; the loss of podocytes breaks the filter barrier, causing the serum protein to leak into the urine.

Currently, the clinically used FSGS therapeutic drugs are mainly hormones, immunosuppressants, CNIs, and alkylating agents, all of which have serious toxic and side effects, and many of them need to be used in combination with other drugs to be effective and are prone to relapse.

CONTENT OF THE PRESENT INVENTION

The present disclosure aims to solve the problems of poor solubility and low bioavailability of existing TRPC5 inhibitor compounds. Therefore, the present disclosure provides TRPC5 inhibitor compounds and intermediate thereof, preparation method therefor and use thereof. The compounds of the present disclosure have better water solubility and pharmacokinetic properties.

The present disclosure provides a compound represented by formula I-a, a tautomer thereof, a pharmaceutically acceptable salt thereof, a solvate thereof, or a solvate of the pharmaceutically acceptable salt thereof;

I-a

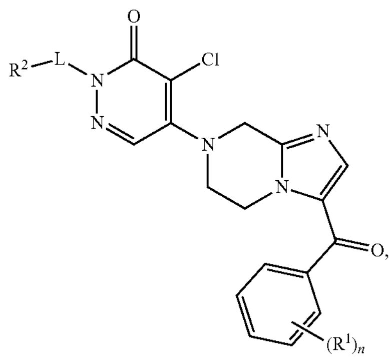

wherein n is 0, 1, 2, 3, or 4;

$R^1$ is independently —CN, halogen, —OH, $C_1$-$C_4$ alkyl, or $C_1$-$C_4$ alkyl substituted by 1, 2, 3, or 4 $R^{1-1}$ groups;

$R^{1-1}$ is independently —CN, halogen, or —OH;

L is a single bond or —$CR^aR^b$—;

$R^a$ is H or $C_1$-$C_3$ alkyl;

$R^b$ is H, halogen, or $C_1$-$C_3$ alkyl;

$R^2$ is

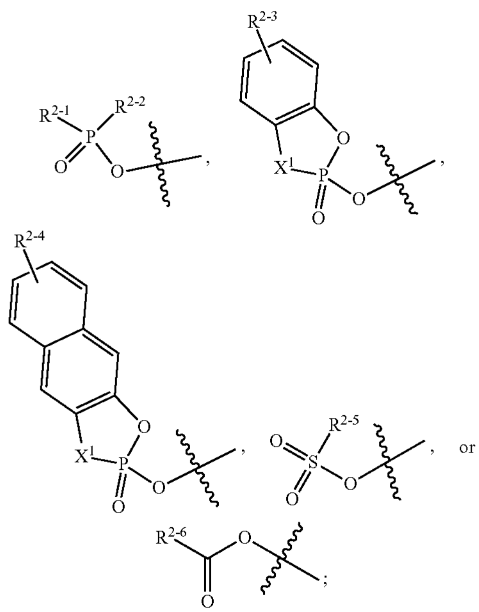

, , , or ;

$X^1$ is —O—, —S—, —NH—, —O—$CH_2$—, —S—$CH_2$—, —NH—$CH_2$—, —$CH_2$—, or —$CH_2$—$CH_2$—;

$X^2$ is —O—, —S—, —NH—, —O—$CH_2$—, —S—$CH_2$—, —NH—$CH_2$—, —$CH_2$—, or —$CH_2$—$CH_2$—;

$R^{2-1}$ and $R^{2-2}$ are independently —$OR^{2-1}$, —$SR^{2-1}$, or —$NR^{2-1-2}R^{2-1-3}$.

$R^{2-1-1}$ is independently H, $C_1$-$C_6$ alkyl, $C_3$-$C_6$ cycloalkyl, $C_1$-$C_6$ alkyl substituted by 1, 2, 3, or 4 $R^{2-1-1-1}$ groups, or $C_3$-$C_6$ cycloalkyl substituted by 1, 2, 3, or 4 $R^{2-1-1-1}$ groups;

$R^{2-1-1}$-1 is independently —CN, F, Cl, Br, I, —OH, —$NH_2$, —COOH, or —$NO_2$;

$R^{2-1-2}$ and $R^{2-1-3}$ are independently H or $C_1$-$C_6$ alkyl;

$R^{2-3}$ is H, F, Cl, Br, I, —CN, —$NO_2$, —$NH_2$, $C_1$-$C_3$ alkyl, or $C_1$-$C_3$ alkoxy;

$R^{2-4}$ is H, F, Cl, Br, I, —CN, —$NO_2$, —$NH_2$, $C_1$-$C_3$ alkyl, or $C_1$-$C_3$ alkoxy;

$R^{2-5}$ is —$OR^{2-5-1}$, —$SR^{2-5-1}$, or —$NR^{2-5-2}R^{2-5-3}$.

$R^{2-5-1}$ is independently H, $C_1$-$C_6$ alkyl, $C_3$-$C_6$ cycloalkyl, $C_1$-$C_6$ alkyl substituted by 1, 2, 3, or 4 $R^{2-5-1-1}$ groups, or $C_3$-$C_6$ cycloalkyl substituted by 1, 2, 3, or 4 $R^{2-5-1-1}$ groups;

$R^{2-5-1-1}$ is independently —CN, F, Cl, Br, I, —OH, —$NH_2$, —COOH, or —$NO_2$;

$R^{2-5-2}$ and $R^{2-5-3}$ are independently H or $C_1$-$C_6$ alkyl;

$R^{2-6}$ is $C_1$-$C_8$ alkyl, $C_3$-$C_6$ cycloalkyl, —$NR^{2-6-2}R^{2-6}$-3, $C_1$-$C_8$ alkyl substituted by 1, 2, 3, or 4 $R^{2-6-1}$ groups, or $C_3$-$C_6$ cycloalkyl substituted by 1, 2, 3, or 4 $R^{2-6-1}$ groups;

$R^{2-6-1}$ is independently —CN, F, Cl, Br, I, —OH, —$NH_2$, —COOH, or —$NO_2$;

$R^{2-6-2}$ and $R^{2-6-3}$ are independently H or $C_1$-$C_6$ alkyl.

In a certain embodiment, some groups in the compound represented by formula I-a, the tautomer thereof, the pharmaceutically acceptable salt thereof, the solvate thereof, or the solvate of the pharmaceutically acceptable salt thereof are defined as follows, and unmentioned groups in the following are as defined in any one of the above embodiments (this paragraph is hereinafter referred to as "in a certain embodiment"): n is 2.

In a certain embodiment, $R^1$ is independently halogen or $C_1$-$C_4$ alkyl substituted by 1, 2, 3, or 4 $R^{1-1}$ groups, for example, $R^1$ is independently fluorine or trifluoromethyl.

In a certain embodiment, $R^{1-1}$ is independently halogen.

In a certain embodiment, L is the single bond or —$CH_2$—.

In a certain embodiment, L is —$CR^aR^b$—, for example —$CH_2$—.

In a certain embodiment, $R^a$ is H.

In a certain embodiment, $R^b$ is H.

In a certain embodiment, $R^2$ is

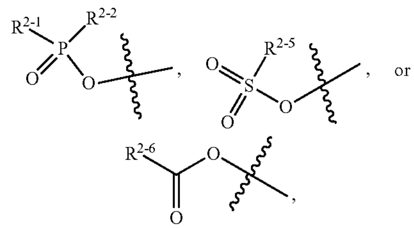

, , or , for example

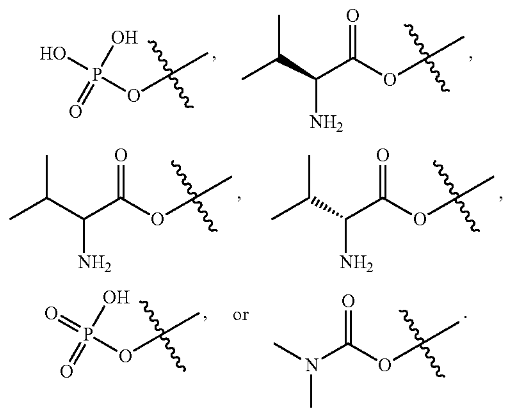

In a certain embodiment, $R^{2-1}$ and $R^{2-2}$ are independently —$OR^{2-1-1}$.

In a certain embodiment, $R^{2-1-1}$ is H.

In a certain embodiment, $R^{2-5}$ is —$OR^{2-5-1}$.

In a certain embodiment, $R^{2-5-1}$ is H.

In a certain embodiment, $R^{2-6}$ is —$NR^{2-6-2}R^{2-6-3}$ or $C_1$-$C_5$ alkyl substituted by 1, 2, 3, or 4 $R^{2-6-1}$ groups.

In a certain embodiment, $R^{2-6-1}$ is —$NH_2$.

In a certain embodiment, $R^{2-6-2}$ and $R^{2-6-3}$ are independently methyl or ethyl.

In a certain embodiment,

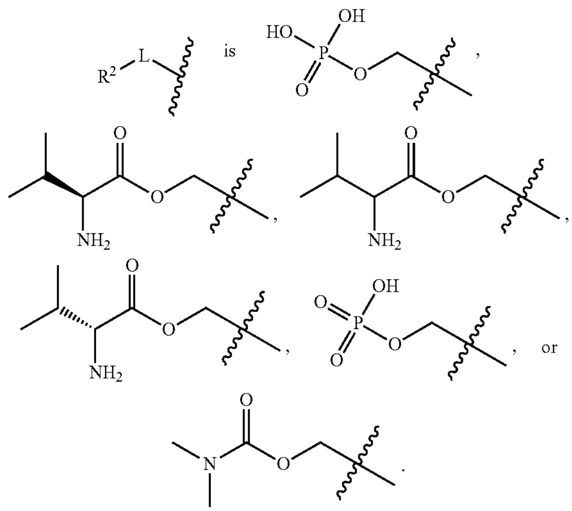

In a certain embodiment, n is 2;

$R^1$ is independently halogen or $C_1$-$C_4$ alkyl substituted by 1, 2, 3, or 4 $R^{1-1}$ groups;

$R^{1-1}$ is independently halogen;

L is —$CR^aR^b$—;

$R^a$ is H;

R is H;

$R^2$ is

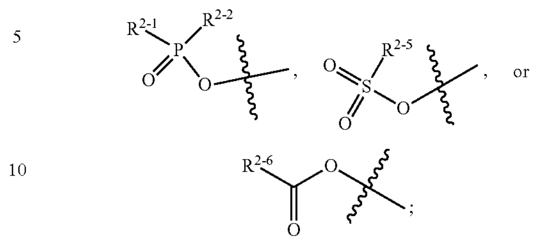

$R^{2-1}$ and $R^{2-2}$ are independently —$OR^{2-1-1}$;

$R^{2-1-1}$ is H;

$R^{2-5}$ is —$OR^{2-5-1}$;

$R^{2-5-1}$ is H;

$R^{2-6}$ is —$NR^{2-6-2}R^{2-6-3}$ or $C_1$-$C_5$ alkyl substituted by 1, 2, 3, or 4 $R^{2-6-1}$ groups;

$R^{2-6-1}$ is —$NH_2$;

$R^{2-6-2}$ and $R^{2-6-3}$ are independently methyl or ethyl.

In a certain embodiment,

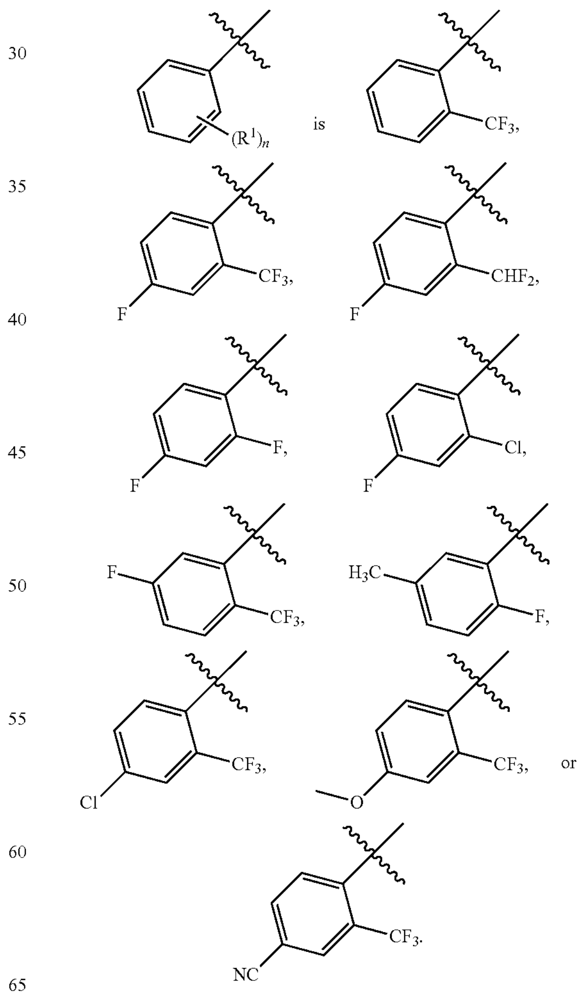

In a certain embodiment,

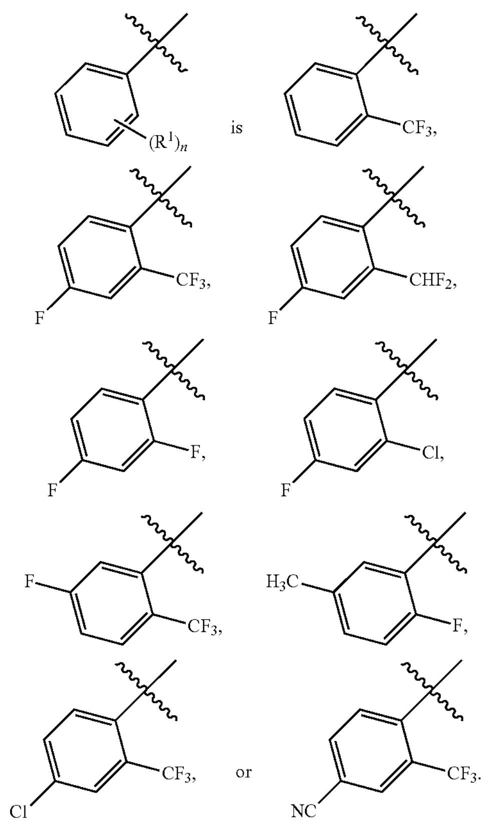

In a certain embodiment,

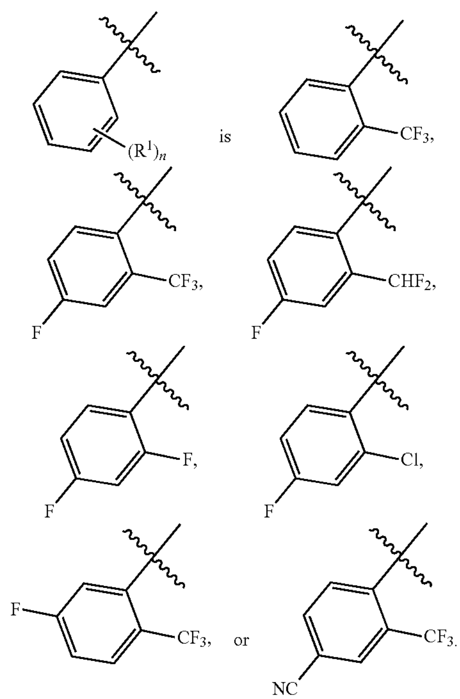

In a certain embodiment,

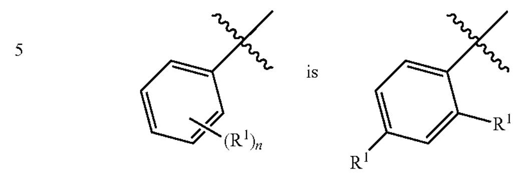

In a certain embodiment,

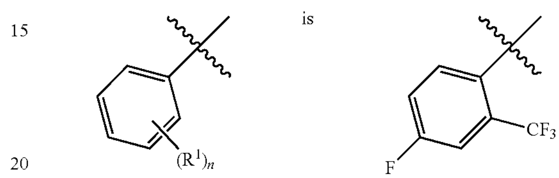

In a certain embodiment, when $R^1$ is independently halogen, the halogen is fluorine, chlorine, or bromine, for example fluorine.

In a certain embodiment, when $R^1$ is independently $C_1$-$C_4$ alkyl substituted by 1, 2, 3, or 4 $R^{1-1}$ groups, the $C_1$-$C_4$ alkyl is independently methyl, ethyl, n-propyl, isopropyl, n-butyl, isobutyl, sec-butyl, or tert-butyl, for example methyl.

In a certain embodiment, when $R^1$ is independently $C_1$-$C_4$ alkyl substituted by 1, 2, 3, or 4 $R^{1-1}$ groups, the $R^{1-1}$ is independently halogen, for example fluorine.

In a certain embodiment, when $R^1$ is independently $C_1$-$C_4$ alkyl substituted by 1, 2, 3, or 4 $R^{1-1}$ groups, the number of $R^{1-1}$ groups is 2 or 3, for example 3.

In a certain embodiment, when $R^1$ is independently $C_1$-$C_4$ alkyl substituted by 1, 2, 3, or 4 $R^{1-1}$ groups, the $C_1$-$C_4$ alkyl substituted by 1, 2, 3, or 4 $R^{1-1}$ groups is difluoromethyl or trifluoromethyl, for example trifluoromethyl.

In a certain embodiment, when $R^{2-6}$ is $C_1$-$C_8$ alkyl substituted by 1, 2, 3, or 4 $R^{2-6-1}$ groups, the $C_1$-$C_8$ alkyl is $C_1$-$C_4$ alkyl, for example isobutyl.

In a certain embodiment, when $R^{2-6}$ is $C_1$-$C_8$ alkyl substituted by 1, 2, 3, or 4 $R^{2-6-1}$ groups, the $R^{2-6-1}$ is independently —$NH_2$.

In a certain embodiment, when $R^{2-6}$ is $C_1$-$C_8$ alkyl substituted by 1, 2, 3, or 4 $R^{2-6-1}$ groups, the number of $R^{2-6-1}$ groups is 1.

In a certain embodiment, when $R^{2-6}$ is $C_1$-$C_8$ alkyl substituted by 1, 2, 3, or 4 $R^{2-6-1}$ groups, the $R^{2-6}$ is

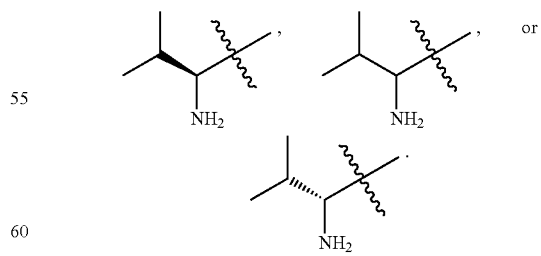

In a certain embodiment, when $R^{2-6-2}$ and $R^{2-6-3}$ are independently $C_1$-$C_6$ alkyl, the $C_1$-$C_6$ alkyl is $C_1$-$C_3$ alkyl, for example, both are methyl.

In a certain embodiment, when $R^{2-6}$ is —$NR^{2-6-2}R^{2-6-3}$, the $R^{2-6}$ is

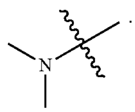 [SMILES: *N(C)C]
In a certain embodiment, the compound represented by formula I-a has a structure shown in formula I-b:
I-b
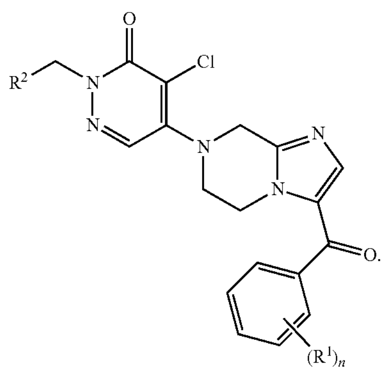
In a certain embodiment, the compound represented by formula I-a is selected from the following compounds:
1
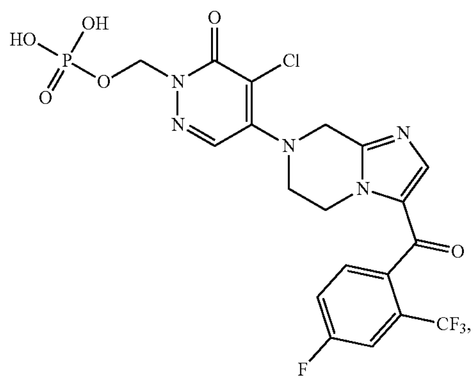
2
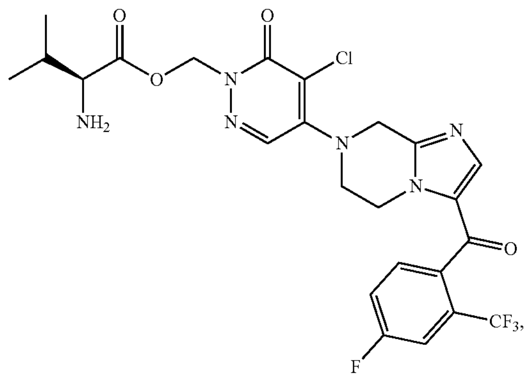
-continued
3
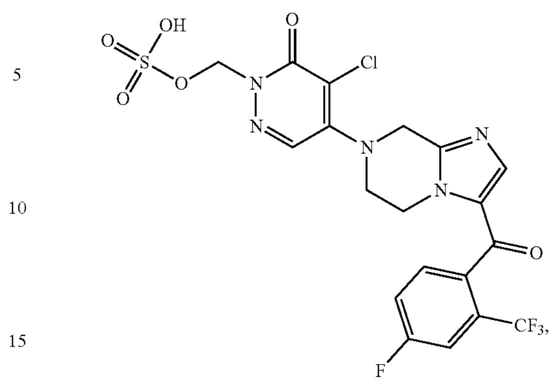
4
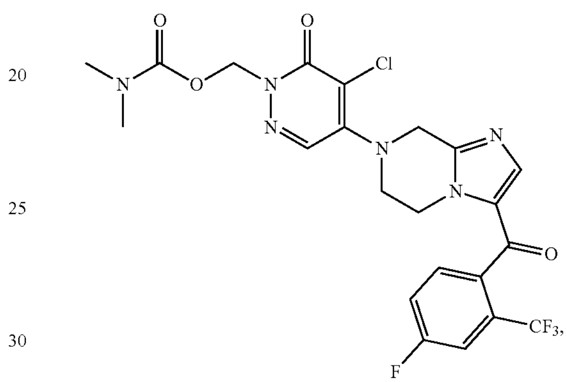
5
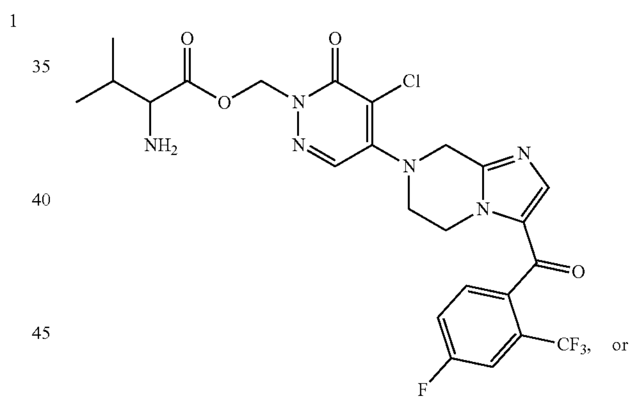
or
6
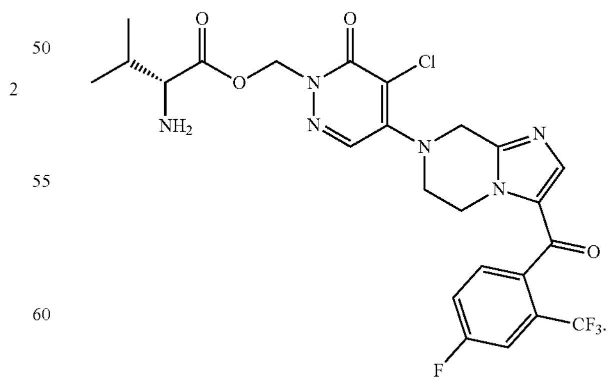
The present disclosure also provides a preparation method for the compound represented by formula I-b, which is method 1 or method 2:

the method 1 comprises the following step: in a solvent, in the presence of an acid, carrying out a deprotection reaction on compound I-c to obtain the compound represented by formula I-b;

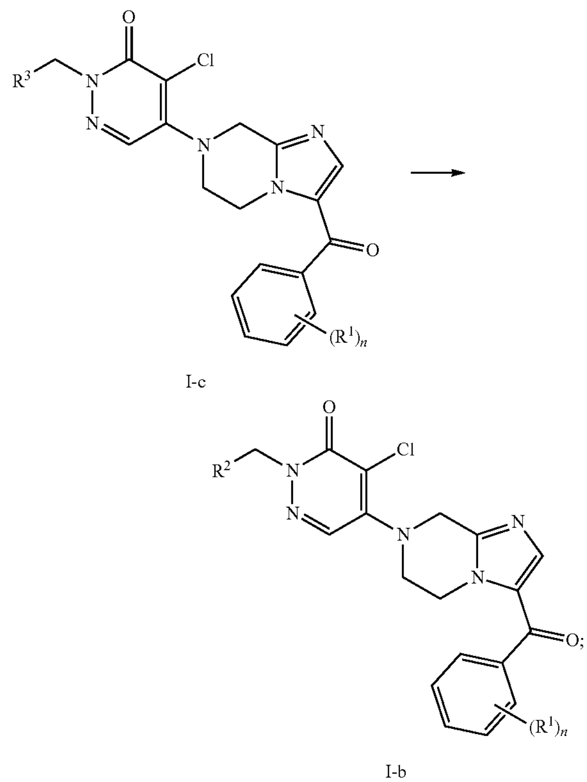

I-c

I-b wherein $R^2$ is

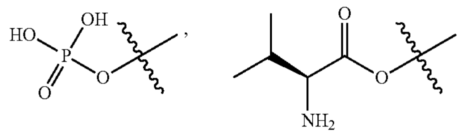

-continued

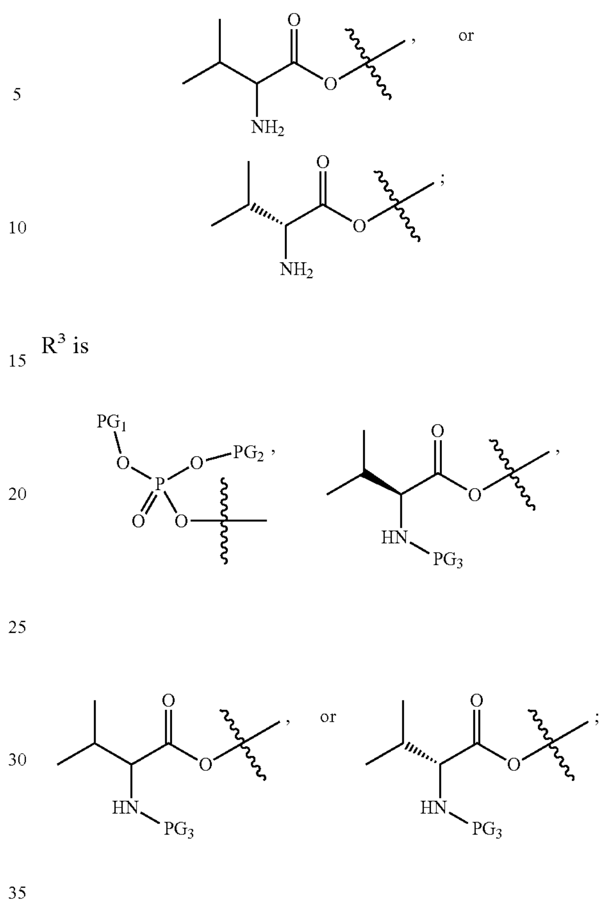

or $R^3$ is or $PG_1$ and $PG_2$ are hydroxy protective groups; $PG_3$ is an amino protective group; $R^1$ and n are as defined above;

the method 2 comprises the following step: in a solvent, carrying out a substitution reaction between compound III-1 with chlorosulfonic acid or dimethylcarbamoyl chloride to obtain the compound represented by formula I-b;

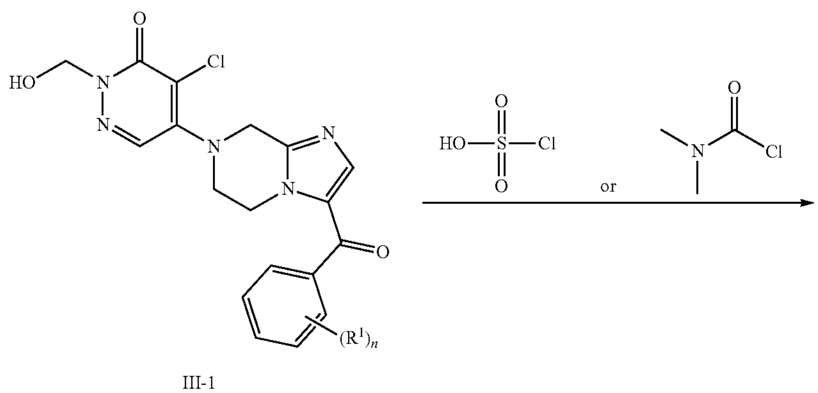

III-1

-continued

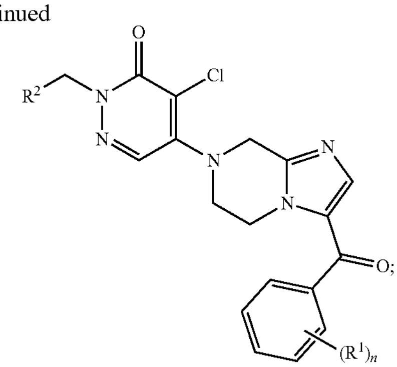

I-b wherein $R^2$ is

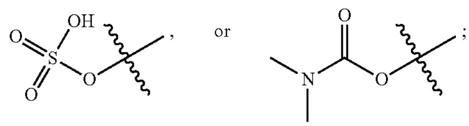

or $R^1$ and n are as defined above.

In the preparation method, in method 1, preferably, $PG_1$ and $PG_2$ are the same, more preferably, both $PG_1$ and $PG_2$ are t-Bu.

In the preparation method, in method 1, preferably, $PG_3$ is Boc.

In the preparation method, in method 1, the acid may be conventional in the art, for example trifluoroacetic acid or a 1,4-dioxane solution of hydrogen chloride.

In the preparation method, in method 1, the solvent may be conventional in the art, for example dichloromethane and/or ethyl acetate.

In the preparation method, in method 2, the solvent may be conventional in the art, for example acetonitrile.

In the preparation method, in method 2, when $R^2$ is

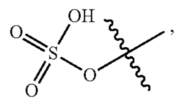 [SMILES: *OS(=O)(=O)O]

the solvent may be conventional in the art, for example acetonitrile.

In the preparation method, in method 2, when $R^2$ is

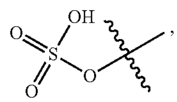 [SMILES: *OS(=O)(=O)O]

the molar ratio of the chlorosulfonic acid to the compound III-1 may be conventional in the art, for example (3 to 6):1, for another example 5:1.

In the preparation method, in method 2, when $R^2$ is

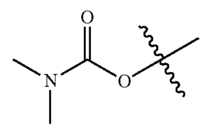

the solvent may be conventional in the art, for example tetrahydrofuran.

In the preparation method, in method 2, when $R^2$ is

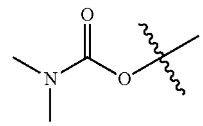

the molar ratio of the dimethylcarbamoyl chloride to the compound III-1 may be conventional in the art, for example (1 to 2):1, for another example 1:1.

The present disclosure also provides a compound represented by formula I-c-1:

I-c-1

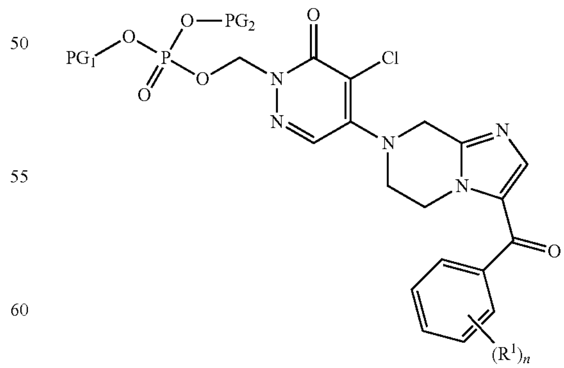

wherein $R^1$, n, $PG_1$, and $PG_2$ are as defined above;

preferably, the compound represented by formula I-c-1 is the following compound:

1-7

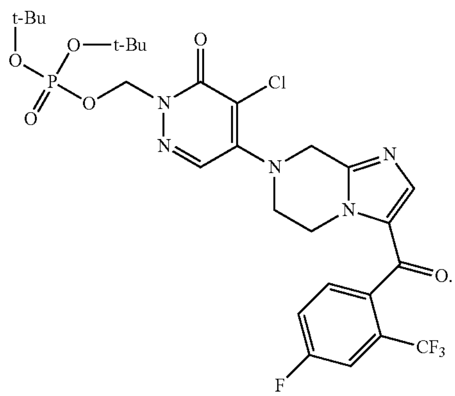

The present disclosure also provides a compound represented by formula I-c-2:

I-c-2

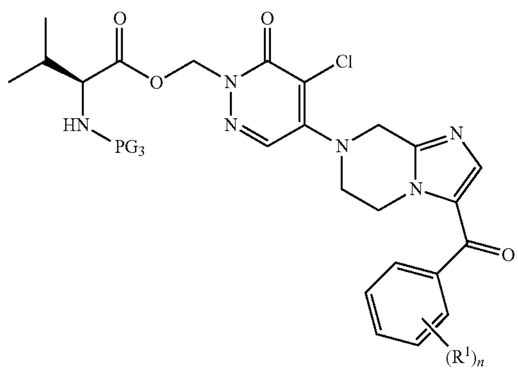

wherein $R^1$, n, and $PG_3$ are as defined above;

preferably, the compound represented by formula I-c-2 is the following compound:

2-2

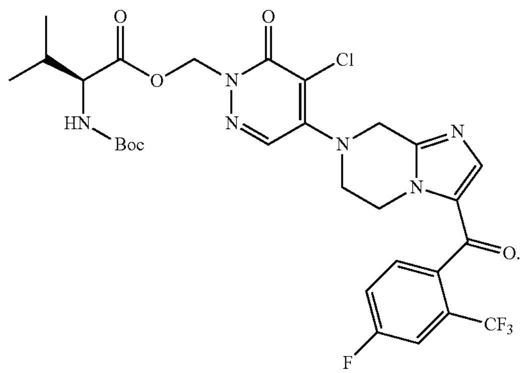

The present disclosure also provides a compound represented by formula III-1:

III-1

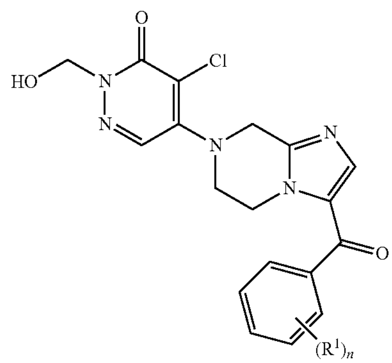

wherein $R^1$ and n are as defined above;

preferably, the compound represented by formula III-1 is the following compound:

3-1

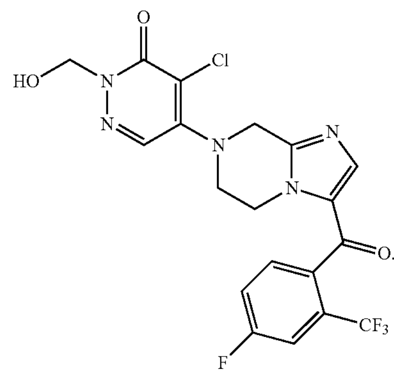

The present disclosure also provides a pharmaceutical composition, comprising substance X and a pharmaceutical excipient; the substance X is the compound represented by formula I-a, the tautomer thereof, the pharmaceutically acceptable salt thereof, the solvate thereof, or the solvate of the pharmaceutically acceptable salt thereof.

The present disclosure also provides a use of substance X in the manufacture of a TRPC5 inhibitor, the substance X is the compound represented by formula I-a, the tautomer thereof, the pharmaceutically acceptable salt thereof, the solvate thereof, or the solvate of the pharmaceutically acceptable salt thereof, and the TRPC5 inhibitor is used in vivo.

The present disclosure also provides a use of substance X in the manufacture of a medicament, the substance X is the compound represented by formula I-a, the tautomer thereof, the pharmaceutically acceptable salt thereof, the solvate thereof, or the solvate of the pharmaceutically acceptable salt thereof, and the medicament is a medicament for the treatment and/or prevention of a disease mediated by TRPC5.

In the use, the disease mediated by TRPC5 can be a psychiatric disorder, a neurological disorder, a neurodegenerative disorder, or nephropathy.

The psychiatric disorder, neurological disorder, or neurodegenerative disorder can be selected from: a disease associated with dysregulated emotional processing (for example, borderline personality disorder or depression, such as major depression, major depressive disorder, psychiatric depression, dysthymia, postpartum depression, and bipolar disorder), a disorder associated with anxiety and fear (for example, post-traumatic stress disorder, panic disorder, agoraphobia, social phobia, generalized anxiety disorder, panic disorder, social anxiety disorder, obsessive-compulsive disorder, and separation anxiety), a memory disorder (for example, Alzheimer's disease, amnesia, aphasia, brain injury, brain tumor, chronic fatigue syndrome, Creutzfeldt-Jakob disease, dissociative amnesia, fugue amnesia, Huntington's disease, learning disorder, sleeping disorder, multiple personality disorder, pain, post-traumatic stress disorder, schizophrenia, sports injury, stroke, and Wernicke-Korsakoff Syndrome), a disorder associated with impaired impulse control and addiction, Alzheimer's disease, Parkinson's disease, Huntington's disease, amyotrophic lateral sclerosis, epilepsy, and other brain disorders caused by trauma or other injury including aging.

The nephropathy can be focal segmental glomerulosclerosis (FSGS), minimal change nephropathy, or diabetic nephropathy.

The present disclosure also provides a use of substance X in the manufacture of a medicament, the substance X is the compound represented by formula I-a, the tautomer thereof, the pharmaceutically acceptable salt thereof, the solvate thereof, or the solvate of the pharmaceutically acceptable salt thereof, and the medicament is a medicament for the treatment and/or prevention of a psychiatric disorder, a neurological disorder, a neurodegenerative disorder, or nephropathy.

In the use, the psychiatric disorder, neurological disorder, or neurodegenerative disorder can be selected from: a disease associated with dysregulated emotional processing (for example, borderline personality disorder or depression, such as major depression, major depressive disorder, psychiatric depression, dysthymia, postpartum depression, and bipolar disorder), a disorder associated with anxiety and fear (for example, post-traumatic stress disorder, panic disorder, agoraphobia, social phobia, generalized anxiety disorder, panic disorder, social anxiety disorder, obsessive-compulsive disorder, and separation anxiety), a memory disorder (for example, Alzheimer's disease, amnesia, aphasia, brain injury, brain tumor, chronic fatigue syndrome, Creutzfeldt-Jakob disease, dissociative amnesia, fugue amnesia, Huntington's disease, learning disorder, sleeping disorder, multiple personality disorder, pain, post-traumatic stress disorder, schizophrenia, sports injury, stroke, and Wernicke-Korsakoff Syndrome), a disorder associated with impaired impulse control and addiction, Alzheimer's disease, Parkinson's disease, Huntington's disease, amyotrophic lateral sclerosis, epilepsy, and other brain disorders caused by trauma or other injury including aging.

In the use, the nephropathy can be focal segmental glomerulosclerosis (FSGS), minimal change nephropathy, or diabetic nephropathy.

Unless otherwise stated, the terms used in the description and claims of the present disclosure have the following meanings:

The term "pharmaceutically acceptable salt" refers to the salt prepared by the compound of the present disclosure and a relatively nontoxic and pharmaceutically acceptable acid or base. When the compound of the present disclosure contains a relatively acidic functional group, a base addition salt can be obtained by bringing the prototype form of the compound into contact with a sufficient amount of the pharmaceutically acceptable base in a pure solution or a suitable inert solvent. Pharmaceutically acceptable base addition salts include, but are not limited to, lithium salts, sodium salts, potassium salts, calcium salts, aluminum salts, magnesium salts, zinc salts, bismuth salts, ammonium salts, diethanolamine salts. When the compound of the present disclosure contains a relatively basic functional group, an acid addition salt can be obtained by bringing the prototype form of the compound into contact with a sufficient amount of pharmaceutically acceptable acid in a pure solution or a suitable inert solvent. The pharmaceutically acceptable acids include inorganic acids, including but not limited to: hydrochloric acid, hydrobromic acid, hydroiodic acid, nitric acid, carbonic acid, phosphoric acid, phosphorous acid, sulfuric acid, etc. The pharmaceutically acceptable acids include organic acids, and the organic acids include, but are not limited to: acetic acid, propionic acid, oxalic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, salicylic acid, tartaric acid, methanesulfonic acid, isonicotinic acid, acid citric acid, oleic acid, tannic acid, pantothenic acid, hydrogen tartrate, ascorbic acid, gentisic acid, fumaric acid, gluconic acid, sugar acid, formic acid, ethanesulfonic acid, pamoic acid (i.e., 4,4'-methylene-bis(3-hydroxy-2-naphthoic acid)), amino acids (such as glutamic acid, arginine), etc. When the compounds of the present disclosure contain relatively acidic and relatively basic functional groups, they can be converted into base addition salts or acid addition salts. For details, see Berge et al., "Pharmaceutical Salts", Journal of Pharmaceutical Science 66: 1-19 (1977), or Handbook of Pharmaceutical Salts: Properties, Selection, and Use (P. Heinrich Stahl and Camille G. Wermuth, ed., Wiley-VCH, 2002).

The term "solvate" refers to a substance formed by combining a compound of the present disclosure with a stoichiometric or non-stoichiometric solvent. Solvent molecules in the solvate can exist in an ordered or unordered arrangement. The solvent includes, but is not limited to, water, methanol, ethanol, etc.

The "pharmaceutically acceptable salt" and "solvate" in the term "solvate of pharmaceutically acceptable salt" are defined as above, and the solvate of pharmaceutically acceptable salt refers to a substance formed by combining the compound of the present disclosure: 1, with a relatively nontoxic and pharmaceutically acceptable acid or base, and, 2, with a stoichiometric or non-stoichiometric solvent. The "solvate of pharmaceutically acceptable salt" includes, but is not limited to, the hydrochloride monohydrate of the compound of the present disclosure.

When an arbitrary variable (e.g., $R^1$) appears many times in the definition of a compound, the definition of each occurrence of the variable has nothing to do with the definitions of other occurrences, and their meanings are independent of each other and have no influence on each other. Therefore, if a group is substituted by 1, 2, or 3 $R^1$ groups, that is, the group may be substituted by up to 3 $R^1$ groups, and the definition of $R^1$ groups of this position and the definition of $R^1$ groups of the remaining positions are independent of each other. Additionally, combinations of substituents and/or variables are permissible only if such combinations result in stable compounds.

The term "halogen" refers to fluorine, chlorine, bromine, or iodine.

The term "alkyl" refers to a saturated straight or branched monovalent hydrocarbon group having 1 to 10 carbon atoms (for example, $C_1$-$C_8$ alkyl, for another example, $C_1$-$C_6$ alkyl, $C_1$-$C_5$ alkyl, $C_1$-$C_4$ alkyl, $C_1$-$C_3$ alkyl). Examples of alkyl include, but are not limited to: methyl, ethyl, 1-propyl, 2-propyl, 1-butyl, 2-methyl-1-butyl, 2-butyl, 2-methyl-2- propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, and 1-octyl.

The term "cycloalkyl" refers to a saturated, cyclic hydrocarbon group having 3 to 20 carbon atoms, preferably 3 to 12 carbon atoms, more preferably 3 to 6 carbon atoms. Examples of cycloalkyl include, but are not limited to, cyclopropyl, cyclobutyl, cyclopentyl, and cyclohexyl.

The term "alkoxy" refers to the group $R^X$—O—, wherein $R^X$ is the alkyl as defined above. Examples of alkoxy include, but are not limited to, methoxy, ethoxy, propoxy, etc.

The term "pharmaceutical excipients" refers to the excipients and additives used in the manufacture of drugs and the formulation of prescriptions, which are all substances contained in pharmaceutical preparations except active ingredients. Available in the Pharmacopoeia of the People's Republic of China (2020 Edition) Part IV, or, Handbook of Pharmaceutical Excipients (Raymond C Rowe, 2009 Sixth Edition).

The term "treatment" refers to therapeutic therapy. When referring to a specific disorder, treatment refers to: (1) ameliorating one or more biological manifestations of the disease or disorder, (2) interfering with (a) one or more points in the biological cascade leading to or causing the disorder or (b) one or more biological manifestations of the disorder, (3) ameliorating one or more symptoms, effects, or side effects associated with the disorder, or one or more symptoms, effects or side effects associated with the disorder or its treatment, or (4) slowing the progression of the disorder or one or more biological manifestations of the disorder.

The term "prevention" refers to the reduction of the risk of acquiring or developing diseases or disorders.

The term "patient" refers to any animal that will or has received the administration of the compound or composition according to the example of the present disclosure, preferably a mammal. The term "mammal" includes any mammal. Examples of mammals include, but are not limited to, cows, horses, sheep, pigs, cats, dogs, mice, rats, rabbits, guinea pigs, monkeys, humans, etc., preferably humans.

The term "therapeutically effective amount" refers to the amount of a compound that is sufficient to effectively treat the diseases or disorders described herein when administered to a patient. The "therapeutically effective amount" will vary according to the compound, the disease and its severity, and the age of the patient to be treated, but it can be adjusted by those skilled in the art as needed.

On the basis of not violating the common sense in the field, the preferred conditions above can be arbitrarily combined to obtain the preferred examples of the present disclosure.

The reagents and raw materials used in the present disclosure are commercially available.

The positive progressive effect of the present disclosure is that the compounds of the present disclosure have better water solubility and pharmacokinetic properties.

BRIEF DESCRIPTION OF THE DRAWING

The FIGURE is a graph showing the distribution of plasma concentration in CD-1 mouse tissues after a single intragastric administration of compound L015.

DETAILED DESCRIPTION OF THE PREFERRED EMBODIMENT

The present disclosure is further described below by the way of examples, but the present disclosure is not thereby limited to the scope of the described examples. The experimental methods for which the specific conditions are not specified in the following examples are selected according to the conventional methods and conditions, or according to the commodity instructions.

Terms and Representative Reagents

The terms used in the following specific experimental descriptions refer to (unless otherwise stated) the following reagents:

NBS: N-bromosuccinimide; DIEA: N,N-diisopropylethylamine; EA: ethyl acetate; DCM: dichloromethane; DMF: N,N-dimethylformamide; THF: tetrahydrofuran; i.v.: intravenous injection; PO: oral administration.

I. Preparation of the Compounds of the Present Disclosure and their Effect Data:

Example 1: Preparation of Compound (5-chloro-4-(3-(4-fluoro-2-(trifluoromethyl)benzoyl)-5,6-dihydroimidazo[1,2-a]pyrazin-7(8H)-yl)-6-oxopyridazin-1(6H)-yl)methyl Dihydrogen Phosphate (Compound 1)

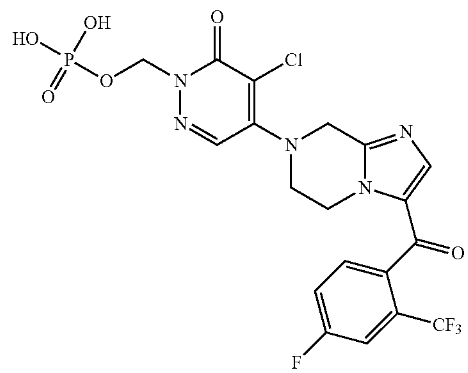

1

Synthesis Route:

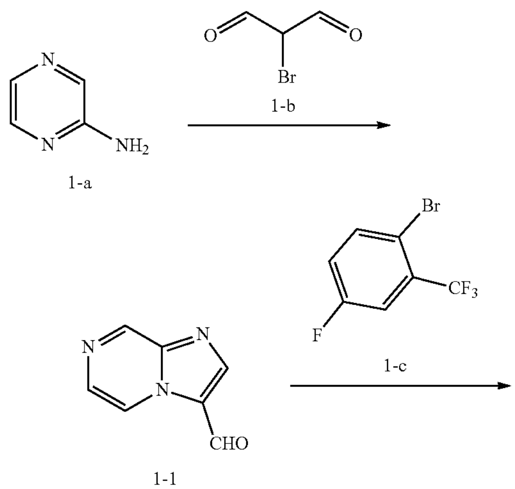

1-a 1-b 1-c 1-1

-continued

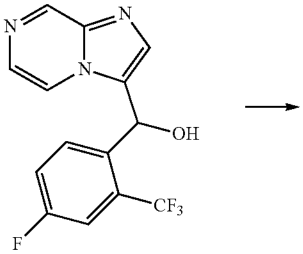

1-2

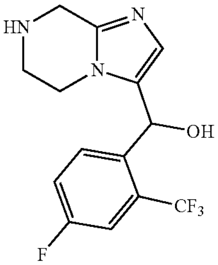

1-3

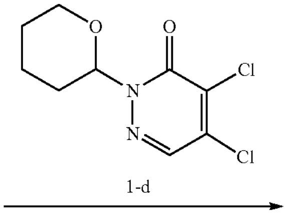

1-d

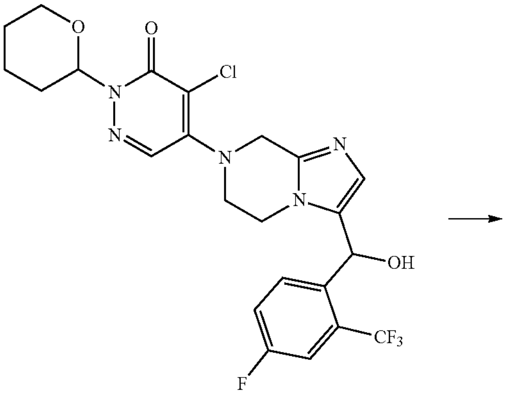

1-4

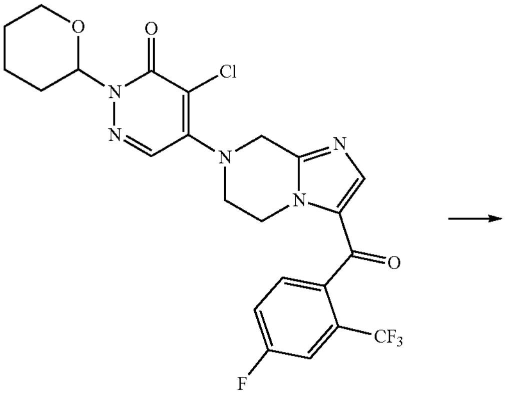

1-5

-continued

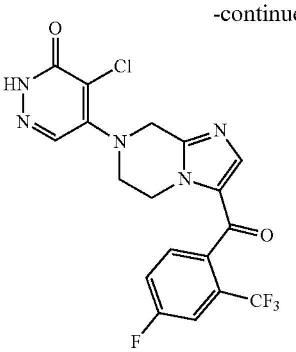

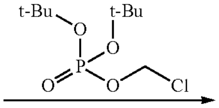

1-6

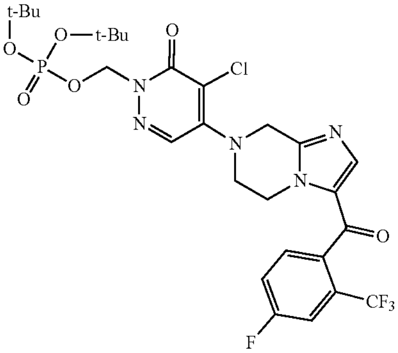

1-7

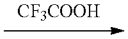

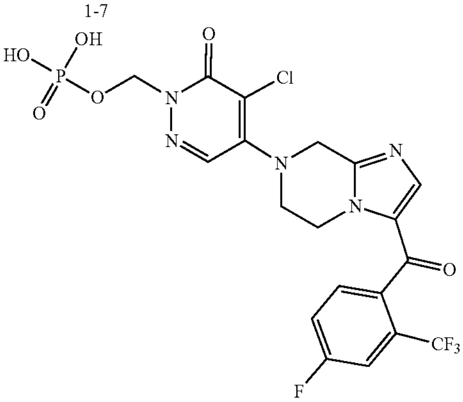

1

1.1 Preparation of Compound 1-1

Compound 1-a (10.0 g, 0.11 mol) was dissolved in anhydrous ethanol (100 mL), and compound 1-b (15.8 g, 0.11 mmol) was added thereto, and the reaction mixture was stirred at 90° C. for 2 hours. After the reaction was completed, the reaction mixture was cooled to room temperature, and evaporated to dryness by rotary evaporation to remove the solvent to obtain a black viscous substance, and then 30 mL of a solution of hydrogen chloride (4 mol/L) in 1,4-dioxane was added thereto, and the mixture was stirred at 25° C. for 12 hours. After the reaction was completed, 50 mL of water was added thereto, and the pH of the mixture was adjusted to about 8 with sodium carbonate solution, and then the mixture was extracted with ethyl acetate (50 mL*4). The organic phase was washed with saturated brine (30 mL*2), dried over anhydrous sodium sulfate, filtered, and the filtrate was concentrated under reduced pressure and then the residue was recrystallized with ethyl acetate for three times to obtain compound 1-1 (3.5 g). LC-MS $[M+H]^+$ =148.0.

1.2 Preparation of Compound 1-2

Compound 1-c (7.47 g, 30.6 mmol) was dissolved in tetrahydrofuran (50 mL). To a mixture containing magnesium chips (1.47 g, 61.2 mmol) and iodine (50 mg, 2 mmol) in tetrahydrofuran (20 mL) was added 2 mL of the resulting solution dropwise under nitrogen atmosphere, and the reaction mixture was heated with a hair dryer until the solution was clear and transparent. To the reaction system was added the remaining solution of compound 1-c in tetrahydrofuran dropwise. The mixture was stirred at 70° C. for 1 hour then cooled to room temperature. To the solution of compound 1-1 (3.00 g, 20.4 mmol) in tetrahydrofuran was added the mixture dropwise at −70° C. under nitrogen atmosphere. The mixed system was stirred at −70° C. for 2 hours. After the reaction was completed, ammonium chloride solution (50 mL) was added thereto, and the mixture was extracted with ethyl acetate (50 mL*3). The organic phase was washed with saturated brine (30 mL*2), dried over anhydrous sodium sulfate, filtered, and the filtrate was concentrated. Then the crude product was separated by silica gel column chromatography (dichloromethane/methanol=100/1 (v/v)) to obtain compound 1-2 (3.2 g).

LC-MS $[M+H]^+$=312.07.

1.3 Preparation of Compound 1-3

Compound 1-2 (1.10 g, 3.50 mmol) was dissolved in tetrahydrofuran (25 mL). Wet Pd/C (10%, 400 mg) was added thereto, and the resulting mixture was stirred for 12 hours at room temperature under hydrogen atmosphere. After the reaction was completed, the mixture was filtered, and the filtrate was concentrated under reduced pressure to obtain compound 1-3 (1.0 g).

LC-MS $[M+H]^+$=316.2.

1.4 Preparation of Compound 1-4

Compound 1-3 (200 mg, 0.63 mmol) was dissolved in anhydrous butanol (1 mL), and 1-d (189 mg, 0.76 mmol) and N,N-diisopropylethylamine (245 mg, 1.90 mmol) were added thereto, and the mixture was stirred at 120° C. for 2 hours under nitrogen atmosphere. The reaction mixture was concentrated, and the crude product was separated by silica gel column chromatography (dichloromethane/methanol=100/1 (v/v)) to obtain compound 1-4 (160 mg).

LC-MS $[M+H]^+$=528.2.

1.5 Preparation of Compound 1-5

Compound 1-4 (200 mg, 0.297 mmol) was dissolved in anhydrous dichloromethane (20 mL), then Dess-Martin periodinane (630 mg, 1.485 mmol) was added thereto. The mixture was stirred at 40° C. for 8 hours under nitrogen atmosphere. After the reaction was completed, the pH of the mixture was adjusted to about 9 with sodium hydroxide solution, and the mixture was extracted with dichloromethane (10 mL*3). The organic phase was dried over anhydrous sodium sulfate, filtered, and the filtrate was concentrated under reduced pressure. The crude product was separated by silica gel column chromatography (dichloromethane/methanol=100/1 (v/v)) to obtain compound 1-5 (150 mg). LC-MS $[M+H]^+$=526.2.

1.6 Preparation of Compound 1-6

Compound 1-5 (150 mg, 0.28 mmol) was dissolved in a solution of hydrogen chloride in 1,4-dioxane (2 mL, 4 mol/L), and the mixture was stirred at 25° C. for 1 hour. The mixture was concentrated under reduced pressure to obtain a crude product, and the crude product was purified by preparative high performance liquid chromatography to obtain compound 1-6 (216 mg). LC-MS $[M+H]^+$=441.8. $^1H$ NMR (400 MHz, DMSO-$d_6$): δ 13.08 (s, 1H), 8.02 (s, 1H), 7.85 (dd, J=9.3, 2.5 Hz, 1H), 7.79 (dd, J=8.5, 5.5 Hz, 1H), 7.68 (td, J=8.5, 2.5 Hz, 1H), 7.35 (s, 1H), 4.83 (s, 2H), 4.52 (t, J=5.2 Hz, 2H), 3.91 (t, J=5.3 Hz, 2H).

1.7 Preparation of Compound 1-7

To a reaction flask was added compound 1-6 (300 mg, 0.68 mmol), sodium iodide (132 mg, 0.88 mmol), and tetrahydrofuran (3 mL), and the mixture was stirred to dissolve, cooled to about 0° C. under an ice bath. To the reaction mixture was added lithium tert-butanol (1 M tetrahydrofuran solution, 0.82 mL, 0.82 mmol) dropwise, and the dropwise addition was completed. Then di-tert-butyl chloromethylphosphonate (230 mg, 0.83 mmol) was added to the reaction mixture, and the reaction mixture was warmed to room temperature and reacted for 12 hours. The reaction mixture was quenched with water, extracted with ethyl acetate (5 mL*3), and the organic phase was washed with saturated brine (10 mL), dried over anhydrous sodium sulfate, filtered, then the filtrate was concentrated under reduced pressure to obtain compound 1-7 (300 mg), which was directly used in the next reaction step without further purification.

LC-MS $[M+H]^+$=664.2.

1.8 Preparation of Compound (5-chloro-4-(3-(4-fluoro-2-(trifluoromethyl)benzoyl)-5,6-dihydroimidazo[1,2-a]pyrazin-7(8H)-yl)-6-oxopyridazin-1(6H)-yl)methyl dihydrogen phosphate (Compound 1)

Compound 1-7 (300 mg, 0.45 mmol) was dissolved in dichloromethane (3 mL). To the reaction mixture was added trifluoroacetic acid (0.6 mL) dropwise with stirring, then the mixture was stirred at 25° C. for 1 hour. After the reaction was completed, the mixture was concentrated under reduced pressure to obtain a crude product, and the crude product was purified by preparative high performance liquid chromatography to obtain compound 1 (112.3 mg).

LC-MS $[M+H]^+$=552.0; $^1H$ NMR (400 MHz, DMSO-$d_6$): δ 8.14 (s, 1H), 7.84 (dd, J=9.2, 2.8 Hz, 1H), 7.79 (dd, J=8.4, 5.6 Hz, 1H), 7.68 (td, J=8.4, 2.6 Hz, 1H), 7.36 (s, 1H), 5.68 (d, J=7.6 Hz, 2H), 4.91 (s, 2H), 4.54 (t, J=5.6 Hz, 2H), 3.98 (t, J=5.6 Hz, 2H).

Example 2: Preparation of (5-chloro-4-(3-(4-fluoro-2-(trifluoromethyl)benzoyl)-5,6-dihydroimidazo[1,2-a]pyrazin-7(8H)-yl)-6-oxopyridazin-1(6H)-yl)methyl L-valinate (Compound 2)

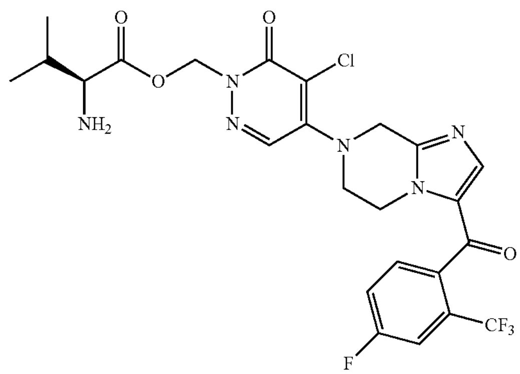

2

Synthesis Route:

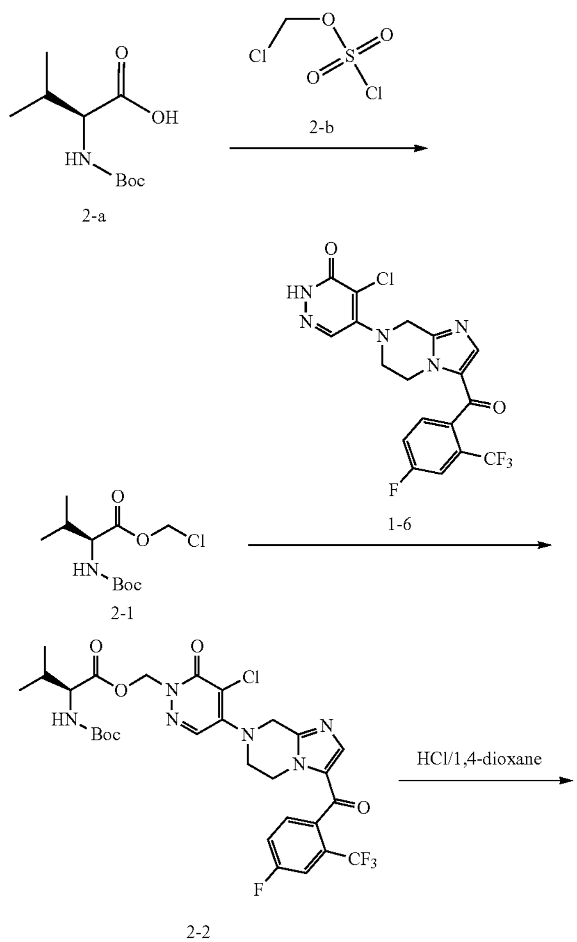

2-a 2-1

2-2

-continued

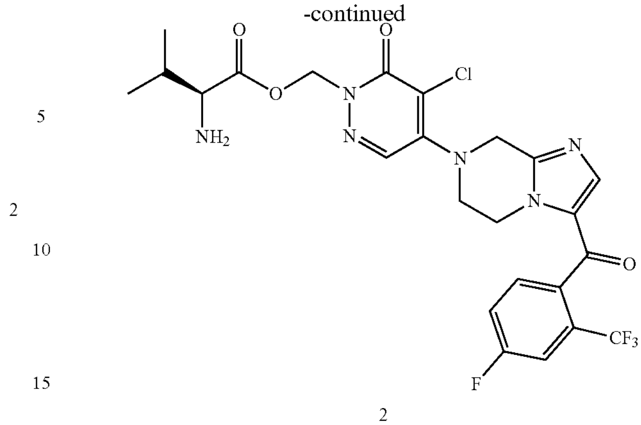

2

2.1 Preparation of Compound 2-1

Compound 2-a (3 g, 13.81 mmol), sodium bicarbonate (4.7 g, 55.23 mmol), and tetrabutylammonium bisulfate (468 mg, 1.38 mmol) were dissolved in a mixed solvent of dichloromethane (30 mL) and water (30 mL), and the resulting reaction mixture was stirred at room temperature for 5 minutes, then cooled to 0° C. The reaction mixture was added with compound 2-b (2.73 g, 16.57 mmol), then warmed to room temperature and stirred for 2 hours. After the reaction was completed, the reaction mixture was slowly poured into sodium bicarbonate aqueous solution, extracted with dichloromethane (50 mL*3). The combined organic phase was washed with saturated brine, dried over anhydrous sodium sulfate, and filtered, and the filtrate was concentrated under reduced pressure. The crude product was purified by a silica gel chromatography column (petroleum ether/ethyl acetate=1/0 to 4/1 (v/v)) to obtain compound 2-1 (3.6 g).

$^1$H NMR (400 MHz, DMSO-$d_6$): δ 7.35 (d, J=7.6 Hz, 1H), 5.94 (d, J=6.0 Hz, 1H), 5.84 (d, J=6.0 Hz, 1H), 3.92-3.88 (m, 1H), 2.06-2.01 (m, 1H), 1.39-1.34 (m, 9H), 0.89 (dd, $J_1$=6.8, $J_2$=1.6 Hz, 6H).

2.2 Preparation of Compound 2-2

Compound 1-6 (200 mg, 0.45 mmol) and sodium iodide (88.22 mg, 0.59 mmol) were dissolved in tetrahydrofuran (3 mL). The reaction mixture was added with lithium tert-butoxide (0.54 mL, 1 M tetrahydrofuran solution), and then added with a tetrahydrofuran (2 mL) solution of compound 2-1 (145.4 mg, 0.55 mmol), warmed to room temperature and stirred overnight. The reaction was completed. The reaction mixture was combined with the previous batch and concentrated under reduced pressure. The crude product was purified by a silica gel chromatography column (petroleum ether/ethyl acetate=1/4 to 0/1 (v/v)) to obtain compound 2-2 (400 mg).

LC-MS [M-Boc+H]$^+$=571.2.

2.3 Preparation of Compound (5-chloro-4-(3-(4-fluoro-2-(trifluoromethyl)benzoyl)-5,6-dihydroimidazo[1,2-a]pyrazin-7(8H)-yl)-6-oxopyridazin-1(6H)-yl)methyl L-valinate (Compound 2)

Compound 2-2 (350 mg) was dissolved in ethyl acetate (10 mL). To the reaction was added a solution of hydrogen chloride in 1,4-dioxane (10 mL, 4 M), and the reaction mixture was stirred for 2 hours at room temperature. After the reaction was completed, the reaction mixture was slowly poured into sodium bicarbonate aqueous solution, extracted with ethyl acetate (30 mL*3). The combined organic phase was washed with saturated brine, dried over anhydrous sodium sulfate and filtered, and the filtrate was concentrated under reduced pressure. The crude product was purified by preparative high performance liquid chromatography to obtain compound 2 (47.4 mg).

LC-MS $[M+H]^+$=571.1;

$^1$H NMR (400 MHz, DMSO-$d_6$): δ 8.24 (s, 1H), 8.16 (s, 1H), 7.84 (dd, $J_1$=8.4, $J_2$=2.4 Hz, 1H), 7.78 (dd, $J_1$=8.8, $J_2$=5.6 Hz, 1H), 7.69 (dd, $J_1$=4.4, $J_2$=2.4 Hz, 1H), 7.35 (s, 1H), 5.97 (dd, $J_1$=22.4, $J_2$=9.6 Hz, 2H), 4.91 (s, 2H), 4.53 (t, J=4.8 Hz, 2H), 3.98 (t, J=4.8 Hz, 2H), 3.14 (d, J=5.2 Hz, 1H), 1.83-1.78 (m, 1H), 0.86 (d, J=6.8 Hz, 3H), 0.81 (d, J=6.8 Hz, 2H).

Example 3: Preparation of Compound (5-chloro-4-(3-(4-fluoro-2-(trifluoromethyl)benzoyl)-5,6-dihydroimidazo[1,2-a]pyrazin-7(8H)-yl)-6-oxopyridazin-1(6H)-yl)methyl Hydrogen Sulfate (Compound 3)

3

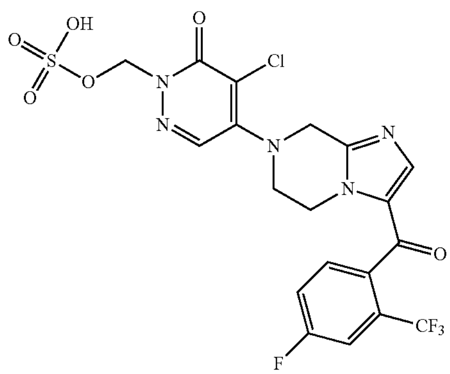

Synthesis Route:

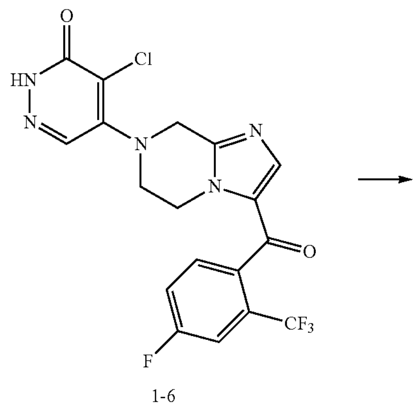

1-6

-continued

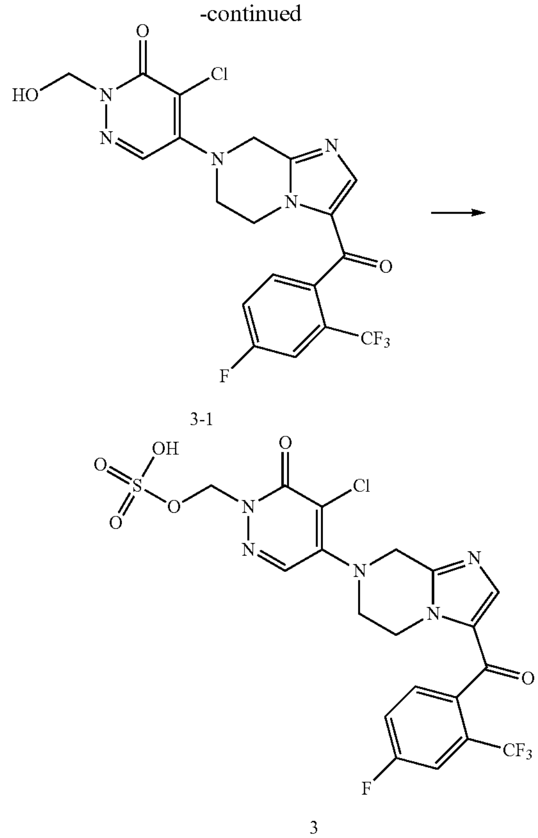

3-1

3

3.1 Preparation of Compound 3-1

Compound 1-6 (400 mg, 0.90 mmol) was dissolved in ethanol (4 mL) and 10% formaldehyde aqueous solution (4 mL), and the reaction mixture was reacted at 80° C. for 32 hours. After the reaction was completed, the reaction mixture was concentrated under reduced pressure to obtain a crude product, and the crude product was purified by a silica gel chromatography column (dichloromethane/methanol=10/1 (v/v)) to obtain compound 3-1 (35 mg). LC-MS $[M+H]^+$=472.1.

3.2 Preparation of Compound (5-chloro-4-(3-(4-fluoro-2-(trifluoromethyl)benzoyl)-5,6-dihydroimidazo[1,2-a]pyrazin-7 (8H)-yl)-6-oxopyridazin-1 (6H)-yl)methyl hydrogen sulfate (Compound 3)

Compound 3-1 (35 mg, 0.07 mmol) was dissolved in acetonitrile (10 mL). Then chlorosulfonic acid (43 mg, 0.37 mmol) was added thereto, and the reaction was carried out at 0° C. for 2 hours, and then the reaction was completed. The pH of the mixture was adjusted to 8 with saturated sodium bicarbonate aqueous solution, and the reaction mixture was concentrated under reduced pressure to obtain a crude product, and the crude product was then purified by preparative high performance liquid chromatography to obtain compound 3 (5.8 mg). LC-MS $[M+H]^+$=552.05; $^1$H NMR (400 MHz, DMSO-$d_6$): δ 12.91 (s, 1H), 8.00 (s, 1H), 7.86-7.82 (m, 2H), 7.67 (td, $J_1$=8.4 Hz, $J_2$=2.4 Hz, 1H), 7.37 (s, 1H), 5.55-5.53 (m, 1H), 4.66-4.63 (m, 1H), 4.30-3.98 (m, 6H).

Example 4: Preparation of Compound (5-chloro-4-(3-(4-fluoro-2-(trifluoromethyl)benzoyl)-5,6-dihydroimidazo[1,2-a]pyrazin-7(8H)-yl)-6-oxopyridazin-1(6H)-yl)methyl Dimethylcarbamate Compound 4)

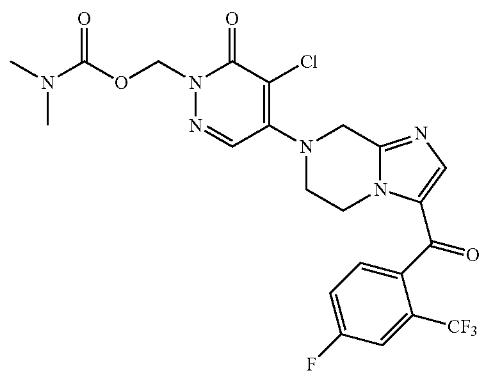

4

Synthesis Route:

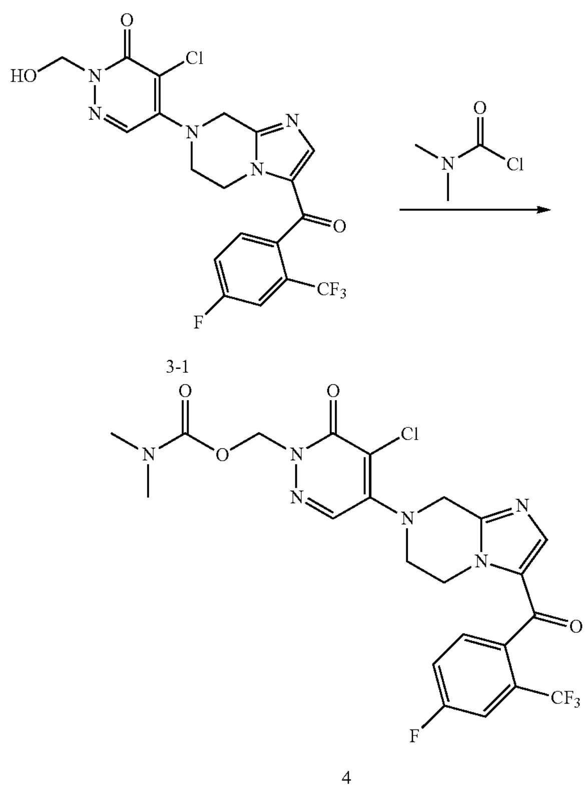

3-1

4

Compound 3-1 (50 mg, 0.11 mmol) was dissolved in tetrahydrofuran (3 mL) and then cooled to 0° C. To the reaction mixture was added sodium hydride (4 mg, 0.11 mmol, purity of 60% dispersed in mineral oil), and the reaction mixture was warmed to room temperature and then cooled to 0° C. after stirring for half an hour. To the reaction mixture was added a solution of dimethylcarbamoyl chloride (11 mg, 0.11 mmol) in tetrahydrofuran (0.5 mL), and the reaction was warmed to room temperature and stirred for 3 hours. After the reaction was completed, the reaction mixture was concentrated under reduced pressure, and the residue was purified by preparative high performance liquid chromatography to obtain compound 4 (1.2 mg). LCMS $[M+H]^+$=543.1;

$^1$H NMR (400 MHz, $CDCl_3$): δ 7.95 (s, 1H), 7.60-7.55 (m, 1H), 7.52 (dd, $J_1$=8.8, $J_2$=2.4 Hz, 1H), 7.36 (t, J=6.8 Hz, 1H), 7.31 (s, 1H), 5.32 (s, 1H), 4.89 (d, J=14.4 Hz, 1H), 4.52-4.43 (m, 1H), 4.24-4.00 (m, 5H), 3.19 (s, 3H), 2.93 (s, 3H).

Effect Example 1: Biological Activity Test Assay

TRPC5 is a type of non-selective cation channel with permeability to calcium ions. Therefore, TRPC5 agonist Englerin A (EA) and TRPC5 inhibitor Pico145 were used as positive controls in this experiment. Fluo-4 AM fluorescence dye was used to indirectly reflect the effect of the compound on TRPC5 channel by detecting intracellular $Ca^{2+}$ in TRPC5-HEK 293 cells.

1. Cell Culture 1.1 Revival of TRPC5-HEK 293 Cells

Revival solution: 100% high glucose DMEM

Selection medium: high glucose DMEM+10% FBS+1% P/S+1% HEPES+Blasticidin (5 μg/mL)+Hygromycine (50 μg/mL)

Induction medium: high glucose DMEM+10% FBS+1% P/S+1% HEPES+Doxycycline (1 μg/mL)

Revival process: A cryopreservation solution containing TRPC5-HEK 293 cells was taken out from the liquid nitrogen tank, and transferred from the ice box to the water bath, and then dissolved in circles to a small piece of ice, and the cryopreservation solution was transferred to the revival solution, and centrifuged at 1000 rpm for 5 minutes, and then the supernatant was discarded, then the residue was transferred to the selection medium, and expanded in a $CO_2$ incubator (5% $CO_2$, humidity of 95%, 37° C.).

1.2 Seeding TRPC5-HEK 293 Cells in Plates 14 hours before the real-time fluorescence experiment, cells were washed with PBS and digested with trypsin-EDTA. Cells were diluted to 200,000 cells/mL with induction medium and seeded onto a 96-well black wall bottom transparent plate coated with poly-D-lysine (PDL) (stock solution of 10 mg/mL, final concentration of 10 μg/mL) at 100 μL/well, i.e., 20,000 cells/well.

2. Preparation of Buffer 500 mL of external solution for detecting TRPC5 calcium signals: 4.0908 g of NaCl, 0.1864 g of KCl, 0.111 g of $CaCl_2$, 0.0476 g of $MgCl_2$, 0.9 g of glucose, 1.1915 g of HEPES (2-[4-(2-hydroxyethyl)piperazin-1-yl]ethanesulfonic acid).

Calcium fluorescent dye: an external solution for detecting TRPC5 calcium signals containing Fluo-4 with a final concentration of 4 μM (containing 0.5% BSA)

3. Preparation of Compounds

Agonist: Englerin A (EA)

Agonist concentration: Since the $EC_{50}$ of TRPC5 activated by the EA was about 0.35 nM, 0.3 nM of EA was used.

Positive inhibitor: Pico145 (HC608)

Positive inhibitor concentration: 100 nM

Compounds to be Tested: Compound 1-6 and Compound 1

Concentration of the compound to be tested: routinely prepared, prepared as a drug solution that was 8 times the final concentration of the test (the final concentrations of the test were: 1 nM, 3 nM, 10 nM, 30 nM, 100 nM, 300 nM, and 1000 nM) with 60 μL per well of the bottom plate.

4. Data Processing

The fluorescence value of the Flipr was tested and subtracted the value of the undyed cell well (i.e., background fluorescence value), and the Graphpad Prism 6.0 software was used for statistics and data processing, and the trajectory map was normalized by removing the baseline and displayed as a ratio. The dose-effect diagram was used to calculate AUC (area under the curve of the curve formed by the calcium flux signal), and the data and the log of the compound concentration were collected. The $IC_{50}$ value was calculated using log[Inhibitor] vs. response Variable slope.

The results are shown in Table 1: Compound 1 has no inhibitory activity against TRPC5 channels.

TABLE 1

| Compound number | TRPC5 inhibitory activity, $IC_{50}$ (nM) |
|---|---|
| Compound 1-6 | 11.5 |
| Compound 1 | >10000 |

Effect Example 2: PK Study of Male SD Rats after Single Intragastric Administration of Compound (Using 5% Solutol as a Solvent)

1. Experimental Purpose

To explore the time-plasma concentration curves of the compound in the plasma of male rats after single intragastric administration of compound 1 (125 mg/kg) and compound 1-6 (100 mg/kg) of the present disclosure and to obtain PK parameters ($C_{max}$, $T_{max}$, $AUC_{last}$, $AUC_{inf}$, $T_{1/2}$, MRT, etc.) of the rats after single administration of compound 1 and compound 1-6 of the present disclosure.

2. Experimental Protocol 2.1 Experimental Instruments

TABLE 2

| Name | Model/specification | Manufacturer |
|---|---|---|
| Electronic analytical balance | MS105Du | Mettler-Toledo |

TABLE 2-continued

| Name | Model/specification | Manufacturer |
|---|---|---|
| Electronic scale | YP2001 | Shanghai Yoke Instrument |
| High speed refrigerated centrifuge | STR16 | Thermo Fisher Scientific |

2.2 Experimental Preparation 2.2.1 Experimental Preparation of the Compound of the Present Disclosure (Compound 1)

Rats: SD rats, SPF grade, 3 males, weight range of 180 to 200 g (source: Beijing Vital River Laboratory Animal Technology Co., Ltd., certificate number: 110011201109106028);

feeding conditions: ordinary animal house feeding, free access to food and water, 3 animals/cage rearing, 12/12 hours light/dark cycle adjustment (7:00 am/7:00 pm), temperature of 23±1° C.

Dispensing: After accurately weighing the compounds in the PO group, 5% solutol of the required volume was added thereto first, vortexed and mixed evenly for 2 min, sonicated for 30 min, stirred for 2 hours until no visible particles were visible to the naked eye, and the drug was administered while stirring, and the middle layer of the drug solution was taken for drug administration.

Before administration, a sample of the drug solution must be retained for analysis, and two accurate samples of 100 μL each of the upper, middle, and lower suspensions were taken and sent for analysis and testing on the same day, and the backup samples were stored in a −75° C. refrigerator for future use.

2.2.2 Experimental Preparation of Compound 1-6

Rats: SD rats, SPF grade, 3 males, weight range of 220 to 300 g (source: SPF (Beijing) Biotechnology Co., Ltd., certificate number: 110324200103216838);

feeding conditions: ordinary animal house feeding, free access to food and water, 3 animals/cage rearing, 12/12 hours light/dark cycle adjustment (7:00 am/7:00 pm), temperature of 23±1° C.

Dispensing: After accurately weighing compound 1-6 in the PO group, 5% solutol of the required volume was added first, vortexed and mixed evenly for 2 min, sonicated for 30 min, stirred for 3 hours until no visible particles were visible to the naked eye;

the drug solution was prepared and used immediately, and a sample of the drug solution must be retained for analysis, and two samples of 100 μL each of the upper, middle, and lower suspensions were taken and sent for analysis and testing on the same day.

2.3 Dosage Regimen

The rats were randomly divided into 3 groups according to body weight, and the specific grouping and administration are as follows:

TABLE 3

| Grouping and administration information of compounds of the present disclosure | | | | | | | | | |
|---|---|---|---|---|---|---|---|---|---|
| Group | Subject | Number (female/male) | Administration Route | Vehicle | Administration Dose (mg/kg) | Drug Concentration (mg/mL) | Administration Volume (mL/kg) | Plasma analyte |
| PO | Compound 1 (suspension solution) | 0/3 | PO | 5% solutol | 125 | 12.5 | 10 | Compounds 1 and 1-6 |

1. The animals in the PO group were fasted overnight with free access to water before administration, and the food was returned 4 hours after administration;
2. time points for blood sampling: the time points for blood sampling in the PO group were 0.167, 0.5, 1, 2, 3, 4, 6, 9, 12, and 24 hours.

TABLE 4

| Grouping and administration information of compound 1-6 | | | | | | | | |
|---|---|---|---|---|---|---|---|---|
| Group | Subject | Number (female/male) | Administration Route | Vehicle | Administration Dose (mg/kg) | Drug Concentration (mg/mL) | Administration Volume (mL/kg) | Plasma Analyte |
| 1 | Compound 1-6 (suspension solution) | 0/3 | PO | 5% solutol | 100 | 10 | 10 | Compound 1-6 |

1. The animals in the PG group were fasted overnight with free access to water before administration, and the food was returned 4 hours after administration;
2. time points for blood sampling: the time points for blood sampling in the PG group were 0.167, 0.5, 1, 2, 3, 4, 6, 9, 12, and 24 hours.

2.4 Sample Collection and Preparation

After administration to rats, blood was collected from the orbital venous plexus according to the sampling time points. About 0.2 to 0.3 mL of blood was collected at each time point and transferred to an anticoagulant EP tube (containing 4 μL of EDTA-$K_2$, 375 mg/mL). The tube was gently inverted three times and stored in an ice box (not exceeding 30 minutes). After centrifugation at 3500×g for 10 minutes at 4° C., the supernatant was transferred to a labeled EP tube. Hemolysis was observed and recorded, and the sample was sent to bioassay for testing. If the sample could not be analyzed the same day, the sample was stored at −80° C. until further testing (be careful not to perform multiple freezing/thawing processes).

2.5 Sample Analysis

2.5.1 Sample Analysis of Compounds of the Present Disclosure

2.5.1.1 Experimental Instrument

High performance liquid chromatography pump (pump): Exion LC AD Pump, Sciex Company
Auto sampler: Exion LC AD Autosampler, Sciex Company
Column oven: Exion LC AD Column Oven, Sciex Company
Mass spectrometer: AB Sciex Qtrap 3500
High-speed refrigerated centrifuge (centrifuge): Thermo Fisher, ST16R, GG1206085-093
Analytical balance (electronic balance): Mettler Toledo, MS-105DU, GG1206363
Micro vortex (vortex): Shanghai Huxi Analysis Instrument Factory, WH-2, GG1206487

Experimental material: rat plasma (EDTA-$K_2$)
Analyte: compound 1-6
Internal standard: tolbutamide
Analytical method: liquid chromatography-mass spectrometry (LC-MS)

2.5.1.2 Mass Spectrometry Conditions

Mass spectrometry parameters
Ion source: ion electrospray (ESI)
Ionization mode: positive ion mode (Positive)
Detection mode (mode): multi-reaction monitoring (MRM)
Ion spray voltage: 5500
Ion spray temperature (turbo ion spray temp): 550° C.
Curtain gas: 35
Collision cell gas (CAD gas): medium
Nebulizing gas (gas 1): 55.00
Auxiliary gas (gas 2): 55.00
Detection of Ion Pairs:

TABLE 5

| Compound | Molecular ion (m/z) | Fragment ion (m/z) | Residence time (msec) | Declustering potential (DP) (V) | Collision energy (CE) (eV) |
|---|---|---|---|---|---|
| Tolbutamide | 271.1 | 155.0 | 25 | 60 | 26 |
| Compound 1-6 | 442.2 | 406.2 | 40 | 97 | 36 |

2.5.1.3 Liquid Phase Method

Chromatographic column: poroshell 120 EC-C18 (2.1×50 mm, 2.7 m)
Mobile phase A: 0.1% formic acid aqueous solution
Mobile phase B: a solution of 0.1% formic acid in methanol Auto sampler wash solution (rinse port wash solution): methanol:water:acetonitrile:isopropanol=1:1:1:1

Column temperature: 40° C.

Flow rate: 0.65 mL/min

Auto sampler temperature (sample tray temp): 15° C.

Injection volume: 8 μL

Height of presser foot (needle stroke): 49 mm

Auto sampler rinse setting (rinse pump setting): rinse only the injection port

Auto sampler rinse mode (rinse mode): rinse before inhalation

Auto sampler rinse volume for needle (rinse volume): 500 μL

Dip time when rinsing the injection needle (rinse dip time): 2 seconds

Elution Gradient:

TABLE 6

| Time (min) | Module | Function | Value (%) |
|---|---|---|---|
| 0.2 | Pumps | Pump B Conc. | 15 |
| 1.60 | Pumps | Pump B Conc. | 99 |
| 2.40 | Pumps | Pump B Conc. | 99 |
| 2.41 | Pumps | Pump B Conc. | 15 |
| 3 | Pumps | Pump B Conc. | 15 |

2.5.1.4 Pretreatment Method

Sample pretreatment process: 3 μL of working solution was taken, and 57 μL of blank matrix was added into a 1.5 mL centrifuge tube, and then 240 μL of acetonitrile solution containing 200 ng/mL tolbutamide and 0.1% FA was added to precipitate protein. The mixture was vortexed and mixed for 1 minute, and then centrifuged in a 4° C. centrifuge at 13000 rpm for 15 minutes. 100 μL of supernatant was taken and added to another 96 deep well plate, and 100 μL of methanol:water (1:3, v:v) solution containing 0.1% FA was added. The mixture was mixed with shaking for 1 min, and centrifuged at 3500 rpm for 5 min in a 96-well plate centrifuge and the sample was injected directly.

2.5.2 Sample Analysis of Compound 1-6

2.5.2.1 Experimental Instrument

High performance liquid chromatography pump (Pump): LC-30AD, Shimadzu Company

Auto sampler: SIL-30AC, Prominence, Shimadzu Company

Column oven: CTO-30A, Shimadzu Company

Mass spectrometer: AB Sciex Qtrap 3500

High-speed refrigerated centrifuge (centrifuge): Thermo Fisher, ST16R, GG1206085-093

Analytical balance (electronic balance): Mettler Toledo, MS-105D, GG1206363

Micro vortex (vortex): Shanghai Huxi Analysis Instrument Factory, WH-2, GG1206487

Experimental material: rat plasma (EDTA-$K_2$)

Analyte: compound 1-6

Internal standard: tolbutamide

Analytical method: liquid chromatography-mass spectrometry (LC-MS)

2.5.2.2 Mass Spectrometry Conditions

Mass spectrometry parameters

Ion source: ion electrospray (ESI)

Ionization mode: positive ion mode (Positive)

Detection mode (mode): multi-reaction monitoring (MRM)

Ion spray voltage: 5500

Ion spray temperature (turbo ion spray temp): 550° C.

Curtain gas: 35

Collision cell gas (CAD gas): medium

Nebulizing gas (gas 1): 55.00

Auxiliary gas (gas 2): 55.00

Detection of ion pairs:

TABLE 7

| Compound | Molecular ion (m/z) | Fragment ion (m/z) | Residence time (msec) | Declustering potential (DP) (V) | Collision energy (CE) (eV) |
|---|---|---|---|---|---|
| Tolbutamide | 271.1 | 155.0 | 25 | 60 | 26 |
| Compound 1-6 | 442.2 | 406.2 | 30 | 97 | 36 |

2.5.2.3 Liquid Phase Method

Chromatographic column: poroshell 120 EC-C18 (4.6×50 mm, 2.7 m)

Mobile phase A: 0.1% formic acid aqueous solution

Mobile phase B: a solution of 0.1% formic acid in methanol

Auto sampler wash solution (rinse port wash solution): methanol:acetonitrile:water:isopropanol=1:1:1:1

Flow rate: 0.8 mL/min

Auto sampler temperature (sample tray temp): 15° C.

Injection volume: 15 μL

Height of presser foot (needle stroke): 49 mm

Auto sampler rinse setting (rinse pump setting): rinse only the injection port

Auto sampler rinse mode (rinse mode): rinse before inhalation

Auto sampler rinse volume for needle (rinse volume): 500 μL

Dip time when rinsing the injection needle (rinse dip time): 2 seconds

Elution Gradient:

TABLE 8

| Time (min) | Module | Function | Value (%) |
|---|---|---|---|
| 0.01 | Pumps | Pump B Conc. | 35 |
| 0.20 | Pumps | Pump B Conc. | 35 |
| 1.40 | Pumps | Pump B Conc. | 99 |
| 2.40 | Pumps | Pump B Conc. | 99 |
| 2.41 | Pumps | Pump B Conc. | 35 |
| 3.00 | System Controller | Stop | N/A |

2.5.1.4 Pretreatment Method

Sample pretreatment process: 30 μL of sample was taken, and 120 μL of acetonitrile solution containing 0.1% FA and 200 ng/mL of mixed standard solution was added to precipitate the protein, vortexed and mixed well, and the sample was centrifuged at 13000 pm for 10 minutes in a centrifuge at 4° C. 100 μL of the supernatant was transferred to another 96 deep well plate, and 100 μL of methanol:water (1:3, v:v) solution was added, shaken and mixed for 10 minutes.

2.6 Data Analysis

The data would be analyzed using WinNonlin (version 5.2.1 Pharsight, Mountain View, CA) through a non-compartmental model to obtain PK parameters (selecting $C_{max}$, $T_{max}$, $AUC_{last}$, $AUC_{inf}$, $T_{1/2}$, MRT, and other parameters according to different routes of administration). The specific results are shown in Table 9, and the analyte of the data listed in the table is compound 1-6.

TABLE 9

| Compound and its dose | Animal group | Dose (mg/kg) | $C_{max}$ (ng/mL) | $T_{max}$ (hr) | $T_{1/2}$ (hr) | $AUC_{last}$ (ng/mL * hr) | $AUC_{INF}$ (ng/mL * hr) | $MRT_{last}$ (hr) |
|---|---|---|---|---|---|---|---|---|
| Compound | 1 | 100* | 8970 | 3.00 | 6.44 | 63796 | 71669 | 6.32 |
| 1 | 2 | 100* | 8240 | 1.00 | 9.77 | 70715 | 105256 | 8.81 |
| 125 mg/kg | 3 | 100* | 11400 | 1.00 | 7.30 | 132990 | 144787 | 8.09 |
| | Mean value | 100 | 9537 | 1.67 | 7.30 | 89167 | 107237 | 7.74 |
| Compound | 4 | 100 | 1210 | 4.00 | 5.95 | 13471 | 14501 | 8.03 |
| 1-6 | 5 | 100 | 1290 | 4.00 | 4.09 | 11214 | 11480 | 6.38 |
| 100 mg/kg | 6 | 100 | 1150 | 4.00 | 14.5 | 18235 | 27514 | 10.0 |
| | Mean value | 100 | 1217 | 4.00 | 5.02 | 14307 | 17832 | 8.15 |

100* herein indicates that 125 mg/kg of compound 1 is equivalent to 100 mg/kg of compound 1-6.

Experimental conclusion: Compared with compound 1-6, the compound of the present disclosure has better exposure.

I. Preparation and Effect Data of Compound 1-6 (Corresponding to Compound L015 in Example 15 Below) and its Analogues of the Present Disclosure:

Example 1: Preparation of Compound 4-chloro-5-(3-(2-(trifluoromethyl)benzyl)-5,6-dihydroimidazo[1,2-a]pyrazin-7(8H)-yl)pyridazin-3(2H)-one (L001)

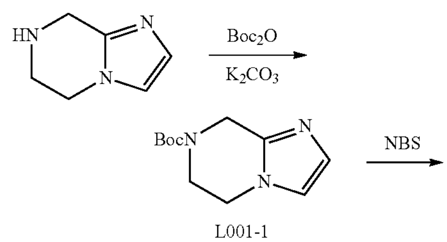

L001-1

-continued

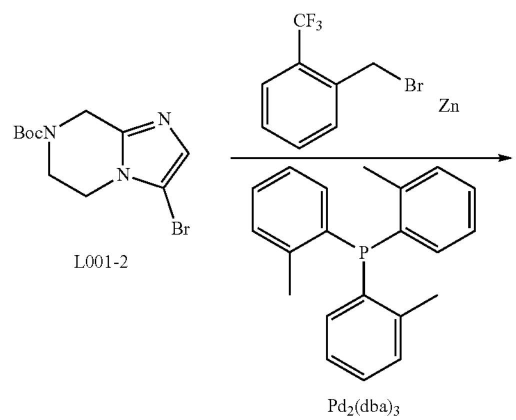

L001-2

-continued

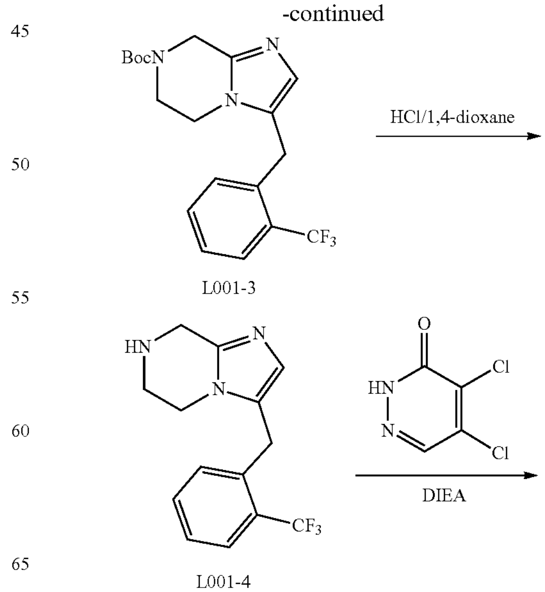

L001-3

L001-4

-continued

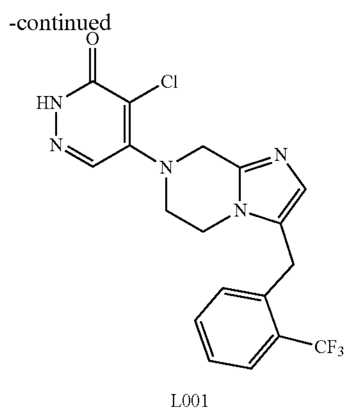

L001

1.1 Preparation of Compound tert-butyl 5,6-dihydroimidazo[1,2-a]pyrazine-7(8H)-carboxylate (L001-1)

To a single-necked flask was added 5,6,7,8-tetrahydroimidazo[1,2-a]pyrazine (700 mg, 5.68 mmol) and $K_2CO_3$ (1.57 g, 11.37 mmol), and added $H_2O$ (8 mL) and THE (8 mL), and then added $(Boc)_2O$ dropwise after the dissolution was completed. The reaction mixture was reacted overnight at room temperature after the addition was completed. TLC (DCM/MeOH=10/1) showed that the reaction was completed. The reaction mixture was added with NaCl to make it saturated, extracted with EA, and the organic phase was dried over anhydrous sodium sulfate and concentrated to obtain L001-1 (1.2 g) as a brown solid.

1.2 Preparation of Compound tert-butyl 3-bromo-5,6-dihydroimidazo[1,2-a]pyrazine-7(8H)-carboxylate (L001-2)

To a single-necked flask was added tert-butyl 5,6-dihydroimidazo[1,2-a]pyrazine-7(8H)-carboxylate (1.2 g, 5.37 mmol), and added DMF (10 mL), and then added NBS (1.15 g, 6.45 mmol) slowly after the dissolution was completed. The reaction mixture was reacted overnight at room temperature after the addition was completed. TLC (DCM/MeOH=10/1) showed that the reaction was completed, and the reaction mixture was subjected to preparative separation (MeCN, $H_2O$, 0.05% TFA) to obtain L001-2 (700 mg) as a pale yellow solid.

1.3 Preparation of Compound tert-butyl 3-(2-(trifluoromethyl)benzyl)-5,6-dihydroimidazo[1,2-a]pyrazine-7(8H)-carboxylate (L001-3)

To a single-necked flask was added 2-(trifluoromethyl) benzyl bromide (791.1 mg, 3.31 mmol) and Zn (8.27 mmol), and added anhydrous THE (5 mL). The reaction mixture was reacted overnight at room temperature under nitrogen atmosphere. To the single-necked flask was added $Pd_2(dba)_3$ (91.6 mg), tri(o-tolyl)phosphine (50.3 mg), and tert-butyl 3-bromo-5,6-dihydroimidazo[1,2-a]pyrazine-7(8H)-carboxylate (500 mg, 1.65 mmol), then the reaction mixture was reacted at 70° C. for 2 hours under nitrogen atmosphere. TLC (pure EA) showed that the reaction was completed, the reaction mixture was extracted with EA, and the organic phase was washed with saturated brine, concentrated, and then the residue was purified by silica gel column chromatography to obtain L001-3 (80 mg) as a colorless liquid.

1.4 Preparation of Compound 3-(2-(trifluoromethyl) benzyl)-5,6,7,8-tetrahydroimidazo[1,2-a]pyrazine (L001-4)

tert-Butyl 3-(2-(trifluoromethyl)benzyl)-5,6-dihydroimidazo[1,2-a]pyrazine-7(8H)-carboxylate (60 mg, 157.3 μmol) was dissolved in DCM (2 mL); after the dissolution was completed, a solution of HCl in 1,4-dioxane (2 mL, 4 M) was added thereto with stirring, and the reaction mixture was reacted at room temperature for 3 hours after the addition was completed. TLC (pure EA with 1 drop of ammonia water) showed that the reaction was completed. The reaction mixture was concentrated to obtain L001-4 (45 mg) as a white solid.

1.5 Preparation of Compound 4-chloro-5-(3-(2-(trifluoromethyl)benzyl)-5,6-dihydroimidazo[1,2-a]pyrazin-7(8H)-yl)pyridazin-3(2H)-one To a single necked flask was added 3-(2-(trifluoromethyl) benzyl)-5,6,7,8-tetrahydroimidazo[1,2-a]pyrazine (43 mg, 152.9 μmol), and then added 4,5-dichloropyridazin-3(2H)-one (211.1 mg, 1.28 mmol), DIEA (59.2 mg, 458.6 μmol), and DMF (2 mL). The reaction mixture was reacted overnight at 100° C. under nitrogen atmosphere. TLC (DCM/MeOH=10/1) showed that the reaction was completed. The crude product was separated by preparative HPLC ($H_2O$, MeCN, 0.05% TFA) and lyophilized to obtain L001 as a yellow solid (6.1 mg, purity of 97.71%).

LC-MS: $[M+H]^+$=410.05. $^1H$ NMR (400 MHz, DMSO-$d_6$) δ 13.08 (s, 1H), 7.97 (s, 1H), 7.80 (d, J=7.9 Hz, 1H), 7.65 (t, J=7.7 Hz, 1H), 7.53 (t, J=7.6 Hz, 1H), 7.33 (d, J=7.6 Hz, 1H), 7.18 (s, 1H), 4.96 (s, 2H), 4.24 (s, 2H), 4.12 (d, J=4.9 Hz, 2H), 3.93 (d, J=5.0 Hz, 2H).

Example 2: Preparation Process of Compound 4-chloro-5-(3-(4-fluoro-2-(trifluoromethyl)benzyl)-5,6-dihydroimidazo[1,2-a]pyrazin-7(8H)-yl) pyridazin-3(2H)-one (L002)

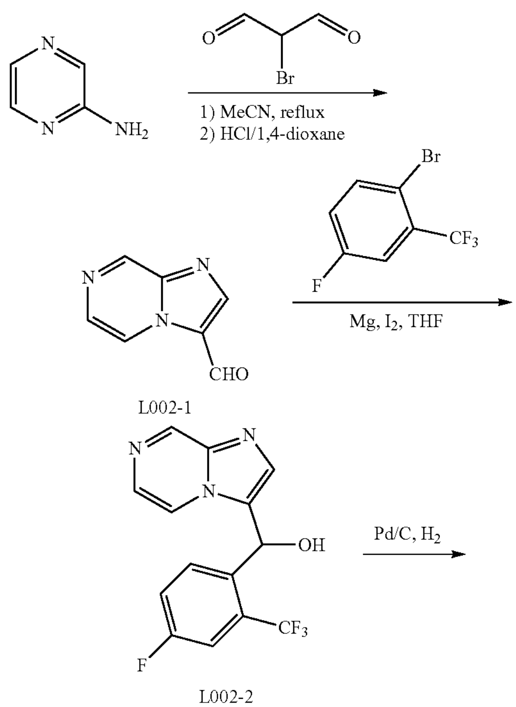

L002-1

L002-2

-continued

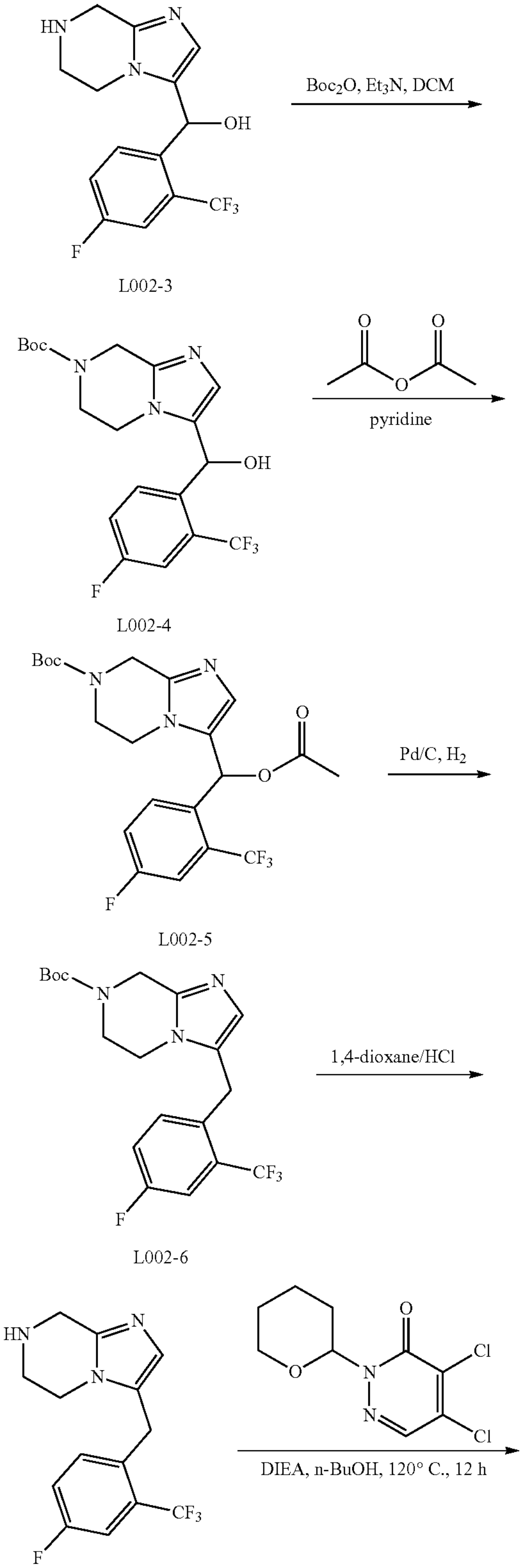

L002-3

L002-4

L002-5

L002-6

L002-7

-continued

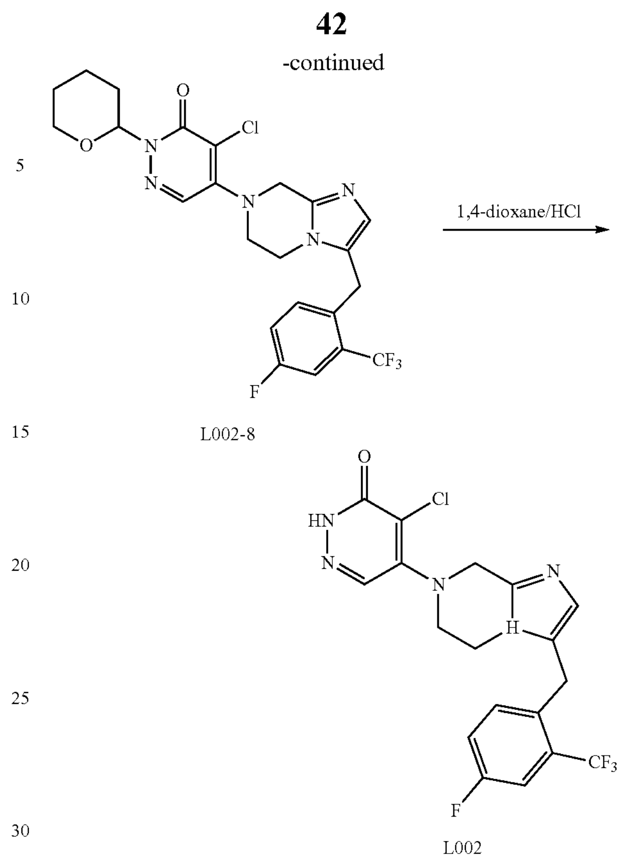

L002-8

L002

2.1 Preparation of Compound imidazo[1,2-a]pyrazine-3-carbaldehyde (L002-1)

Aminopyrazine (10.0 g, 0.11 mol) was dissolved in anhydrous ethanol (100 mL), and 2-bromomalondialdehyde (15.8 g, 0.11 mmol) was added thereto, and the mixture was stirred at 90° C. for 2 hours. After the reaction was completed, the mixture was cooled to room temperature, and evaporated to dryness by rotary evaporation to remove the solvent to obtain a black viscous substance. A solution of hydrogen chloride in 1,4-dioxane (4 mol/L, 30 mL) was added thereto, and the reaction mixture was stirred at 25° C. for 12 hours. After the reaction was completed, 50 mL of water was added thereto. The pH of the mixture was adjusted to about 8 with sodium carbonate solution, and then the mixture was extracted with ethyl acetate (50 mL*4). The organic phase was washed with saturated brine (30 mL*2), dried over anhydrous sodium sulfate, and evaporated to dryness by rotary evaporation to remove the solvent. The crude product was recrystallized with ethyl acetate for three times to obtain 3.5 g of a yellow solid with a yield of 22%. LC-MS $[M+H]^+$=148.0.

2.2 Preparation of Compound (4-fluoro-2-(trifluoromethyl)phenyl)(imidazo[1,2-a]pyrazin-3-yl)methanol (L002-2)

2-Bromo-5-fluorobenzotrifluoride (7.47 g, 30.6 mmol) was dissolved in tetrahydrofuran (50 mL). To a mixture containing magnesium chips (1.47 g, 61.2 mmol) and iodine (50 mg, 2 mmol) in tetrahydrofuran (20 mL) was added 2 mL of the resulting solution dropwise under nitrogen atmosphere, and the reaction mixture was heated with a hair dryer until the solution was clear and transparent. To the reaction system was added the remaining solution of 2-bromo-5-fluorobenzotrifluoride in tetrahydrofuran dropwise. The mixture was stirred at 70° C. for 1 hour and then cooled to room temperature. To a solution of imidazo[1,2-a]pyrazine-3-carbaldehyde (3.00 g, 20.4 mmol) in tetrahydrofuran was added the mixture dropwise at −70° C. under nitrogen atmosphere. The mixed system was stirred at −70° C. for 2 hours. After the reaction was completed, ammonium chloride solution (50 mL) was added thereto, and the mixture was extracted with ethyl acetate (50 mL*3). The organic phase was washed with saturated brine (30 mL*2), dried over anhydrous sodium sulfate, filtered, and the filtrate was concentrated, and the crude product was separated by silica gel column chromatography (DCM/MeOH=100/1) to obtain 3.20 g of a yellow solid with a yield of 41%. LC-MS $[M+H]^+$=312.07.

2.3 Preparation of Compound (4-fluoro-2-(trifluoromethyl)phenyl)(5,6,7,8-tetrahydroimidazo[1,2-a]pyrazin-3-yl)methanol (L002-3)

(4-Fluoro-2-(trifluoromethyl)phenyl)(imidazo[1,2-a]pyrazin-3-yl)methanol (1.10 g, 3.50 mmol) was dissolved in tetrahydrofuran (25 mL). Wet Pd/C (10%, 400 mg) was added thereto and the reaction mixture was stirred for 12 hours at room temperature under hydrogen atmosphere. After the reaction was completed, the reaction mixture was filtered, and the filtrate was evaporated to dryness by rotary evaporation to remove the solvent to obtain 1.00 g of a white solid with a yield of 90%, LC-MS $[M+H]^+$=316.2.

2.4 Preparation of Compound tert-butyl 3-((4-fluoro-2-(trifluoromethyl)phenyl)(hydroxy)methyl)-5,6-dihydroimidazo[1,2-a]pyrazine-7(8H)-carboxylate (L002-4)

(4-Fluoro-2-(trifluoromethyl)phenyl)(5,6,7,8-tetrahydroimidazo[1,2-a]pyrazin-3-yl)methanol (1.00 g, 3.16 mmol) was dissolved in tetrahydrofuran (10 mL)/water (5 mL), then sodium carbonate (1.00 g, 9.48 mmol) and di-tert-butyl dicarbonate (0.83 g, 3.79 mmol) were added thereto, and the reaction mixture was stirred at 25° C. for 2 hours. After the reaction was completed, water (50 mL) was added thereto, and the mixture was extracted with ethyl acetate (20 mL*3). The organic phase was washed with saturated brine (20 mL*2), dried over anhydrous sodium sulfate, and evaporated to dryness by rotary evaporation to remove the solvent to obtain 1.00 g of a yellow solid with a yield of 71%. LC-MS $[M+H]^+$=416.4.

2.5 Preparation of Compound tert-butyl 3-(acetoxy(4-fluoro-2-(trifluoromethyl)phenyl)methyl)-5,6-dihydroimidazo[1,2-a]pyrazine-7(8H)-carboxylate (L002-5)

tert-Butyl 3-((4-fluoro-2-(trifluoromethyl)phenyl)(hydroxy)methyl)-5,6-dihydroimidazo[1,2-a]pyrazine-7(8H)-carboxylate (1.00 g, 2.40 mmol) was dissolved in pyridine (10 mL), and acetic anhydride (300 mg, 2.89 mmol) was added thereto, and the reaction mixture was stirred at 25° C. for 2 hours. After the reaction was completed, the reaction mixture was evaporated to dryness by rotary evaporation to remove the solvent to obtain 1.10 g of a light yellow oil (product of 90%), LC-MS $[M+H]^+$=457.9.

2.6 Preparation of Compound tert-butyl 3-(4-fluoro-2-(trifluoromethyl)benzyl)-5,6-dihydroimidazo[1,2-a]pyrazine-7(8H)-carboxylate (L002-6)

tert-Butyl 3-(acetoxy(4-fluoro-2-(trifluoromethyl)phenyl)methyl)-5,6-dihydroimidazo[1,2-a]pyrazine-7(8H)-carboxylate (1.10 g, 2.40 mmol) was dissolved in tetrahydrofuran (10 mL), and wet palladium/carbon (10%, 100 mg) was added thereto. The reaction system was introduced with hydrogen and stirred at 25° C. for 2 hours. After the reaction was completed, the reaction mixture was filtered to remove palladium/carbon, and evaporated to dryness by rotary evaporation to remove the solvent to obtain 800 mg of a white solid with a yield of 85%.

LC-MS $[M+H]^+$=400.1.

2.7 Preparation of Compound 3-(4-fluoro-2-(trifluoromethyl)benzyl)-5,6,7,8-tetrahydroimidazo[1,2-a]pyrazine (L002-7)

tert-Butyl 3-(4-fluoro-2-(trifluoromethyl)benzyl)-5,6-dihydroimidazo[1,2-a]pyrazine-7(8H)-carboxylate (500 mg, 1.25 mmol) was dissolved in a solution of hydrogen chloride in 1,4-dioxane (4 mol/L, 5 mL), and the mixture was stirred at 25° C. for 2 hours.

After the reaction was completed, the mixture was evaporated to dryness by rotary evaporation to remove the solvent to obtain 450 mg of a light yellow substance as a crude product. LC-MS $[M+H]^+$=300.1.

2.8 Preparation of Compound 4-chloro-5-(3-(4-fluoro-2-(trifluoromethyl)benzyl)-5,6-dihydroimidazo[1,2-a]pyrazin-7(8H)-yl)-2-(tetrahydro-2H-pyran-2-yl)pyridazin-3(2H)-one (L002-8)

3-(4-Fluoro-2-(trifluoromethyl)benzyl)-5,6,7,8-tetrahydroimidazo[1,2-a]pyrazine hydrochloride (336 mg, 1.0 mmol) was dissolved in n-butanol (1.5 mL), and then 4,5-dichloro-2-(tetrahydro-2H-pyran-2-yl)pyridazin-3(2H)-one (374 mg, 1.5 mmol) and N,N-diisopropylethanamine (388 mg, 3.0 mmol) were added thereto, and the mixture was stirred at 120° C. for 3 hours under nitrogen atmosphere. After the reaction was completed, the mixture was evaporated to dryness by rotary evaporation to remove the n-butanol solvent, and the crude product was separated by silica gel column chromatography (DCM/MeOH=30:1) to obtain 200 mg of a yellow solid. The yield was 71%, LC-MS $[M+H]^+$=512.1.

2.9 Preparation of Compound 4-chloro-5-(3-(4-fluoro-2-(trifluoromethyl)benzyl)-5,6-dihydroimidazo[1,2-a]pyrazin-7(8H)-yl)pyridazin-3(2H)-one (L002)

4-Chloro-5-(3-(4-fluoro-2-(trifluoromethyl)benzyl)-5,6-dihydroimidazo[1,2-a]pyrazin-7(8H)-yl)-2-(tetrahydro-2H-pyran-2-yl)pyridazin-3(2H)-one (200 mg, 0.39 mmol) was dissolved in a solution of hydrogen chloride in 1,4-dioxane (2 mL, 4 mol/L), and the reaction mixture was stirred at 25° C. for 1 hour. After the reaction was completed, the solvent was evaporated to dryness by rotary evaporation and the residue was dissolved in dichloromethane (40 mL). The resulting mixture was washed with saturated sodium bicarbonate solution (20 mL), dried over anhydrous sodium sulfate, filtered, and the filtrate was concentrated. The crude product was purified by preparative chromatography to obtain 94.0 mg of a white solid with a yield of 57%. LC-MS $[M+H]^+$=427.9.

$^1$H NMR (400 MHz, DMSO-$d_6$) δ 13.13 (s, 1H), 7.99 (s, 1H), 7.73 (dd, J=9.3, 2.7 Hz, 1H), 7.57 (td, J=8.5, 2.7 Hz, 1H), 7.44 (dd, J=8.6, 5.5 Hz, 1H), 7.22 (s, 1H), 5.00 (s, 2H), 4.23 (s, 2H), 4.17 (d, J=5.1 Hz, 2H), 3.96 (d, J=5.0 Hz, 2H).

Example 3: Preparation of Compound 7-(5-chloro-6-oxo-1,6-dihydropyridazin-4-yl)-3-(4-fluoro-2-(trifluoromethyl)benzyl)-N-methyl-5,6,7,8-tetrahydroimidazo[1,2-a]pyrazine-2-carboxamide (L003)

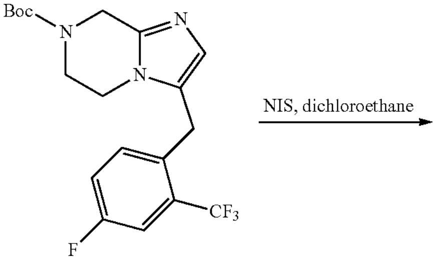

L002-6

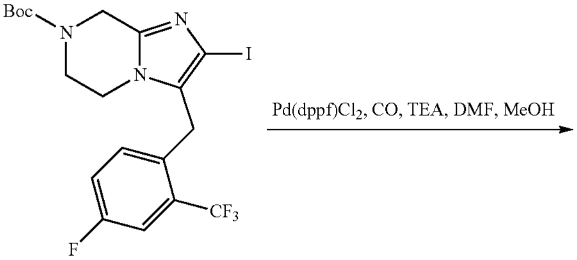

L003-1

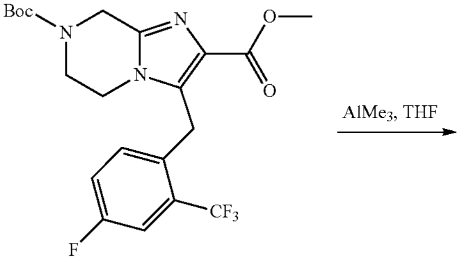

L003-2

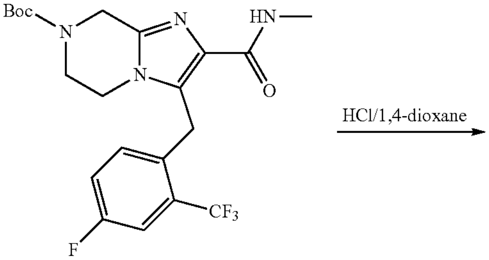

L003-3

-continued

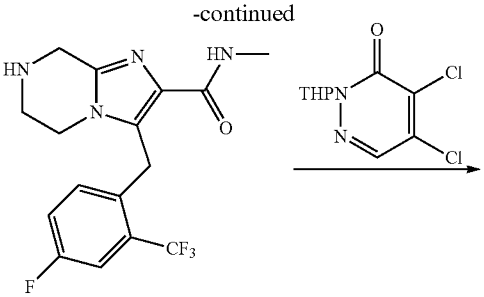

L003-4

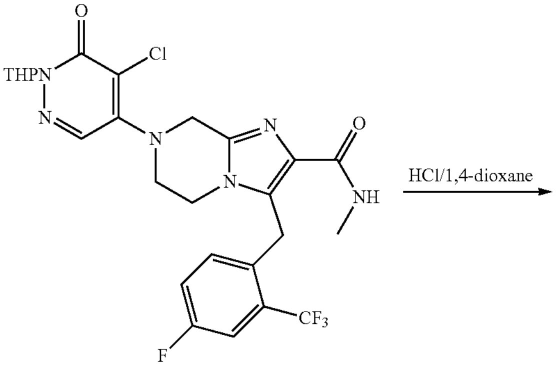

L003-5

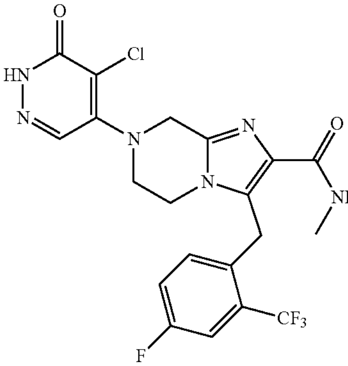

L003

3.1 Preparation of Compound tert-butyl 3-(4-fluoro-2-(trifluoromethyl)benzyl)-2-iodo-5,6-dihydroimidazo[1,2-a]pyrazine-7(8H)-carboxylate (L003-1)

tert-Butyl 3-(4-fluoro-2-(trifluoromethyl)benzyl)-5,6-dihydroimidazo[1,2-a]pyrazine-7(8H)-carboxylate (L002-6, 0.50 g, 1.25 mmol) was dissolved in dichloroethane (6 mL), and N-iodosuccinimide (0.42 g, 1.87 mmol) was added thereto. The reaction mixture was stirred at 90° C. for 1 hour under nitrogen atmosphere. After the reaction was completed, the reaction mixture was cooled to room temperature, and sodium thiosulfate aqueous solution (10 mL) was added thereto and stirred for 5 minutes, and then the reaction mixture was extracted with dichloromethane (10 mL*3). The organic phase was dried over anhydrous sodium sulfate, filtered, and the filtrate was concentrated to obtain a crude product, which was separated by silica gel column chromatography (dichloromethane/methanol=100/1) to obtain 200 mg of a yellow oil with a yield of 27%. LC-MS $[M+H]^+$=525.8.

3.2 Preparation of Compound methyl 7-(tert-butoxycarbonyl)-3-(4-fluoro-2-(trifluoromethyl)benzyl)-5,6-dihydroimidazo[1,2-a]pyrazine-2,7(8H)-2-carboxylate (L003-2)

tert-Butyl 3-(4-fluoro-2-(trifluoromethyl)benzyl)-2-iodo-5,6-dihydroimidazo[1,2-a]pyrazine-7(8H)-carboxylate (170 mg, 0.32 mmol), 1,1'-bis(diphenylphosphino)ferrocenepalladium dichloride (24 mg, 0.032 mmol), and triethylamine (162 mg, 1.6 mmol) were dissolved in methanol/N,N-dimethylformamide (3 mL/3 mL), and the reaction system was replaced with nitrogen, and then carbon monoxide was introduced and the reaction mixture was stirred at 70° C. for 16 hours. The reaction mixture was filtered, and the filtrate was evaporated to dryness by rotary evaporation. The crude product was purified by a silica gel column (dichloromethane/methanol=40/1) to obtain 126 mg of a yellow solid product with a yield of 85%. LC-MS $[M+H]^+$=458.

3.3 Preparation of Compound tert-butyl 3-(4-fluoro-2-(trifluoromethyl)benzyl)-2-(methylcarbamoyl)-5,6-dihydroimidazo[1,2-a]pyrazine-7(8H)-carboxylate (L003-3)

To trimethylaluminum (2 M hexane solution, 0.75 mL, 1.5 mmol) was added methylamine (2 M THE solution, 0.75 mL, 1.5 mmol) at 0° C., and the mixture was reacted for 0.25 hours, and then methyl 7-(tert-butoxycarbonyl)-3-(4-fluoro-2-(trifluoromethyl)benzyl)-5,6-dihydroimidazo[1,2-a]pyrazine-2,7(8H)-2-carboxylate (126 mg, 0.28 mmol) was added thereto. After the addition was completed, the reaction mixture was raised to 25° C. and stirred for 10 hours. The reaction mixture was quenched by adding hydrochloric acid (1 N) and evaporated to dryness by rotary evaporation, and the crude product was purified by a silica gel column (dichloromethane/methanol=30/1) to obtain 80 mg of a yellow solid product with a yield of 63%.

LC-MS $[M+H]^+$=457.

3.4 Preparation of Compound 3-(4-fluoro-2-(trifluoromethyl)benzyl)-N-methyl-5,6,7,8-tetrahydroimidazo[1,2-a]pyrazine-2-carboxamide hydrochloride (L003-4)

tert-Butyl 3-(4-fluoro-2-(trifluoromethyl)benzyl)-2-(methylcarbamoyl)-5,6-dihydroimidazo[1,2-a]pyrazine-7(8H)-carboxylate (80 mg, 0.175 mmol) was dissolved in dichloromethane (3 mL), and a solution of hydrogen chloride in 1,4-dioxane (3 mL, 4 M) was added thereto, and the reaction mixture was stirred at room temperature for 1 hour. The reaction mixture was concentrated under reduced pressure to obtain 70 mg of a yellow solid.

LC-MS $[M+H]^+$=357.

3.5 Preparation of Compound 7-(5-chloro-6-oxo-1-(tetrahydro-2H-pyran-2-yl)-1,6-dihydropyridazin-4-yl)-3-(4-fluoro-2-(trifluoromethyl)benzyl)-N-methyl-5,6,7,8-tetrahydroimidazo[1,2-a]pyrazine-2-carboxamide (L003-5)

3-(4-Fluoro-2-(trifluoromethyl)benzyl)-N-methyl-5,6,7,8-tetrahydroimidazo[1,2-a]pyrazine-2-carboxamide hydrochloride (70 mg, 0.175 mmol), 4,5-dichloro-2-(tetrahydro-2H-pyran-2-yl)pyridazin-3(2H)-one (50 mg, 0.192 mmol), and N,N-diisopropylethanamine (68 mg, 0.525 mmol) were dissolved in n-butanol (1 mL), and the reaction mixture was stirred at 120° C. for 4 hours. After the reaction was completed, the reaction mixture was evaporated to dryness by rotary evaporation, and then the crude product was purified by a silica gel thin-layer preparative plate (mobile phase: ethyl acetate) to obtain 60 mg of a white solid with a yield of 59%. LC-MS $[M+H]^+$=569.

3.6 Preparation of Compound 7-(5-chloro-6-oxo-1,6-dihydropyridazin-4-yl)-3-(4-fluoro-2-(trifluoromethyl)benzyl)-N-methyl-5,6,7,8-tetrahydroimidazo[1,2-a]pyrazine-2-carboxamide (L003)

7-(5-Chloro-6-oxo-1-(tetrahydro-2H-pyran-2-yl)-1,6-dihydropyridazin-4-yl)-3-(4-fluoro-2-(trifluoromethyl)benzyl)-N-methyl-5,6,7,8-tetrahydroimidazo[1,2-a]pyrazine-2-carboxamide (60 mg, 0.11 mmol) was dissolved in dichloromethane (2 mL), and a solution of hydrogen chloride in 1,4-dioxane (2 mL, 4 M) was added thereto, and the reaction mixture was stirred at room temperature for 1 hour. The reaction mixture was evaporated to dryness by rotary evaporation, then the crude product was redissolved in methanol/dichloromethane solution (10 mL, 1/15), and solid sodium bicarbonate was added thereto. The mixture was stirred for 5 minutes, filtered, and the filtrate was concentrated under reduced pressure, and then the crude product was purified by a preparative plate (methanol/dichloromethane=1/20) to obtain 30 mg of a white solid with a yield of 59%.

LC-MS $[M+H]^+$=485. $^1$H NMR (400 MHz, MeOD): δ 7.94 (s, 1H), 7.51 (dd, J=9.1, 2.8 Hz, 1H), 7.25 (t, J=8.5 Hz, 1H), 6.96 (dd, J=8.6, 5.2 Hz, 1H), 4.75 (s, 2H), 4.67 (s, 2H), 3.87 (d, J=5.0 Hz, 2H), 3.83 (d, J=5.0 Hz, 2H), 2.87 (s, 3H).

Example 4: Preparation of Compound 4-chloro-5-(3-((4-fluoro-2-(trifluoromethyl)phenyl)amino)-5,6-dihydroimidazo[1,2-a]pyrazin-7(8H)-yl)pyridazin-3(2H)-one (L004)

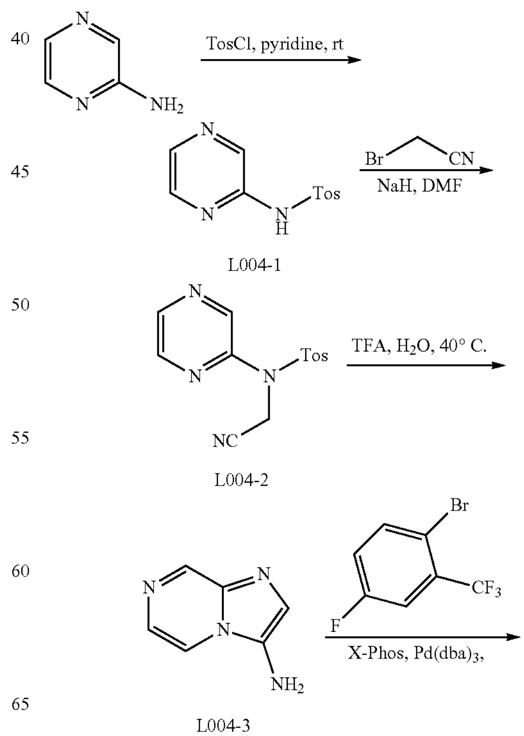

L004-1

L004-2

L004-3

-continued

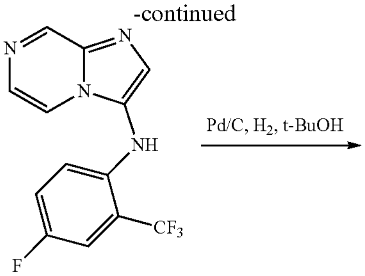

L004-4

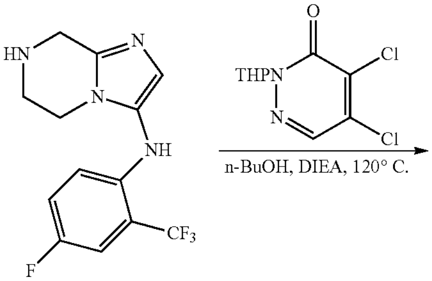

L004-5

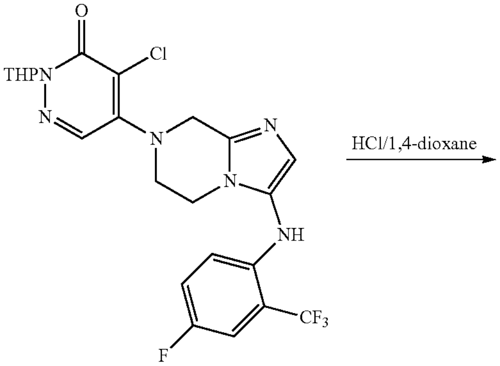

L004-6

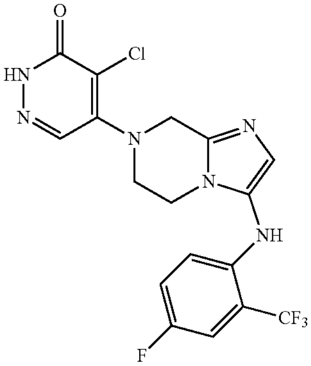

L004

4.1 Preparation of Compound 4-methyl-N-(pyrazin-2-yl)benzenesulfonamide (L004-1)

To pyridine (100 mL) was added pyrazin-2-amine (6.4 g, 67.30 mmol) at room temperature, and added p-toluenesulfonyl chloride (15.4 g, 8.07 mmol), and the reaction mixture was stirred at room temperature for 18 hours. The reaction mixture was concentrated under reduced pressure, washed with methanol (30 mL) and filtered to obtain 6.80 g of 4-methyl-N-(pyrazin-2-yl)benzenesulfonamide as a gray solid with a yield of 36%. LC-MS $[M+H]^+$=249.9.

4.2 Preparation of Compound N-(cyanomethyl)-4-methyl-N-(pyrazin-2-yl)benzenesulfonamide (L004-2)

To DMF (30 mL) was added 4-methyl-N-(pyrazin-2-yl) benzenesulfonamide (6.8 g, 27.20 mmol), and added sodium hydride (1.6 g, 40.80 mmol, 60%), and then the reaction mixture was stirred for 30 minutes at room temperature, then bromoacetonitrile (4.9 g, 40.80 mmol) was added thereto and the reaction mixture was continued to stir for 30 minutes and then heated to 60° C. and reacted for 3 hours. After returning to room temperature, the reaction mixture was continued to stir for 14 hours. The reaction mixture was poured into saturated ammonium chloride (200 mL), extracted with ethyl acetate (3*50 mL), dried over anhydrous sodium sulfate, filtered, and the filtrate was concentrated. The crude product was purified by silica gel column chromatography (ethyl acetate) to obtain N-(cyanomethyl)-4-methyl-N-(pyrazin-2-yl)benzenesulfonamide (3.5 g, yield of 45%) as a brown solid. LC-MS $[M+H]^+$=288.9.

4.3 Preparation of Compound imidazo[1,2-a]pyrazin-3-amine (L004-3)

N-(Cyanomethyl)-4-methyl-N-(pyrazin-2-yl)benzenesulfonamide (1.8 g, 6.20 mmol) was added to a mixed solvent of trifluoroacetic acid (9.0 mL) and water (1.0 mL), and the reaction mixture was heated to 40° C. and reacted for 2.5 hours. The reaction mixture was concentrated under reduced pressure, and the concentrated solid was added to saturated sodium acetate (40 mL), and then the mixture was stirred for 1 hour, extracted with ethyl acetate (30 mL*6). The organic phases were combined, concentrated under reduced pressure to dryness, and the crude product was purified by silica gel column chromatography (dichloromethane:methanol=10:1) to obtain 0.5 g of imidazo[1,2-a]pyrazin-3-amine as a yellow solid with a yield of 60%. LC-MS $[M+H]^+$=315.1.

4.4 Preparation of Compound N-(4-fluoro-2-(trifluoromethyl)phenyl)imidazo[1,2-a]pyrazin-3-amine (L004-4)

To 1,4-dioxane (20 mL) was added imidazo[1,2-a] pyrazin-3-amine (400 mg, 2.98 mmol), 1-bromo-4-fluoro-2-(trifluoromethyl)benzene (1.45 g, 5.96 mmol), 2-dicyclohexylphosphino-2',4',6'-triisopropylbiphenyl (142 mg, 0.30 mmol), and $Cs_2CO_3$ (1.94 g, 5.96 mmol) under nitrogen atmosphere, and added tris(dibenzylideneacetone)dipalladium (273 mg, 0.30 mmol), and then the reaction mixture was heated to 120° C. and stirred for 15 hours. The reaction mixture was cooled to room temperature, quenched by adding 30 mL of water, extracted with ethyl acetate (20 mL*3). The organic phases were combined, washed with saturated brine (20 mL), dried over anhydrous sodium sulfate, filtered, and the filtrate was concentrated under reduced pressure. The crude product was purified by silica gel column chromatography (ethyl acetate) to obtain 250 mg of N-(4-fluoro-2-(trifluoromethyl)phenyl)imidazo[1,2-a] pyrazin-3-amine as a brown solid with a yield of 23%.

LC-MS $[M+H]^+$=296.9.

4.5 Preparation of Compound N-(4-fluoro-2-(trifluoromethyl)phenyl)-5,6,7,8-tetrahydroimidazo[1,2-a]pyrazin-3-amine (L004-5)

N-(4-Fluoro-2-(trifluoromethyl)phenyl)imidazo[1,2-a]pyrazin-3-amine (150 mg, 0.50 mmol) was dissolved in t-BuOH (40 mL), and Pd/C (10%, 50 mg) was added thereto, and then the reaction mixture was stirred under hydrogen atmosphere for 72 hours, filtered, and the filtrate was concentrated to obtain 150 mg of N-(4-fluoro-2-(trifluoromethyl)phenyl)-5,6,7,8-tetrahydroimidazo[1,2-a]pyrazin-3-amine as a brown solid (crude product). LC-MS $[M+H]^+$=300.9

4.6 Preparation of Compound 4-chloro-5-(3-((4-fluoro-2-(trifluoromethyl)phenyl)amino)-5,6-dihydroimidazo[1,2-a]pyrazin-7(8H)-yl)-2-(tetrahydro-2H-pyran-2-yl)pyridazin-3(2H)-one (L004-6)

N-(4-Fluoro-2-(trifluoromethyl)phenyl)-5,6,7,8-tetrahydroimidazo[1,2-a]pyrazin-3-amine (140 mg, 0.46 mmol) and 4,5-dichloro-2-(tetrahydro-2H-pyran-2-yl)pyridazin-3(2H)-one (172 mg, 0.68 mmol) were dissolved in n-BuOH (0.7 mL), and DIEA (178 mg, 1.40 mmol) was added thereto, then the reaction mixture was heated to 120° C. and reacted for 3 hours.

The reaction mixture was cooled to room temperature, concentrated under reduced pressure, and the residue was purified by a silica gel thin-layer preparative plate (ethyl acetate) to obtain 50 mg of 4-chloro-5-(3-((4-fluoro-2-(trifluoromethyl)phenyl)amino)-5,6-dihydroimidazo[1,2-a]pyrazin-7(8H)-yl)-2-(tetrahydro-2H-pyran-2-yl)pyridazin-3(2H)-one as a brown solid with a yield of 21%. LC-MS $[M+H]^+$=512.8.

4.7 Preparation of Compound 4-chloro-5-(3-((4-fluoro-2-(trifluoromethyl)phenyl)amino)-5,6-dihydroimidazo[1,2-a]pyrazin-7(8H)-yl)pyridazin-3(2H)-one (L004)

To DCM (3 mL) was added 4-chloro-5-(3-((4-fluoro-2-(trifluoromethyl)phenyl)amino)-5,6-dihydroimidazo[1,2-a]pyrazin-7(8H)-yl)-2-(tetrahydro-2H-pyran-2-yl)pyridazin-3(2H)-one (50 mg, 0.06 mmol) at room temperature, and added a solution of HCl in 1,4-dioxane (4 M, 1 N), and the reaction mixture was stirred for 3 hours. The reaction mixture was concentrated under reduced pressure, and the residue was dissolved in dichloromethane (30 mL), washed with saturated sodium bicarbonate (10 mL), dried over anhydrous sodium sulfate, filtered, and the filtrate was concentrated under reduced pressure. The crude product was purified by preparative chromatography to obtain 12.5 mg of 4-chloro-5-(3-((4-fluoro-2-(trifluoromethyl)phenyl)amino)-5,6-dihydroimidazo[1,2-a]pyrazin-7(8H)-yl)pyridazin-3(2H)-one as a white solid with a yield of 47%.

LC-MS $[M+H]^+$=428.8. $^1H$ NMR (400 MHz, DMSO-$d_6$) 13.04 (s, 1H), 7.96 (s, 1H), 7.42 (dd, J=8.9, 2.8 Hz, 1H), 7.29 (d, J=10.8 Hz, 2H), 6.83 (s, 1H), 6.60 (dd, J=9.1, 4.6 Hz, 1H), 4.65 (s, 2H), 3.78 (d, J=5.4 Hz, 4H).

Example 5: Preparation of Compound 5-(2-bromo-3-(4-fluoro-2-(trifluoromethyl)benzyl)-5,6-dihydroimidazo[1,2-a]pyrazin-7(8H)-yl)-4-chloropyridazin-3(2H)-one (L005)

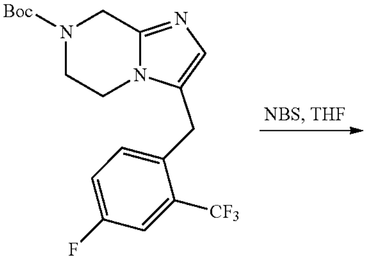

L002-6

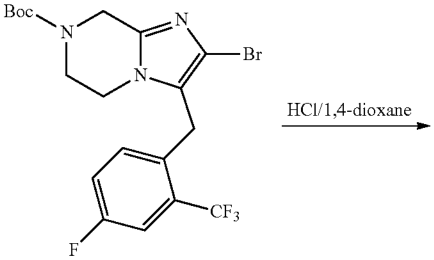

L005-1

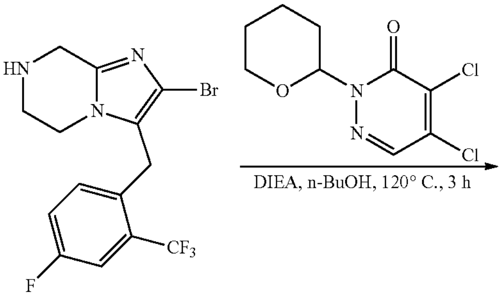

L005-2

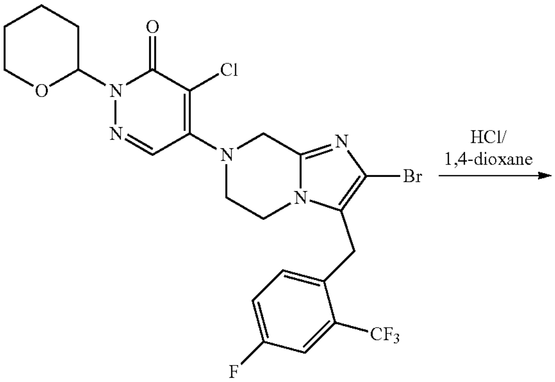

L005-3

-continued

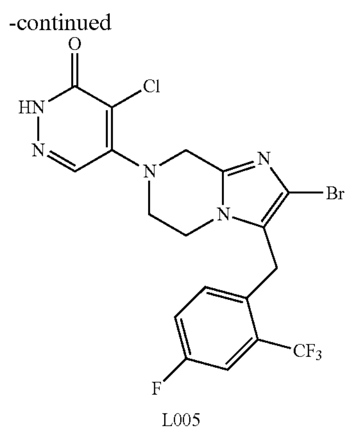

L005

5.1 Preparation of Compound tert-butyl 2-bromo-3-(4-fluoro-2-(trifluoromethyl)benzyl)-5,6-dihydroimidazo[1,2-a]pyrazine-7(8H)-carboxylate (L005-1)

tert-Butyl 3-(4-fluoro-2-(trifluoromethyl)benzyl)-5,6-dihydroimidazo[1,2-a]pyrazine-7(8H)-carboxylate (L002-6) (800 mg, 1.92 mmol) was dissolved in tetrahydrofuran (10 mL), and N-bromosuccinimide (513 mg, 2.88 mmol) was added thereto in batches at −70° C. under nitrogen atmosphere, and the mixture was stirred at −70° C. for 1 hour. After the reaction was completed, the mixture was quenched with water (20 mL), extracted with ethyl acetate (20 mL*4). The organic phases were combined, washed with saturated brine (10 mL*2), dried over anhydrous sodium sulfate, filtered, and the filtrate was concentrated under reduced pressure. The crude product was separated by silica gel column chromatography (DCM/EA=8/1) to obtain 300 mg of a yellow solid. The yield was 32%, LC-MS $[M+H]^+$=478.5.

5.2 Preparation of Compound 2-bromo-3-(4-fluoro-2-(trifluoromethyl)benzyl)-5,6,7,8-tetrahydroimidazo[1,2-a]pyrazine (L005-2) hydrochloride tert-Butyl 2-bromo-3-(4-fluoro-2-(trifluoromethyl)benzyl)-5,6-dihydroimidazo[1,2-a]pyrazine-7(8H)-carboxylate (300 mg, 0.63 mmol) was dissolved in a solution of HCl in 1,4-dioxane (3 mL, 4 mol/L), and the reaction mixture was stirred at 25° C. for 2 hours. After the reaction was completed, the reaction mixture was concentrated under reduced pressure to obtain 260 mg of a light yellow solid as a crude product. LC-MS $[M+H]^+$=377.8.

5.3 Preparation of Compound 5-(2-bromo-3-(4-fluoro-2-(trifluoromethyl)benzyl)-5,6-dihydroimidazo[1,2-a]pyrazin-7(8H)-yl)-4-chloro-2-(tetrahydro-2H-pyran-2-yl)pyridazin-3(2H)-one (L005-3)

2-Bromo-3-(4-fluoro-2-(trifluoromethyl)benzyl)-5,6,7,8-tetrahydroimidazo[1,2-a]pyrazine hydrochloride (207 mg, 0.50 mmol) was dissolved in n-butanol (1 mL), and then 4,5-dichloro-2-(tetrahydro-2H-pyran-2-yl)pyridazin-3(2H)-one (187 mg, 0.70 mmol) and N,N-diisopropylethanamine (256 mg, 2.00 mmol) were added thereto, and the reaction mixture was stirred at 120° C. for 3 hours under nitrogen atmosphere. After the reaction was completed, the reaction mixture was concentrated under reduced pressure. The crude product was separated by silica gel column chromatography (DCM/MeOH=30/1) to obtain 200 mg of a yellow solid with a yield of 67%, LC-MS $[M+H]^+$=590.4.

5.4 Preparation of Compound 5-(2-bromo-3-(4-fluoro-2-(trifluoromethyl)benzyl)-5,6-dihydroimidazo[1,2-a]pyrazin-7(8H)-yl)-4-chloropyridazin-3(2H)-one (L005)

5-(2-Bromo-3-(4-fluoro-2-(trifluoromethyl)benzyl)-5,6-dihydroimidazo[1,2-a]pyrazin-7(8H)-yl)-4-chloro-2-(tetrahydro-2H-pyran-2-yl)pyridazin-3(2H)-one (150 mg, 0.25 mmol) was dissolved in a solution of HCl in 1,4-dioxane (2 mL, 4 mol/L), and the reaction mixture was stirred at 25° C. for 1 hour. After the reaction mixture was concentrated under reduced pressure, saturated sodium bicarbonate solution (25 mL) was added thereto, and the mixture was extracted with ethyl acetate (20 mL*3). The organic phase was dried over anhydrous sodium sulfate, filtered, and the filtrate was concentrated under reduced pressure. The crude product was recrystallized twice with ethyl acetate to obtain 33.8 mg of a white solid with a yield of 25%. LC-MS $[M+H]^+$=505.7.

$^1$H NMR (400 MHz, DMSO-$d_6$) δ 13.05 (s, 1H), 7.94 (s, 1H), 7.68 (dd, J=9.2, 2.7 Hz, 1H), 7.48 (td, J=8.4, 2.6 Hz, 1H), 7.01 (dd, J=8.7, 5.5 Hz, 1H), 4.66 (s, 2H), 4.10 (s, 2H), 3.86-3.77 (m, 4H).

Example 6: Preparation of Compound 4-chloro-5-(3-(4-fluoro-2-(trifluoromethyl)benzyl)-5,6,8,9-tetrahydro-7H-imidazo[1,2-d][1,4]diazepin-7-yl)pyridazin-3(2H)-one (L006)

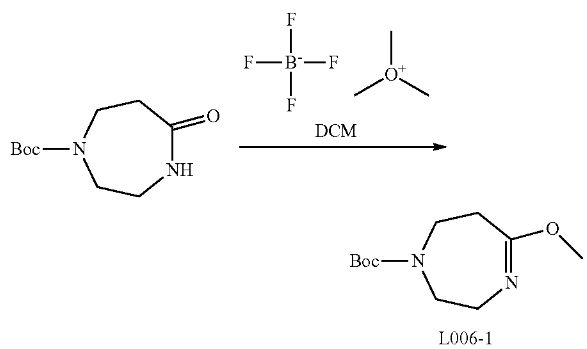

L006-1

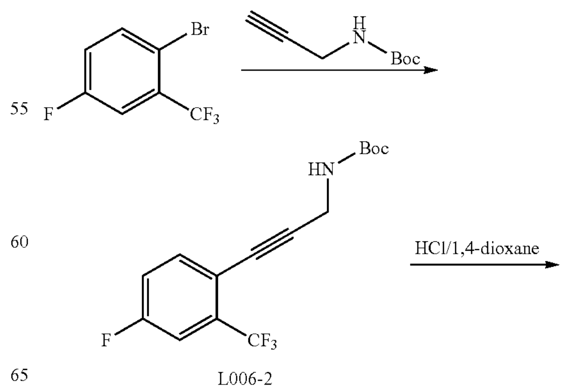

L006-2

-continued

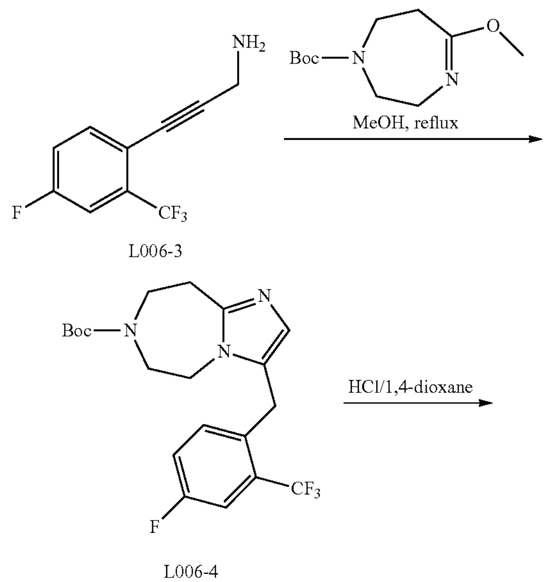

L006-3

L006-4

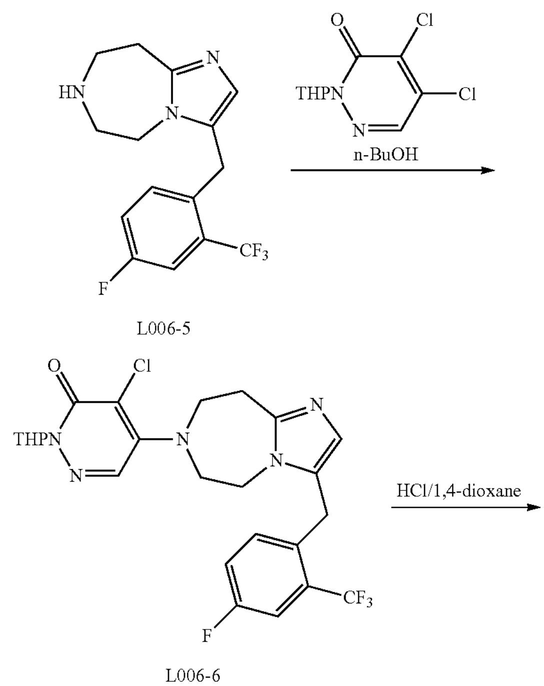

L006-5

L006-6

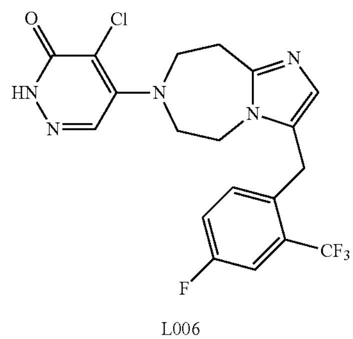 [SMILES: O=c1[nH]ncc(N2CCc3ncc(Cc4ccc(F)cc4C(F)(F)F)n3CC2)c1Cl]

L006

6.1 Preparation of Compound tert-butyl 5-methoxy-2,3,6,7-tetrahydro-1H-1,4-diazepine-1-carboxylate (L006-1)

1-Boc-1,4-diaza-5-cycloheptanone (500 mg, 2.32 mmol) was dissolved in dichloromethane (5 mL), and trimethyloxonium tetrafluoroborate (377 mg, 2.552 mmol) was added thereto at 0° C., and the reaction mixture was stirred at 25° C. for 14 hours under nitrogen atmosphere. After the reaction was completed, saturated sodium bicarbonate solution (15 mL) was added thereto, and the mixture was extracted with ethyl acetate (20 mL×2). The organic phases were combined, washed with water (20 mL×2), dried over anhydrous sodium sulfate, filtered, and the filtrate was concentrated to obtain 400 mg of a crude product with a yield of 67.6%, which was used directly in the next reaction step without purification.

$^1$H NMR (300 MHz, $CDCl_3$) δ 3.60 (s, 3H), 3.53-3.49 (m, 6H), 2.57-2.56 (m, 2H), 1.46 (s, 9H).

6.2 Preparation of Compound tert-butyl (3-(4-fluoro-2-(trifluoromethyl)phenyl)prop-2-yn-1-yl) carbamate (L006-2)

2-Bromo-5-fluorobenzotrifluoride (2.00 g, 8.2 mmol) was dissolved in 1,4-dioxane (20 mL), and N-Boc-aminopropyne (4.66 g, 32.8 mmol), cuprous iodide (15 mg, 0.082 mmol), diisopropylamine (960 mg, 9.51 mmol), bis(triphenylphosphine)palladium(II) chloride (230 mg, 0.33 mmol), and a solution of 10% tri-tert-butylphosphine in n-hexane (960 mg, 0.48 mmol) were added thereto. The reaction mixture was stirred at 45° C. for 15 hours under nitrogen atmosphere. After the reaction was completed, the reaction mixture was evaporated to dryness by rotary evaporation to remove the solvent, and the crude product was separated by silica gel column chromatography (PE/EA=10/1) to obtain 1.2 g of a light yellow solid containing impurity N-Boc-aminopropyne (which could be removed in the next step) with a purity of about 30% and a yield of 14.6%. LC-MS $[M+H]^+$=261.9.

6.3 Preparation of Compound 3-(4-fluoro-2-(trifluoromethyl)phenyl)prop-2-yn-1-amine (L006-3)

tert-Butyl (3-(4-fluoro-2-(trifluoromethyl)phenyl)prop-2-yn-1-yl)carbamate (1.2 g, 1.1 mmol) was dissolved in dichloromethane (8 mL), and a solution of HCl in 1,4-dioxane (4 M, 4.5 mL) was added thereto at 0° C., and the reaction mixture was stirred for 15 hours at 25° C. under nitrogen atmosphere. After the reaction was completed, the reaction mixture was evaporated to dryness by rotary evaporation to remove the solvent to obtain a crude product. To the crude product was added saturated sodium bicarbonate solution (10 mL), and the mixture was extracted with ethyl acetate (10 mL×2). The organic phases were combined, dried over anhydrous sodium sulfate, filtered, and then the filtrate was concentrated to obtain 0.2 g of a light yellow liquid with a yield of 72.7%. LC-MS $[M+H]^+$=218.0.

6.4 Preparation of Compound tert-butyl 3-(4-fluoro-2-(trifluoromethyl)benzyl)-5,6,8,9-tetrahydro-7H-imidazo[1,2-d][1,4]diazepine-7-carboxylate (L006-4)

3-(4-Fluoro-2-(trifluoromethyl)phenyl)prop-2-yn-1-amine (200 mg, 0.92 mmol) was dissolved in anhydrous methanol (4 mL), and tert-butyl 5-methoxy-2,3,6,7-tetrahydro-1H-1,4-diazepine-1-carboxylate (316 mg, 1.38 mmol) was added thereto, and the reaction mixture was stirred for 5 hours at 66° C. under nitrogen atmosphere. After the reaction was completed, the reaction mixture was evaporated to dryness by rotary evaporation to remove the solvent, and the crude product was separated by silica gel column chromatography (DCM/MeOH=50/1) to obtain 200 mg of a light yellow oil with a yield of 44.5%. LC-MS $[M+H]^+$ =414.0.

6.5 Preparation of Compound 3-(4-fluoro-2-(trifluoromethyl)benzyl)-6,7,8,9-tetrahydro-5H-imidazo[1,2-d][1,4]diazepine (L006-5)

tert-Butyl 3-(4-fluoro-2-(trifluoromethyl)benzyl)-5,6,8,9-tetrahydro-7H-imidazo[1,2-d][1,4]diazepine-7-carboxylate (200 mg, 0.48 mmol) was dissolved in DCM (3 mL), and a solution of HCl in 1,4-dioxane (4 M, 2 mL) was added thereto at 0° C., and the mixture was stirred for 15 hours at 25° C. under nitrogen atmosphere. The mixture was concentrated under reduced pressure to obtain 200 mg of a crude product, which was directly used in the next reaction step without purification.

LC-MS $[M+H]^+$=314.0.

6.6 Preparation of Compound 4-chloro-5-(3-(4-fluoro-2-(trifluoromethyl)benzyl)-5,6,8,9-tetrahydro-7H-imidazo[1,2-d][1,4]diazepin-7-yl)-2-(tetrahydro-2H-pyran-2-yl)pyridazin-3(2H)-one (L006-6)

The crude product 3-(4-fluoro-2-(trifluoromethyl)benzyl)-6,7,8,9-tetrahydro-5H-imidazo[1,2-d][1,4]diazepine (200 mg, 0.48 mmol) was dissolved in n-butanol (0.8 mL), and 4,5-dichloro-2-(tetrahydro-2H-pyran-2-yl)pyridazin-3(2H)-one (142 mg, 0.57 mmol) and N,N-diisopropylethanamine (186 mg, 1.44 mmol) were added thereto. The reaction mixture was stirred at 120° C. for 6 hours under nitrogen atmosphere. After the reaction was completed, the reaction mixture was evaporated to dryness by rotary evaporation to remove the solvent, and the crude product was separated by preparative TLC (DCM/MeOH=20/1) to obtain 75 mg of a yellow oil with a yield of 31.8%. LC-MS $[M+H]^+$=525.8.

6.7 Preparation of Compound 4-chloro-5-(3-(4-fluoro-2-(trifluoromethyl)benzyl)-5,6,8,9-tetrahydro-7H-imidazo[1,2-d][1,4]diazepin-7-yl)pyridazin-3(2H)-one (L006)

4-Chloro-5-(3-(4-fluoro-2-(trifluoromethyl)benzyl)-5,6,8,9-tetrahydro-7H-imidazo[1,2-d][1,4]diazepin-7-yl)-2-(tetrahydro-2H-pyran-2-yl)pyridazin-3(2H)-one (75 mg, 0.15 mmol) was dissolved in dichloromethane (2 mL), then a solution of HCl in 1,4-dioxane (4 M, 1 mL) was added thereto at 0° C., and the mixture was stirred at 25° C. for 4 hours under nitrogen atmosphere. The mixture was evaporated to dryness by rotary evaporation to remove the solvent, and the crude product was dissolved with a small amount of dichloromethane and methanol, and solid sodium bicarbonate was added to neutralize, then the mixture was filtered. The filtrate was concentrated under reduced pressure, and the crude product was separated by preparative TLC (DCM/MeOH=15/1) to obtain 25.5 mg of a light yellow solid with a yield of 37.9%. LC-MS $[M+H]^+$=441.9.

$^1H$ NMR (400 MHz, $CD_3OD$) δ 7.89 (s, 1H), 7.52 (dd, J=8.8, 2.4 Hz, 1H), 7.36-7.31 (m, 1H), 7.21 (dd, J=8.8, 5.2 Hz, 1H), 6.53 (s, 1H), 4.16-4.13 (m, 4H), 3.70-3.65 (m, 4H), 3.28-3.25 (m, 2H).

Examples 7 to 12

Referring to the preparation method of example 6, the following compounds were prepared:

| Example number | Compound number | Structural formula | LC-MS |
|---|---|---|---|
| 7 | L007 | 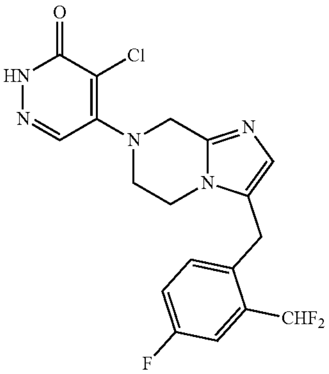 [SMILES: O=c1[nH]ncc(N2CCn3c(Cc4ccc(F)cc4C(F)F)cnc3C2)c1Cl] | 410.1 |
| 8 | L008 | 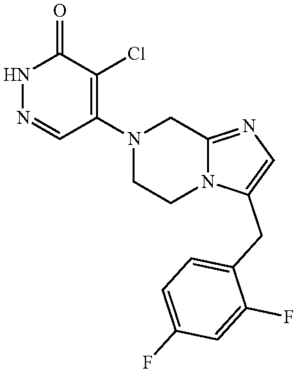 [SMILES: O=c1[nH]ncc(N2CCn3c(Cc4ccc(F)cc4F)cnc3C2)c1Cl] | 378.1 |
| 9 | L009 | 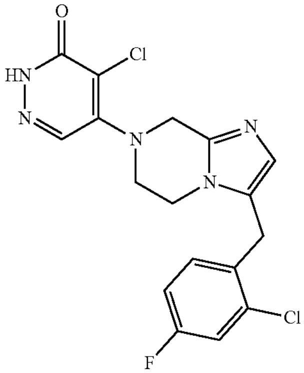 [SMILES: O=c1[nH]ncc(N2CCn3c(Cc4ccc(F)cc4Cl)cnc3C2)c1Cl] | 394.2 |

-continued
| Example number | Compound number | Structural formula | LC-MS |
|---|---|---|---|
| 10 | L010 | 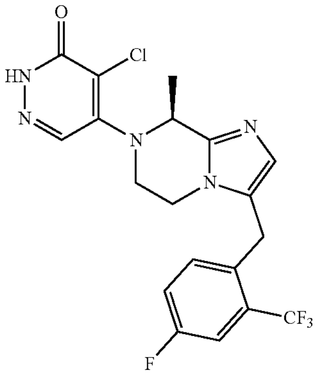 [SMILES: C[C@H]1c2ncc(Cc3ccc(F)cc3C(F)(F)F)n2CCN1c1cn[nH]c(=O)c1Cl] | 442.1 |
| 11 | L011 | 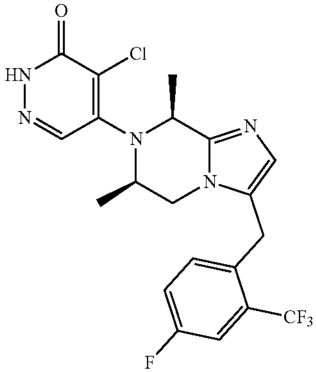 [SMILES: C[C@@H]1Cn2c(Cc3ccc(F)cc3C(F)(F)F)cnc2[C@H](C)N1c1cn[nH]c(=O)c1Cl] | 456.2 |
| 12 | L012 | 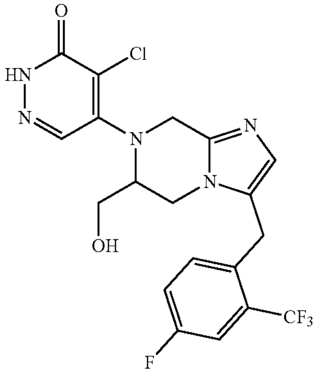 [SMILES: O=c1[nH]ncc(N2Cc3ncc(Cc4ccc(F)cc4C(F)(F)F)n3CC2CO)c1Cl] | 458.1 |
Example 13: Preparation of Compound 4-chloro-5-(3-(5-fluoro-2-(trifluoromethyl)benzyl)-5,6-dihydro-imidazol[1,2-a]pyrazin-7(8H)-yl)pyridazin-3(2H)-one (L013)
L013
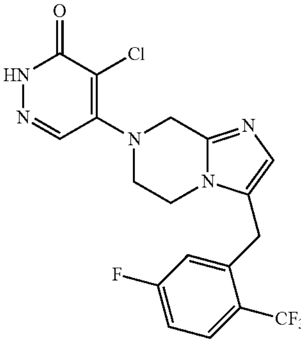
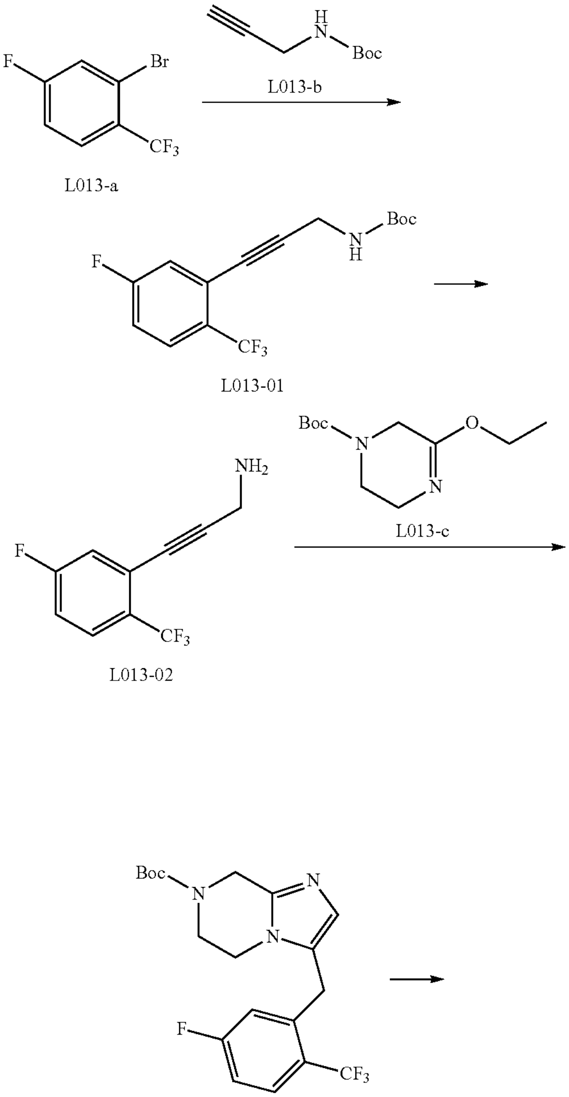

-continued

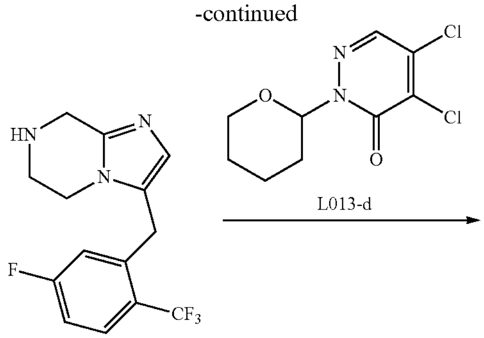

L013-d

L013-04

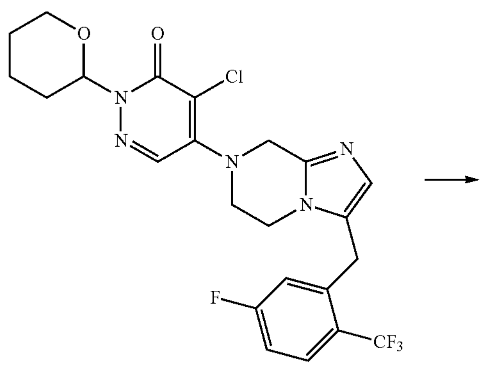

L013-05

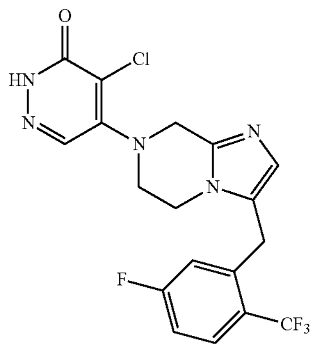

L013

13.1 Preparation of Compound L013-01

Compound L013-a (2.5 g, 10.2 mmol) was dissolved in 1,4-dioxane (25 mL), and compound L013-b (4.66 g, 32.8 mmol), bis(triphenylphosphine)palladium(II) chloride (230 mg, 0.328 mmol), cuprous iodide (15.6 mg, 0.082 mmol), triethylamine (962 mg, 9.512 mmol), and tri-tert-butylphosphine (10%, 1.20 g, 0.05 mmol) were added thereto. The mixture was stirred at 45° C. for 12 hours under nitrogen atmosphere. After the reaction was completed, water (20 mL) was added thereto, and the mixture was extracted with ethyl acetate (20 mL*3). The organic phase was washed with saturated brine (10 mL*2), dried over anhydrous sodium sulfate, and the crude product was separated by silica gel column chromatography (petroleum ether/ethyl acetate=10/1) to obtain 1.90 g of compound L013-01. LC-MS $[M-55]^+$=262.1.

13.2 Preparation of Compound L013-02

Compound L013-01 (1.90 g, 6.2 mmol) was dissolved in a solution of hydrogen chloride in 1,4-dioxane (10 mL, 4 mol/L). The mixture was stirred at 25° C. for 1 hour. After the reaction was completed, the pH of the mixture was adjusted to about 8 with sodium carbonate aqueous solution (20 mL), and the mixture was extracted with ethyl acetate (20 mL*3). The organic phase was washed with saturated brine (10 mL*2), dried over anhydrous sodium sulfate, and concentrated to obtain 450 mg of compound L013-02. LC-MS $[M+H]^+$=218.0.

13.3 Preparation of Compound L013-03

Compound L013-02 (450 mg, 2.06 mmol) was dissolved in anhydrous methanol (4.5 mL), and L013-c (567 mg, 2.48 mmol) was added thereto, and the mixture was stirred at 70° C. for 2 hours under nitrogen atmosphere. After the reaction was completed, the mixture was concentrated, and the crude product was separated by silica gel column chromatography (dichloromethane/methanol=100/1) to obtain 160 mg of compound L013-03. LC-MS $[M+H]^+$=399.8.

13.4 Preparation of Compound L013-04

Compound L013-03 (160 mg, 0.324 mmol) was dissolved in a solution of hydrogen chloride in 1,4-dioxane (4 mol/L, 2 mL). The mixture was stirred at 25° C. for 1 hour. After the reaction was completed, the pH of the mixture was adjusted to about 8 with sodium carbonate aqueous solution (10 mL), and the mixture was extracted with ethyl acetate (20 mL*3). The organic phase was washed with saturated brine (10 mL*2), dried over anhydrous sodium sulfate, and concentrated to obtain 100 mg of compound L013-04. LC-MS $[M+H]^+$=299.7.

13.5 Preparation of Compound L013-05

Compound L013-04 (100 mg, 0.33 mmol) was dissolved in n-butanol (0.5 mL), then N,N-diisopropylethylamine (129 mg, 0.1 mmol) and compound L013-d (100 mg, 0.40 mmol 1) were added thereto. The mixture was stirred at 120° C. for 3 hours under nitrogen atmosphere. After the reaction was completed, the reaction mixture was concentrated, and the crude product was separated by silica gel column chromatography (dichloromethane/methanol=30/1) to obtain 60 mg of compound L013-05. LC-MS $[M+H]^+$=512.1.

13.6 Preparation of Compound 4-chloro-5-(3-(5-fluoro-2-(trifluoromethyl)benzyl)-5,6-dihydroimidazo[1,2-a]pyrazin-7(8H)-yl)pyridazin-3(2H)-one (L013)

Compound L013-05 (40 mg, 0.078 mmol) was dissolved in a solution of hydrogen chloride in 1,4-dioxane (4 mmol/L, 1 mL). The mixture was stirred at 25° C. for 1 hour. After the reaction was completed, the mixture was evaporated to dryness by rotary evaporation to remove the solvent, and the crude product was purified by preparative high performance liquid chromatography (acetonitrile-water (0.1% formic acid)) to obtain 15.8 mg of compound L013. LC-MS $[M+H]^+$=427.7. $^1H$ NMR (400 MHz, DMSO-$d_6$) δ 7.95 (s, 1H), 7.85 (dd, J=8.8, 5.6 Hz, 1H), 7.34 (t, J=6.8 Hz, 1H), 7.05 (d, J=9.5 Hz, 1H), 6.54 (s, 1H), 4.64 (s, 2H), 4.12 (s, 2H), 3.91 (d, J=5.1 Hz, 2H), 3.83 (d, J=5.0 Hz, 2H).

Example 14: Preparation of Compound 4-((7-(5-chloro-6-oxo-1,6-dihydropyridazin-4-yl)-5,6,7,8-tetrahydroimidazo[1,2-a]pyrazin-3-yl)methyl)-3-(trifluoromethyl)benzonitrile (L014)

L014

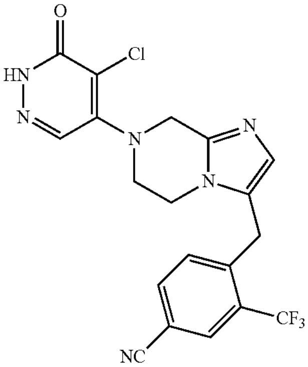

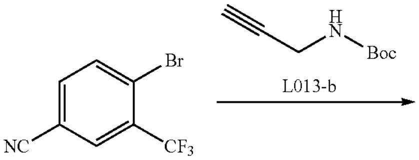

L014-a

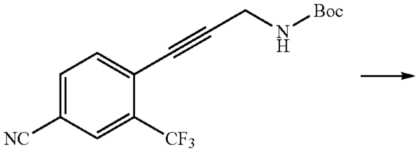

L014-01

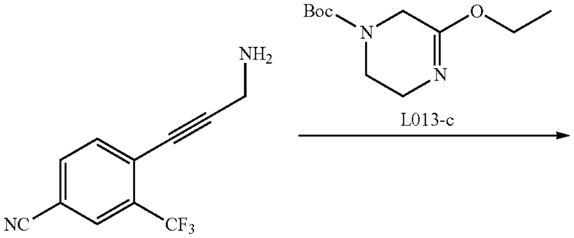

L014-02

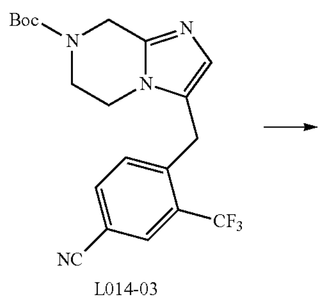

L014-03

-continued

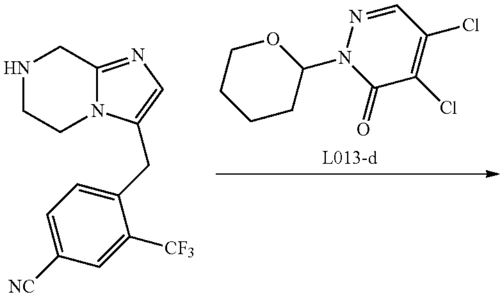

L014-04

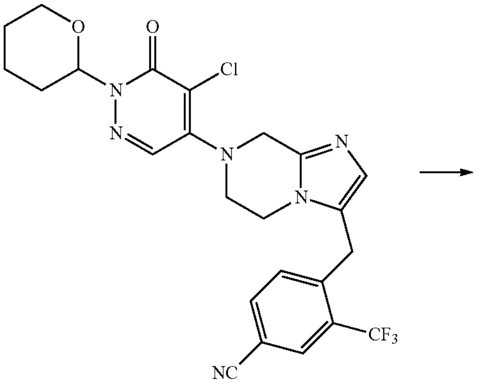

L014-05

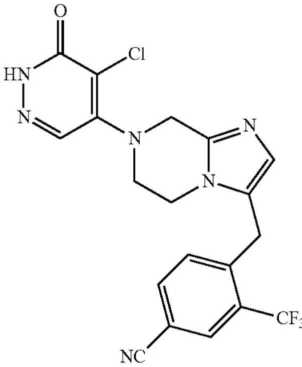

L014

14.1 Preparation of Compound L014-01

Compound L014-a (3.0 g, 12.0 mmol) was dissolved in 1,4-dioxane (30 mL), and compound L013-b (6.82 g, 48 mmol), bis(triphenylphosphine)palladium(II) chloride (340 mg, 0.04 mmol), cuprous iodide (20 mg, 0.01 mmol), triethylamine (1.41 g, 13.9 mmol), and tri-tert-butylphosphine (10%) (1.40 g, 0.06 mmol) were added thereto. The mixture was stirred at 45° C. for 12 hours under nitrogen atmosphere. After the reaction was completed, water (20 mL) was added thereto, and the mixture was extracted with ethyl acetate (20 mL*3). The organic phase was washed with saturated brine (10 mL*2), dried over anhydrous sodium sulfate, and the crude product was separated by silica gel column chromatography (petroleum ether/ethyl acetate=10:1) to obtain 4.0 g of compound L014-01.

LC-MS $[M-55]^+$=269.

14.2 Preparation of Compound L014-02

Compound L014-01 (1.90 g) was dissolved in a solution of hydrogen chloride in 1,4-dioxane (20 mL, 4 mol/L). The mixture was stirred at 25° C. for 1 hour. After the reaction was completed, the pH of the mixture was adjusted to about 8 with sodium carbonate aqueous solution (20 mL), and the mixture was extracted with ethyl acetate (20 mL*3). The organic phase was washed with saturated brine (10 mL*2), dried over anhydrous sodium sulfate, and concentrated to obtain 1.0 g of compound L014-02. LC-MS $[M+H]^+$=225.0.

14.3 Preparation of Compound L014-03

Compound L014-02 (1.0 g, 4.4 mmol) was dissolved in anhydrous methanol (10 mL), and compound L013-c (1.21 g, 5.28 mmol) was added thereto, and the mixture was stirred at 70° C. for 2 hours under nitrogen atmosphere. After the reaction was completed, the mixture was concentrated, and the crude product was separated by silica gel column chromatography (dichloromethane/methanol=100/1) to obtain 500 mg of compound L014-03. LC-MS $[M+H]^+$=407.2.

14.4 Preparation of Compound L014-04

Compound L014-03 (300 mg, 0.735 mmol) was dissolved in a solution of hydrogen chloride in 1,4-dioxane (4 mol/L, 3 mL). The mixture was stirred at 25° C. for 1 hour. After the reaction was completed, the pH of the mixture was adjusted to about 8 with sodium carbonate aqueous solution (20 mL), and the mixture was extracted with ethyl acetate (30 mL*3). The organic phase was washed with saturated brine (10 mL*2), dried over anhydrous sodium sulfate, and concentrated to obtain 200 mg of compound L014-04. LC-MS $[M+H]^+$=306.8.

14.5 Preparation of Compound L014-05

Compound L014-04 (100 mg, 0.325 mmol) was dissolved in n-butanol (0.5 mL), then N,N-diisopropylethylamine (126 mg, 0.976 mmol) and compound L013-d (97 mg, 0.390 mmol) were added thereto. The mixture was stirred at 120° C. for 3 hours under nitrogen atmosphere. After the reaction was completed, the mixture was concentrated, and the crude product was separated by silica gel column chromatography (dichloromethane/methanol=30/1) to obtain 50 mg of compound L014-05. LC-MS $[M+H]^+$=519.2.

14.6 Preparation of compound 4-((7-(5-chloro-6-oxo-1,6-dihydropyridazin-4-yl)-5,6,7,8-tetrahydroimidazo[1,2-a]pyrazin-3-yl)methyl)-3-(trifluoromethyl)benzonitrile (L014)

Compound L014-05 (50 mg, 0.10 mmol) was dissolved in a solution of hydrogen chloride in 1,4-dioxane (4 mol/L, 1 mL). The mixture was stirred at 25° C. for 1 hour. After the reaction was completed, the pH of the mixture was adjusted to about 8 with sodium carbonate aqueous solution (10 mL), and the mixture was extracted with ethyl acetate (10 mL*3). The organic phase was washed with saturated brine (10 mL*2), dried over anhydrous sodium sulfate, and concentrated. The crude product was washed with ethyl acetate and filtered to obtain 22 mg of compound L014. LC-MS $[M+H]^+$=435.1.

$^1$H NMR (400 MHz, DMSO-$d_6$) δ 7.95 (s, 1H), 7.48 (dd, J=8.8, 2.6 Hz, 1H), 7.27 (dd, J=8.6, 6.3 Hz, 1H), 7.20 (td, J=8.5, 2.6 Hz, 1H), 6.52 (s, 1H), 4.62 (s, 2H), 4.01 (s, 2H), 3.96 (t, J=5.2 Hz, 2H), 3.82 (t, J=5.2 Hz, 2H).

Example 15: Preparation of Compound 4-chloro-5-(3-(4-fluoro-2-(trifluoromethyl)benzoyl)-5,6-dihydroimidazo[1,2-a]pyrazin-7(8H)-yl)pyridazin-3(2H)-one (L015)

L015

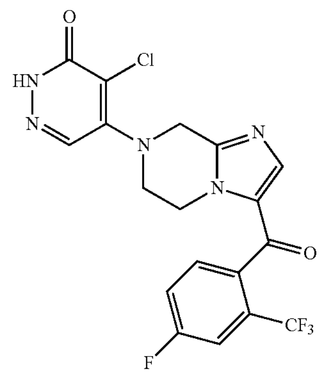

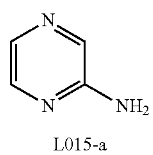

L015-a

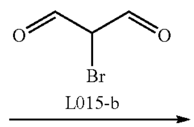

L015-b

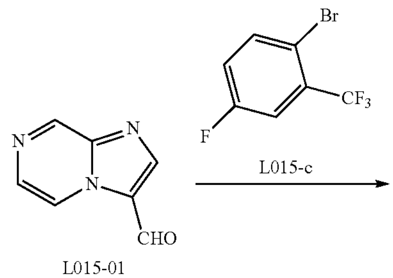

L015-c

L015-01

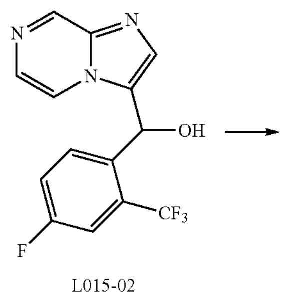

L015-02

-continued

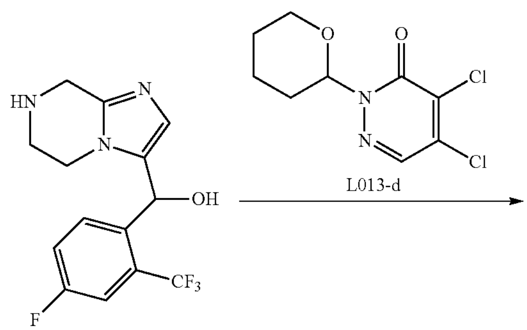

L015-03

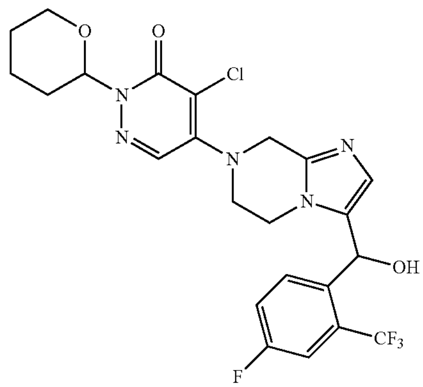

L015-04

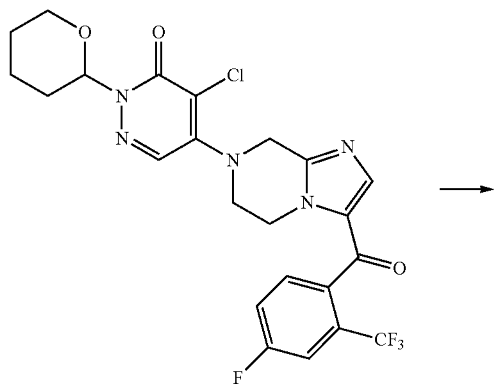

L015-05

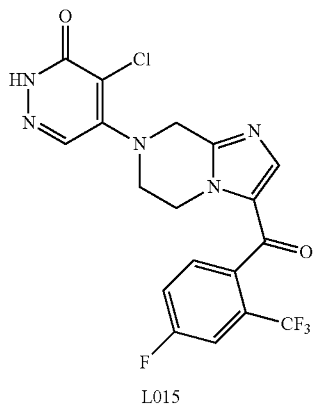

L015

15.1 Preparation of Compound L015-01

Compound L015-a (10.0 g, 0.11 mol) was dissolved in anhydrous ethanol (100 mL), and compound L015-b (15.8 g, 0.11 mmol) was added thereto, and the mixture was stirred at 90° C. for 2 hours. After the reaction was completed, the mixture was cooled to room temperature, and evaporated to dryness by rotary evaporation to remove the solvent to obtain a black viscous substance. 30 mL of a solution of hydrogen chloride (4 mol/L) in 1,4-dioxane was added thereto, and the mixture was stirred at 25° C. for 12 hours. After the reaction was completed, 50 mL of water was added thereto, and the pH of the mixture was adjusted to about 8 with sodium carbonate solution, and then the mixture was extracted with ethyl acetate (50 mL*4). The organic phase was washed with saturated brine (30 mL*2), dried over anhydrous sodium sulfate, evaporated to dryness by rotary evaporation to remove the solvent and then the residue was recrystallized with ethyl acetate for three times to obtain 3.5 g of compound L015-01. LC-MS $[M+H]^+$=148.0.

15.2 Preparation of Compound L015-02

Compound L015-c (7.47 g, 30.6 mmol) was dissolved in tetrahydrofuran (50 mL). To a mixture containing magnesium chips (1.47 g, 61.2 mmol) and iodine (50 mg, 2 mmol) in tetrahydrofuran (20 mL) was added 2 mL of the resulting solution dropwise under nitrogen atmosphere, and the reaction mixture was heated with a hair dryer until the solution was clear and transparent. To the reaction system was added the remaining solution of compound L015-c in tetrahydrofuran dropwise. The mixture was stirred at 70° C. for 1 hour, then cooled to room temperature. To the solution of compound L015-01 (3.00 g, 20.4 mmol) in tetrahydrofuran was added the mixture dropwise at −70° C. under nitrogen atmosphere. The mixed system was stirred at −70° C. for 2 hours. After the reaction was completed, ammonium chloride solution (50 mL) was added, and the mixture was extracted with ethyl acetate (50 mL*3). The organic phase was washed with saturated brine (30 mL*2), dried over anhydrous sodium sulfate, filtered, and the filtrate was concentrated, and then the crude product was separated by silica gel column chromatography (dichloromethane/methanol=100/1) to obtain 3.20 g of compound L015-02. LC-MS $[M+H]^+$=312.07.

15.3 Preparation of Compound L015-03

Compound L015-02 (1.10 g, 3.50 mmol) was dissolved in tetrahydrofuran (25 mL). Wet Pd/C (10%, 400 mg) was added thereto and the reaction mixture was stirred for 12 hours at room temperature under hydrogen atmosphere. After the reaction was completed, the reaction mixture was filtered and the filtrate was evaporated to dryness by rotary evaporation to remove the solvent to obtain 1.00 g of compound L015-03. LC-MS $[M+H]^+$=316.2.

15.4 Preparation of Compound L015-04

Compound L015-03 (200 mg, 0.63 mmol) was dissolved in anhydrous butanol (1 mL), and L013-d (189 mg, 0.76 mmol) and N,N-diisopropylethylamine (245 mg, 1.90 mmol) were added thereto, and the mixture was stirred at 120° C. for 2 hours under nitrogen atmosphere. The reaction mixture was concentrated, and the crude product was separated by silica gel column chromatography (dichloromethane/methanol=100/1) to obtain 160 mg of compound L015-04. LC-MS $[M+H]^+$=528.2.

15.5 Preparation of Compound L015-05

L015-04 (200 mg, 0.297 mmol) was dissolved in anhydrous dichloromethane (20 mL), then Dess-Martin periodinane (630 mg, 1.485 mmol) was added thereto. The mixture was stirred at 40° C. for 8 hours under nitrogen atmosphere. After the reaction was completed, the pH of the mixture was adjusted to about 9 with sodium hydroxide solution, and the mixture was extracted with dichloromethane (10 mL*3). The organic phase was dried over anhydrous sodium sulfate, filtered, and the filtrate was concentrated under reduced pressure. The crude product was separated by silica gel column chromatography (dichloromethane/methanol=100/1) to obtain 150 mg of compound L015-05. LC-MS $[M+H]^+$=526.2.

15.6 Preparation of Compound 4-chloro-5-(3-(4-fluoro-2-(trifluoromethyl)benzoyl)-5,6-dihydroimidazo[1,2-a]pyrazin-7(8H)-yl)pyridazin-3(2H)-one (L015)

L015-05 (150 mg, 0.28 mmol) was dissolved in a solution of hydrogen chloride in 1,4-dioxane (2 mL, 4 mol/L), and the mixture was stirred at 25° C. for 1 hour. After the reaction mixture was evaporated to dryness by rotary evaporation to remove the solvent to obtain a crude product, and the crude product was purified by preparative high performance liquid chromatography to obtain 21.6 mg of compound L015. LC-MS $[M+H]^+$=441.8.

$^1$H NMR (400 MHz, DMSO-$d_6$) δ 13.08 (s, 1H), 8.02 (s, 1H), 7.85 (dd, J=9.3, 2.5 Hz, 1H), 7.79 (dd, J=8.5, 5.5 Hz, 1H), 7.68 (td, J=8.5, 2.5 Hz, 1H), 7.35 (s, 1H), 4.83 (s, 2H), 4.52 (t, J=5.2 Hz, 2H), 3.91 (t, J=5.3 Hz, 2H).

Example 16: Preparation of Compound 4-chloro-5-(3-(2-(trifluoromethyl)benzoyl)-5,6-dihydroimidazo[1,2-a]pyrazin-7 (8H)-yl)pyridazin-3 (2H)-one (L016)

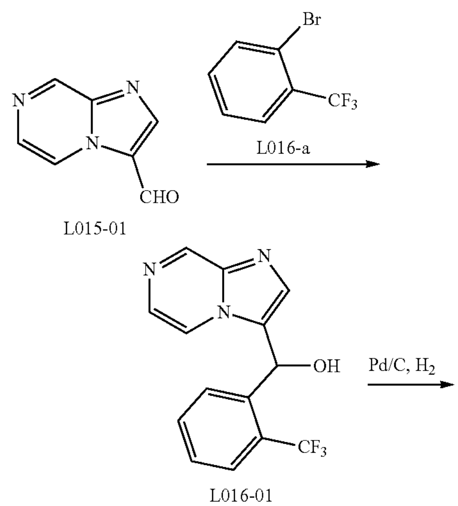

L015-01

L016-a

L016-01

-continued

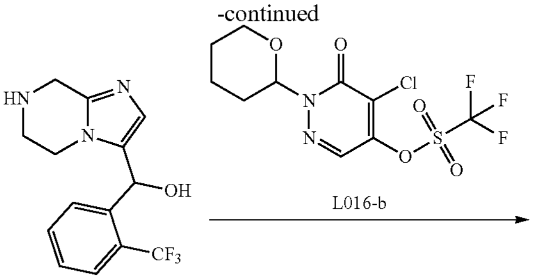

L016-02

L016-b

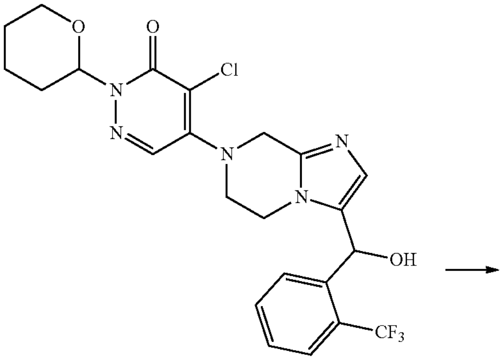

L016-03

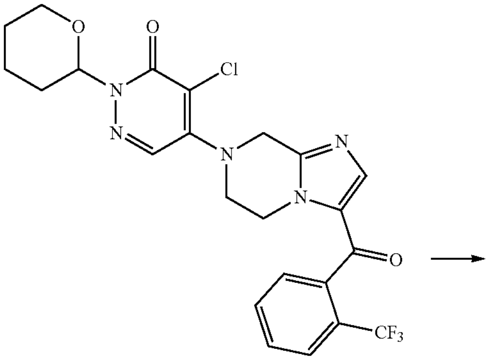

L016-04

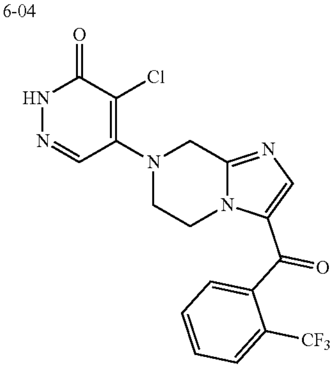

L016

16.1 Preparation of Compound L016-01

L016-a (2.55 g, 11.3 mmol) was dissolved in anhydrous tetrahydrofuran (40 mL), then the system was replaced with nitrogen for 3 times, and isopropyl magnesium bromide (2.8 M, 8.09 mL, 22.65 mmol) was added thereto at room temperature, and the reaction mixture was reacted for 2 hours. Then the reaction mixture was added with L015-01 (2.0 g, 13.6 mmol), heated to 60° C. and reacted for 2 hours.

After the reaction was completed, the reaction mixture was quenched with saturated sodium chloride aqueous solution (20 mL), and extracted with ethyl acetate (30 mL*3). The organic phases were combined, washed with saturated brine (50 mL), dried over anhydrous sodium sulfate, filtered, and the filtrate was concentrated under reduced pressure. The crude product was purified by a silica gel chromatography column (petroleum ether/ethyl acetate=3/1) to obtain 650 mg of compound L016-01. LC-MS $[M+H]^+$=294.0.

16.2 Preparation of Compound L016-02

Compound L016-01 (600 mg, 2.05 mmol) was dissolved in tetrahydrofuran (10 mL). Then palladium/carbon (10%, 60 mg) was added thereto, and the reaction mixture was reacted at 40° C. for 12 hours under hydrogen atmosphere, and the reaction was completed. The reaction mixture was filtered, and the filtrate was concentrated to obtain 540 mg of compound L016-02. LC-MS $[M+H]^+$=298.0.

16.3 Preparation of Compound L016-03

L016-02 (500 mg, 1.68 mmol), L016-b (915.05 mg, 2.52 mmol), and N,N-diisopropylethylamine (652 mg, 5.05 mol) were dissolved in dimethyl sulfoxide (10 mL), heated to 60° C. and reacted for 2 hours, and the reaction was completed. The reaction mixture was quenched with water (20 mL), extracted with ethyl acetate (30 mL*3). The organic phases were combined, washed with saturated brine (50 mL), dried over anhydrous sodium sulfate, and filtered. The filtrate was concentrated under reduced pressure and the crude product was purified by a silica gel chromatography column (petroleum ether/ethyl acetate=3/1) to obtain 510 mg of compound L016-03. LC-MS $[M+H]^+$=510.1.

16.4 Preparation of Compound L016-04

L016-03 (500 mg, 0.98 mmol) was dissolved in dichloromethane (10 mL). Dess-Martin periodinane (831.8 mg, 1.96 mmol) was added thereto in batches and the reaction mixture was stirred for 1 hour at room temperature. After the reaction was completed, the reaction mixture was filtered, and the filtrate was concentrated under reduced pressure. The crude product was purified by a silica gel chromatography column (petroleum ether/ethyl acetate=3/1) to obtain 210 mg of compound L016-04. LC-MS $[M+H]^+$=508.0.

16.5 Preparation of Compound 4-chloro-5-(3-(2-(trifluoromethyl)benzoyl)-5,6-dihydroimidazo[1,2-a]pyrazin-7(8H)-yl)pyridazin-3(2H)-one (L016)

L016-04 (200 mg, 0.39 mmol) was dissolved in a solution of hydrogen chloride in 1,4-dioxane (2 mL, 4 mol/L), and the mixture was stirred at 25° C. for 1 hour. After the reaction was completed, the mixture was evaporated to dryness by rotary evaporation to remove the solvent to obtain a crude product, and the crude product was purified by preparative high performance liquid chromatography to obtain 16.1 mg of compound L016.

LC-MS $[M+H]^+$=424.0;

$^1H$ NMR (400 MHz, DMSO-$d_6$) δ 13.05 (s, 1H), 8.00 (s, 1H), 7.90-7.86 (m, 1H), 7.82-7.74 (m, 2H), 7.67 (d, J=7.2 Hz, 1H), 7.25 (s, 1H), 4.81 (s, 2H), 4.51 (t, J=5.6 Hz, 2H), 3.92-3.88 (m, 2H).

Example 17: Preparation of Compound 4-chloro-5-(3-(4-chloro-2-(trifluoromethyl)benzoyl)-5,6-dihydroimidazo[1,2-a]pyrazin-7(8H)-yl)pyridazin-3(2H)-one (L017)

L017

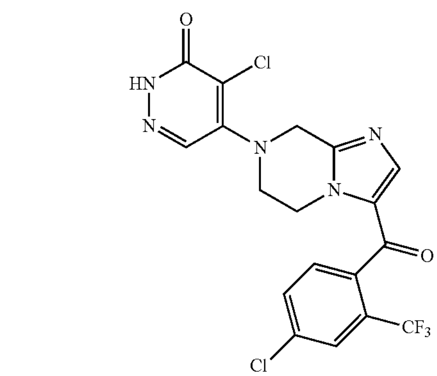

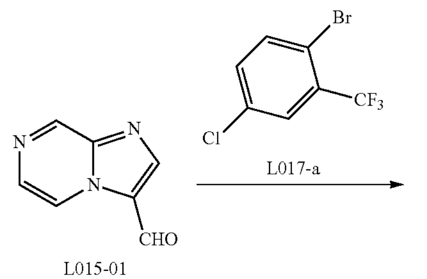

L017-a

L015-01

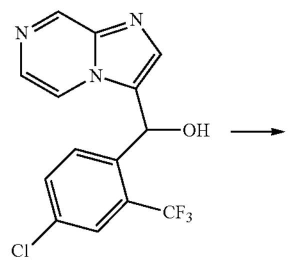

L017-01

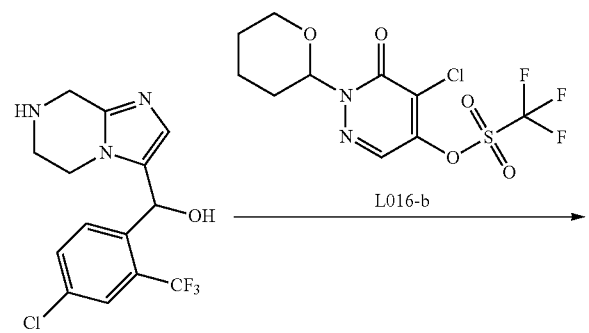

L016-b

L017-02

-continued

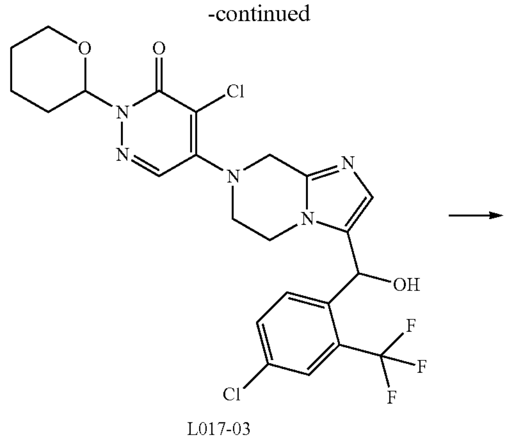

L017-03

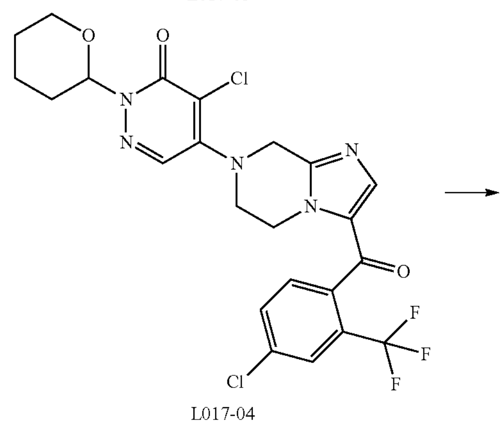

L017-04

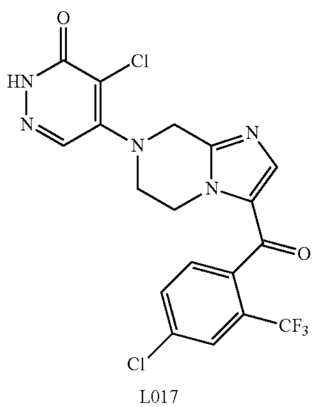 [SMILES: O=C(c1ccc(Cl)cc1C(F)(F)F)c1cnc2n1CCN(c1cn[nH]c(=O)c1Cl)C2]

L017

17.1 Preparation of Compound L017-01

To anhydrous tetrahydrofuran (80 mL) was added compound L017-a (4.36 g, 16.80 mmol), then the system was replaced with nitrogen for three times, and isopropyl magnesium bromide (2.8 M, 5 mL, 14.00 mmol) was slowly added dropwise thereto at room temperature. The reaction mixture was reacted at room temperature for 2 hours after the dropwise addition was completed. Then the reaction system was added with L015-01 (1.85 g, 12.60 mmol) solid, heated to 40° C. and reacted at this temperature for 4 hours, and then the reaction was completed. The reaction was quenched by adding saturated ammonium chloride aqueous solution (100 mL) slowly, and the mixture was extracted with dichloromethane (100 mL*3). The organic phase was washed with saturated brine (50 mL*3), dried over anhydrous sodium sulfate, filtered, and concentrated, and then the crude product was separated by silica gel column chromatography (dichloromethane/methanol=10/1) to obtain 2.5 g of compound L017-01. LC-MS $[M+H]^+$=328.0.

17.2 Preparation of Compound L017-02

Compound L017-01 (2.4 g, 7.32 mmol) was dissolved in tetrahydrofuran (30 mL), then palladium/carbon (10%, 1.0 g) was added thereto, and the system was replaced with nitrogen for three times, and the reaction mixture was reacted at 40° C. for 16 hours. After the reaction was completed, the reaction mixture was filtered, and the filtrate was concentrated to dryness, and the crude product was purified by silica gel column chromatography (dichloromethane/methanol=10/1) to obtain 1.0 g of compound L017-02. LC-MS $[M+H]^+$=332.0.

17.3 Preparation of Compound L017-03

Compound L017-02 (0.5 g, 1.06 mmol) and compound L016-b (0.54 g, 1.48 mmol) were weighed and dissolved in dimethyl sulfoxide (5.0 mL), and diisopropylethylamine (0.41 g, 3.17 mmol) was added thereto. The reaction mixture was stirred at 80° C. for 16 hours, and the reaction was completed. After the reaction mixture was cooled to 30° C., ethyl acetate (30 mL) and water (20 mL) were added thereto, and the mixture was stirred and the phases were separated. The aqueous phase was extracted with ethyl acetate (20 mL*2), and the organic phases were combined, washed with saturated brine (50 mL), dried over anhydrous sodium sulfate, and concentrated to obtain a crude product, which was purified by silica gel column chromatography (dichloromethane/methanol=10/1) to obtain 0.4 g of compound L017-03.

LC-MS $[M+H]^+$=544.0.

17.4 Preparation of Compound L017-04

Compound L017-03 (0.4 g, 734.81 mmol) was weighed and dissolved in dichloromethane (8.0 mL), and Dess-Martin periodinane (0.94 g, 2.2 mol) was added thereto, then the reaction mixture was stirred at room temperature for 16 hours. The reaction was completed. The reaction mixture was filtered, and the filtrate was concentrated, and the crude product was purified by silica gel column chromatography (dichloromethane/methanol=10/1) to obtain 0.35 g of compound L017-04.

LC-MS $[M+H]^+$=542.0.

17.5 Preparation of compound 4-chloro-5-(3-(4-chloro-2-(trifluoromethyl)benzoyl)-5,6-dihydroimidazo[1,2-a]pyrazin-7(8H)-yl)pyridazin-3(2H)-one (L017)

L017-04 (0.35 g, 645.35 μmol) was weighed into a reaction flask, and a solution of hydrogen chloride in 1,4-dioxane (4 M, 4 mL) was added thereto, and the reaction mixture was reacted at room temperature for 3 hours. The reaction was completed. The reaction mixture was concentrated, and the crude product was purified by preparative high performance liquid chromatography to obtain 42.8 mg of compound L017.

LC-MS $[M+H]^+$=458.0;

$^1$H NMR (400 MHz, DMSO-$d_6$) δ 13.06 (s, 1H), 8.01 (d, J=3.4 Hz, 2H), 7.90 (dd, J=8.2, 1.8 Hz, 1H), 7.74 (d, J=8.4 Hz, 1H), 7.37 (s, 1H), 4.83 (s, 2H), 4.51 (t, J=5.2 Hz, 2H), 3.91 (t, J=5.2 Hz, 2H), 2.07 (s, 1H).

Example 18: Preparation of Compound 4-chloro-5-(3-(5-fluoro-2-(trifluoromethyl)benzoyl)-5,6-dihydroimidazo[1,2-a]pyrazin-7(8H)-yl)pyridazin-3(2H)-one (L018A) and Compound 4-chloro-5-(3-(2-fluoro-5-(trifluoromethyl)benzoyl)-5,6-dihydroimidazo[1,2-a]pyrazin-7(8H)-yl)pyridazin-3(2H)-one (L018B)
L018A
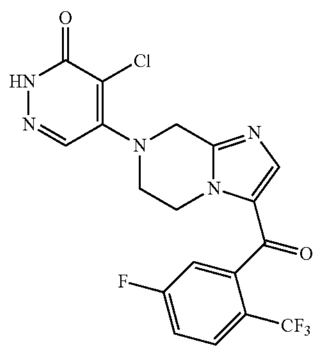
-continued
L018B
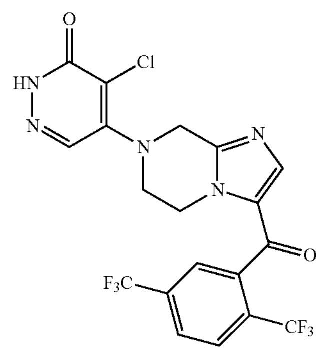
Synthesis Route:
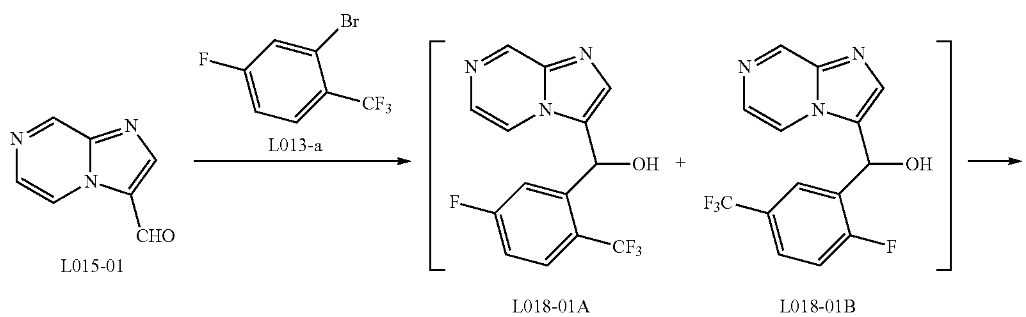
L015-01
L018-01A
L018-01B
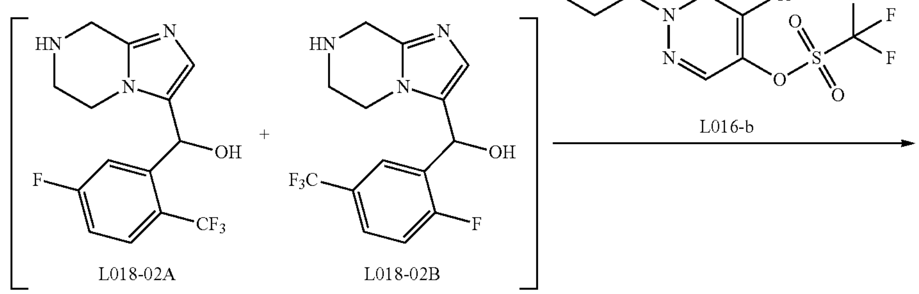
L018-02A
L018-02B -continued

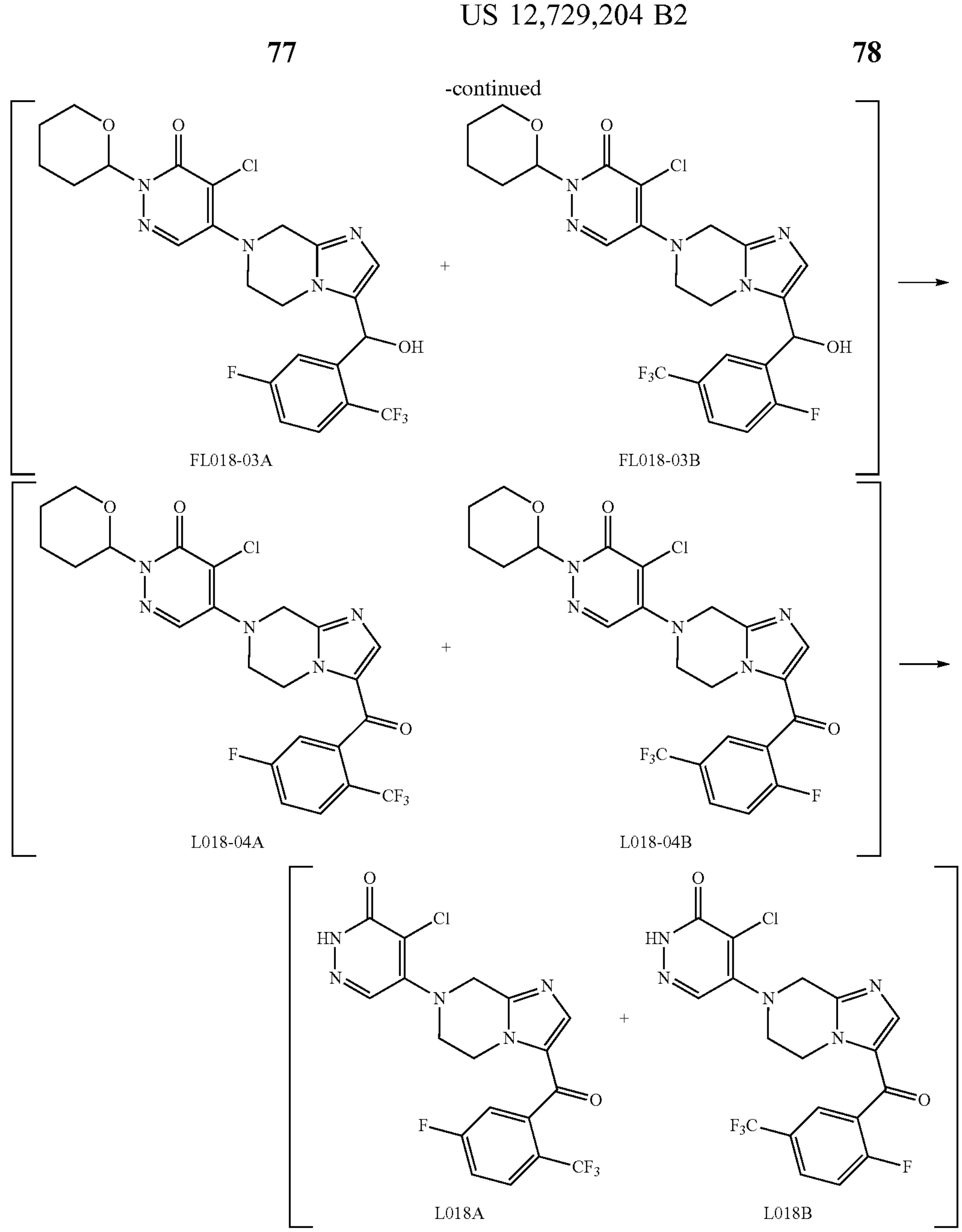

FL018-03A FL018-03B

L018-04A L018-04B

L018A L018B 18.1 Preparation of Compounds L018-01A & L018-01B

Compound L013-a (1 g, 4.11 mmol) was dissolved in tetrahydrofuran (15 mL). After the system was replaced with nitrogen, the mixture was cooled to −78° C. and added with a solution of 2.5M n-butyl lithium (1.8 mL, 4.52 mmol) in hexane, and the reaction mixture was reacted at −78° C. for 1 hour. Compound L015-01 (605 mg, 4.11 mmol) was added to the reaction system, and after the addition was completed, the reaction mixture was naturally warmed to room temperature and reacted overnight, then the reaction was completed. The reaction mixture was diluted by adding water (80 mL) slowly and extracted with ethyl acetate (30 mL*3). The organic phases were combined, washed with saturated brine (50 mL), dried over anhydrous sodium sulfate, filtered, and the filtrate was concentrated under reduced pressure to obtain a crude product. The crude product was purified by a silica gel chromatography column (dichloromethane/methanol=50/1 to 15/1) to obtain compounds L018-01A & L018-01B (600 mg). LC-MS $[M+H]^+$=312.0.

18.2 Preparation of Compounds L018-02A & L018-02B

Compounds L018-01A& L018-01B (270 mg, 0.87 mmol) were dissolved in methanol (20 mL), and anhydrous palladium/carbon (10%) was added thereto. After the system was replaced with nitrogen, the reaction was stirred at room temperature for 3 hours, and the reaction was completed. The reaction mixture was filtered, rinsed with methanol (3 mL) for three times, and the filtrate was concentrated under reduced pressure to obtain a product, which could be directly used in the next step without purification. Compounds L018-02A & L018-02B (230 mg) were obtained. LC-MS $[M+H]^+$=316.0.

18.3 Preparation of L018-03A & L018-03B

L018-02A & L018-02B (230 mg, 0.73 mmol) and L016-b (291 mg, 0.80 mmol) were dissolved in dimethyl sulfoxide (6 mL), and N,N-diisopropylethanamine (283 mg, 2.19 mmol) was added thereto. The reaction mixture was reacted at 60° C. overnight and the reaction was completed. The reaction mixture was poured into water (50 mL) and extracted with ethyl acetate (20 mL*3). The organic phases were combined, washed with saturated brine (50 mL), dried over anhydrous sodium sulfate, filtered, and the filtrate was concentrated under reduced pressure to obtain a crude product. The crude product was purified by a silica gel chromatography column (DCM/MeOH=50/1 to 20/1) to obtain L018-03A & L018-03B (270 mg).

LC-MS $[M+H]^+$=528.0.

18.4 Preparation of Compounds L018-04A & L018-04B

L018-03A & L018-03B (270 mg, 0.51 mmol) were dissolved in dichloromethane (10 mL), and Dess-Martin periodinane (434 mg, 1.02 mmol) was added thereto in batches at 0° C., and the reaction mixture was warmed to room temperature and reacted for 30 minutes. The reaction mixture was added with saturated sodium thiosulfate aqueous solution (30 mL) and extracted with dichloromethane (20 mL*3). The organic phases were combined, washed with saturated brine (50 mL), dried over anhydrous sodium sulfate, filtered, and the filtrate was concentrated under reduced pressure to obtain a crude product. The crude product was purified by a silica gel chromatography column (dichloromethane/methanol=50/1 to 20/1) to obtain L018-04A & L018-04B (230 mg). LC-MS $[M+H]^+$=526.0.

18.5 Preparation of Compound 4-chloro-5-(3-(5-fluoro-2-(trifluoromethyl)benzoyl)-5,6-dihydroimidazo[1,2-a]pyrazin-7(8H)-yl)pyridazin-3(2H)-one (L018A) and compound 4-chloro-5-(3-(2-fluoro-5-(trifluoromethyl)benzoyl)-5,6-dihydroimidazo[1,2-a]pyrazin-7(8H)-yl)pyridazin-3(2H)-one (L018B)

Compounds L018-04A & L018-04B (230 mg, 0.44 mmol) were placed in a 25 mL single-necked flask, and a solution of hydrogen chloride in 1,4-dioxane (4 M, 5 mL) was added thereto. The reaction mixture was stirred at room temperature for 30 minutes, and the reaction was completed. The reaction mixture was concentrated under reduced pressure to obtain a crude product, and the crude product was purified by a preparative high performance liquid chromatography column in a water/acetonitrile system to obtain compound L018A (26.8 mg) and compound L018B (37.0 mg) after lyophilization.

L018A: LC-MS $[M+H]^+$=442.0; $^1H$ NMR (400 MHz, DMSO-$d_6$) δ 13.07 (s, 1H), 8.01 (s, 1H), 7.98 (s, 1H), 7.62 (t, J=8.4 Hz, 2H), 7.41 (s, 1H), 4.83 (s, 2H), 4.51 (t, J=5.2 Hz, 2H), 3.91 (t, J=5.2 Hz, 2H).

L018B: LC-MS $[M+H]^+$=442.0 $^1H$ NMR (400 MHz, DMSO-$d_6$) δ 13.07 (s, 1H), 8.10-7.90 (m, 3H), 7.64 (t, J=9.2 Hz, 1H), 7.55 (s, 1H), 4.83 (s, 2H), 4.52 (t, J=4.8 Hz, 2H), 3.91 (t, J=4.8 Hz, 2H).

Example 19: Preparation of Compound 4-(7-(5-chloro-6-oxo-1,6-dihydropyridazin-4-yl)-5,6,7,8-tetrahydroimidazo[1,2-a]pyrazine-3-carbonyl)-3-(trifluoromethyl)benzonitrile (L019)

L019

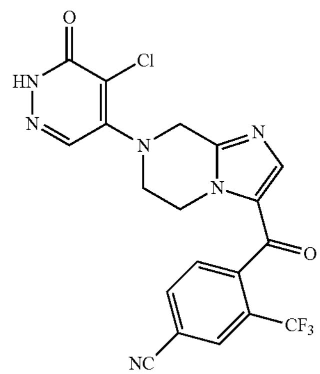

Synthesis Route:

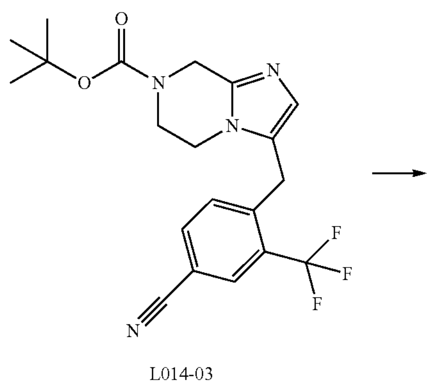

L014-03

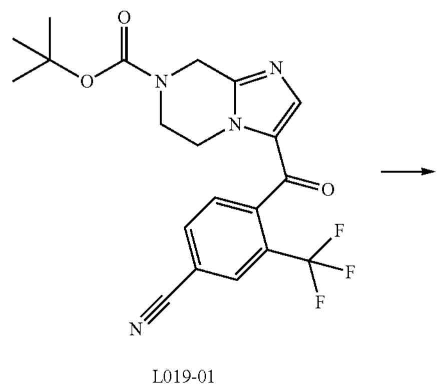

L019-01

-continued

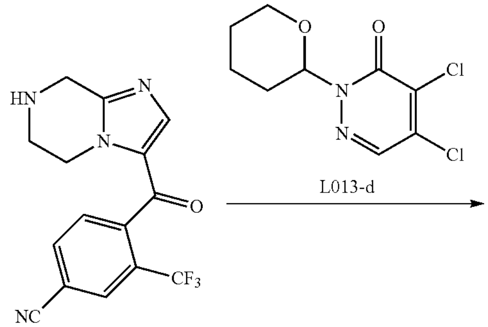

L019-02

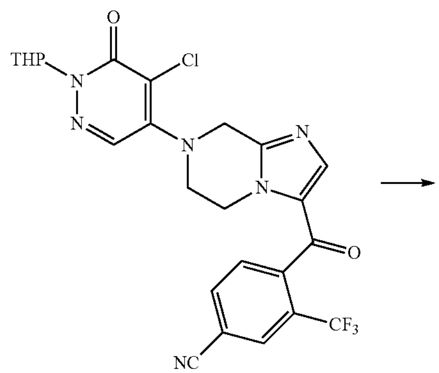

L019-03

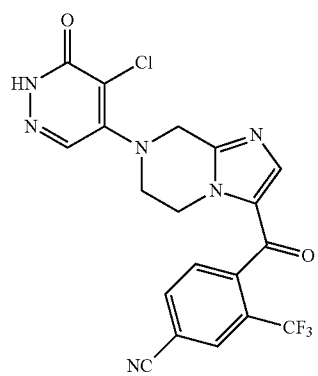

L019

19.1 Preparation of Compound L019-01

Compound L014-03 (2 g, 4.92 mmol), acetic acid (295.52 mg, 4.92 mmol), and ferrous chloride tetrahydrate (97.83 mg, 0.492 mmol) were dissolved in dimethyl sulfoxide (20 mL), and the system was replaced with nitrogen for 3 times, and then the reaction mixture was reacted at 100° C. for 24 hours. After the reaction was completed, the reaction mixture was quenched by adding water (20 mL), and extracted with ethyl acetate (30 mL*3). The organic phases were combined, washed with saturated brine (50 mL), dried over anhydrous sodium sulfate, and filtered. The filtrate was concentrated under reduced pressure, and the crude product was purified by a silica gel chromatography column (petroleum ether/ethyl acetate=100/5) to obtain compound L019-01 (600 mg).

LC-MS=421.10[M+H]$^+$.

19.2 Preparation of Compound L019-02

L019-01 (600 mg, 1.43 mmol) was dissolved in a solution of hydrogen chloride in 1,4-dioxane (4 M, 10 mL) and the reaction mixture was reacted at room temperature for 2 hours. After the reaction was completed, the reaction mixture was filtered to obtain the filter cake as compound L019-02 (500 mg). LC-MS=321.05 [M+1]+.

19.3 Preparation of Compound L019-03

Compound L019-02 (250 mg, 0.78 mmol), L013-d (233 mg, 0.94 mmol), and N,N-diisopropylethylamine (504 mg, 3.9 mmol) were dissolved in dimethylsulfoxide (3 mL). The reaction mixture was reacted at 80° C. for 4 hours, and the reaction was completed. The reaction mixture was quenched by adding water (20 mL), extracted with ethyl acetate (30 mL*3). The organic phases were combined, washed with saturated brine (50 mL), dried over anhydrous sodium sulfate, and filtered. The filtrate was concentrated under reduced pressure, and the crude product was purified by a silica gel chromatography column (dichloromethane/methanol=10/1) to obtain compound L019-03 (200 mg). LC-MS=533.10 [M+H]$^+$.

19.4 Preparation of compound 4-(7-(5-chloro-6-oxo-1,6-dihydropyridazin-4-yl)-5,6,7,8-tetrahydroimidazo[1,2-a]pyrazine-3-carbonyl)-3-(trifluoromethyl)benzonitrile (L019)

L019-03 (200 mg, 0.37 mmol) was dissolved in a solution of hydrogen chloride in 1,4-dioxane (4 M, 10 mL), and the reaction mixture was reacted at room temperature for 2 hours, and the reaction was completed. After the reaction mixture was evaporated to dryness by rotary evaporation to remove the solvent to obtain a crude product, the crude product was purified by preparative high performance liquid chromatography to obtain compound L019.

LC-MS=449.00 [M+H]$^+$;

$^1$H NMR (400 MHz, DMSO-$d_6$) δ 13.06 (s, 1H), 8.50 (s, 1H), 8.31 (d, J=8.0 Hz, 1H), 8.01 (s, 1H), 7.91 (d, J=8.0 Hz, 1H), 7.39 (s, 1H), 4.83 (s, 2H), 4.52 (t, J=5.2 Hz, 2H), 3.92 (t, J=5.2 Hz, 2H).

Comparative Example

Compounds C001 and C002 were the compounds disclosed in patent WO2019055966A2 as TRPC5 inhibitors.

TABLE 10

| Compound number | Compound structure |
|---|---|
| C001 | 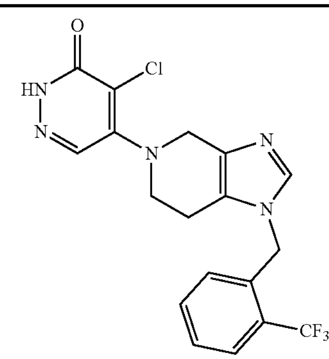 |

TABLE 10-continued

| Compound number | Compound structure |
|---|---|
| C002 | 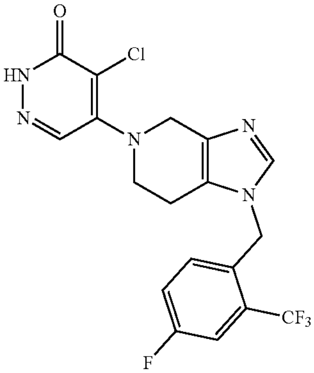 [SMILES: O=c1[nH]ncc(N2CCc3c(ncn3Cc3ccc(F)cc3C(F)(F)F)C2)c1Cl] |

Effect Example 1: Biological Activity Test Assay

TRPC5 is a type of non-selective cation channel with permeability to calcium ions. Therefore, TRPC5 agonist Englerin A (EA) and TRPC5 inhibitor Pico145 were used as positive controls in this experiment. Fluo-4 AM fluorescence dye was used to indirectly reflect the effect of the compound on TRPC5 channel by detecting intracellular $Ca^{21}$ in TRPC5-HEK 293 cells.

1. Cell culture 1.1 Revival of TRPC5-HEK 293 Cells

Revival solution: 100% high glucose DMEM

Selection medium: high glucose DMEM+10% FBS+1% P/S+1% HEPES+Blasticidin (5 μg/mL)+Hygromycine (50 μg/mL)

Induction medium: high glucose DMEM+10% FBS+1% P/S+1% HEPES+Doxycycline (1 μg/mL)

Revival process: A cryopreservation solution containing TRPC5-HEK 293 cells was taken out from the liquid nitrogen tank, and transferred from the ice box to the water bath, and then dissolved in circles to a small piece of ice, and the cryopreservation solution was transferred to the revival solution, and centrifuged at 1000 rpm for 5 minutes, and then the supernatant was discarded, then the residue was transferred to the selection medium, and expanded in a $CO_2$ incubator (5% $CO_2$, humidity of 95%, 37° C.).

1.2 Seeding TRPC5-HEK 293 Cells in Plates 14 hours before the real-time fluorescence experiment, cells were washed with PBS and digested with trypsin-EDTA (TE). Cells were diluted to 200,000 cells/mL with induction medium and seeded onto a 96-well black wall bottom transparent plate coated with poly-D-lysine (PDL) (stock solution of 10 mg/mL, final concentration of 10 μg/mL) at 100 μL/well, i.e., 20,000 cells/well.

2. Preparation of Buffer 500 mL of external solution for detecting TRPC5 calcium signals: 4.0908 g of NaCl, 0.1864 g of KCl, 0.111 g of $CaCl_2$, 0.0476 g of $MgCl_2$, 0.9 g of glucose, 1.1915 g of HEPES (2-[4-(2-hydroxyethyl)piperazin-1-yl]ethanesulfonic acid).

Calcium fluorescent dye: an external solution for detecting TRPC5 calcium signals containing Fluo-4 with a final concentration of 4 μM (containing 0.5% BSA)

3. Preparation of Compounds

Agonist: Englerin A (EA)

Agonist concentration: Since the $EC_{50}$ of TRPC5 activated by the EA was about 0.35 nM, 0.3 nM of EA was used.

Positive inhibitor: Pico145 (HC608)

Positive inhibitor concentration: 100 nM

Compounds to be tested: compound 1-6 and compound 1

Concentration of the compound to be tested: routinely prepared, prepared as a drug solution that was 8 times the final concentration of the test (the final concentrations of the test were: 1 nM, 3 nM, 10 nM, 30 nM, 100 nM, 300 nM, and 1000 nM) with 60 μL per well of the bottom plate.

4. Data Processing

The fluorescence value of the Flipr was tested and subtracted the value of the undyed cell well (i.e., background fluorescence value), and the Graphpad Prism 6.0 software was used for statistics and data processing, and the trajectory map was normalized by removing the baseline and displayed as a ratio. The dose-effect diagram was used to calculate AUC (area under the curve of the curve formed by the calcium flux signal), and the data and the log of the compound concentration were collected. The $IC_{50}$ value was calculated using log[Inhibitor] vs. response Variable slope.

The results are shown in Table 11:

TABLE 11

| Compound number | TRPC5 inhibitory activity, $IC_{50}$ (nM) |
|---|---|
| L001 | 10.75 |
| L002 | 6.52 |
| L007 | 7.37 |
| L009 | 39.43 |
| L013 | 14.56 |
| L014 | 18.23 |
| L015 | 11.5 |
| L019 | 24 |

Effect Example 2: Liver Microsome Half-Life Assay

The in vitro metabolic stability of the compounds of the present disclosure was determined using warm incubation method of liver microsomes in various species. A proper amount of test compound was added to the liver microsomal reaction system (1 mg/mL liver microsomal protein, 25 U/mL glucose-6-phosphate dehydrogenase, 1 mM NADP, 6 mM D-glucose 6-phosphate, 5 mM $MgCl_2$), and the reaction was started by warm incubation in a water bath at 37° C., then 100 μL of the reaction mixture at each time point was added to a centrifuge tube containing 400 μL of internal standard working solution precooled at 0° C. (containing a solution of 200 ng/mL dexamethasone, diclofenac, tolbutamide, and labetalol in acetonitrile), then the reaction was terminated, centrifuged at 4° C. and 10,000 g for 10 min, and the supernatant was taken into LC-MS for analysis and detection to obtain in vitro metabolic half-lives of the test compounds in liver microsomes of various species.

The results are shown in Table 12:

TABLE 12

| Compound number | Liver microsome T½ (min) | | | | |
|---|---|---|---|---|---|
| | Human | Rat | Mouse | Beagle dog | Monkey |
| C001 | 54 | 5 | 60 | 15 | 38 |
| C002 | 90 | 34 | 115 | 102 | 15 |
| L002 | 262 | — | 188 | — | — |
| L001 | 173 | 20 | 154 | — | — |
| L013 | 148 | — | 131 | — | — |
| L014 | 7589 | — | 167 | — | — |
| L015 | 531 | 174 | 78 | — | 247 |

The data in table 12 show that the metabolic stability of the compounds L001 and L002 of the present disclosure in liver microsomes is significantly improved compared with compounds C001 and C002, indicating that the compounds of the present disclosure have better metabolic stability in liver microsomes and have better clinical pharmacokinetic properties.

Effect Example 3: Pharmacokinetic Study of Compounds of the Present Disclosure in Mice In Vivo SPF grade mice (SPF (Beijing) Biotechnology Co., Ltd.) were fasted overnight (free access to water) after adaptive domestication, and given 3 mg/kg or 1 mg/kg the compounds of the present disclosure by gavage and tail vein injection, respectively. Mouse plasma was collected at a specific time point after administration, and the concentration of the compound in plasma was detected by LC-MS/MS (AB SCIEX Qtrap4500). PK parameters of each compound (WinNonlin V5.2, Pharsight) were statistically analyzed and calculated to reflect the pharmacokinetic properties of the compounds of the present disclosure in mice in vivo.

According to the above compounds of the examples of the present disclosure, the results show that the compounds of the present disclosure all have good pharmacokinetic properties in mice in vivo, and can obtain high in-vivo exposure and high oral bioavailability at a low dose, and the oral bioavailability of some compounds is more than 30%, and the oral bioavailability of some compounds is more than 50%. The following Table 13 shows experimental data for representative compounds.

TABLE 13

PK experiments of compounds of the present disclosure in mice in vivo

| Compound | Dose mg/kg | Adminis-tration mode | $C_{max}$ (ng/mL) | $AUC_{last}$ (ng/mL * hr) | Oral bio-availability (%) |
|---|---|---|---|---|---|
| L001 | 1 | p.o. | 84.30 | 84.30 | 80.6 |
| | | i.v. | 225.00 | 225.00 | |
| L002 | 1 | p.o. | 248 | 625 | 43.2 |
| | | i.v. | 833 | 1447 | |
| L014 | 1 | p.o. | 301 | 1066 | 161 |
| | | i.v. | 762 | 663 | |
| L015 | 1 | p.o. | 422 | 1245 | 66.8 |
| | | i.v. | 1110 | 1864 | |

Effect Example 4: Study on the Tissue Distribution of the Compound of the Present Disclosure in CD-1 Mice after Single Intragastric Administration

Experimental Protocol

1.1 Experimental Instruments

TABLE 14

| Name | Model/specification | Manufacturer |
|---|---|---|
| Electronic analytical balance | MS105DU | Mettler-Toledo |
| Electronic scale | YP2001 | Shanghai Yoke Instrument |
| High speed refrigerated centrifuge | STR16 | Thermo Fisher Scientific |
| Ultrafine homogenizer | F6/10-8G | Shanghai Fluke |

1.2 Experimental Preparation

Mice: CD-1 mice, SPF grade, 9, male, weighting 18 to 22 g (source: SPF (Beijing) Biotechnology Co., Ltd., certificate number: 110324200103036532).

Feeding conditions: Ordinary animal house feeding, free access to food and water, 3 animals/cage rearing, 12/12 hours light/dark cycle adjustment (7:00 am/7:00 pm), temperature of 23±1° C.

Dispensing: After accurately weighing compound L015, 20% solutol of the required volume was added thereto first, sonicated for 20 min and stirred for 1.5 hours until no visible particles were visible to the naked eye, and the middle layer of the drug solution was taken for drug administration. 2 parts of the top, middle, and bottom layers of the suspension were taken, and 2 parts of the middle layer of the clarified solution were taken, and 100 μL of each part was accurately aspirated into a 1.5 mL EP tube. Samples were taken before administration, and after sampling, the samples were stored in a −80° C. refrigerator and sent together with the plasma samples for bioanalytical test.

1.3 Dosage Regimen

Animals were randomly divided into 3 groups. Compound L015 was administered at 3 different time points, with 3 animals per group, all males. All mice were given a single intragastric administration with an administration volume of 10 mL/kg. The specific grouping and administration information is as follows:

TABLE 15

| Group | Subject | Number (female/ male) | Time point | Vehicle | Adminis-tration Dose (mg/kg) | Drug Concentration (mg/mL) | Adminis-tration Volume (mL/kg) | Test substance |
|---|---|---|---|---|---|---|---|---|
| 1 | L015 | 0/3 | 0.167 h | 20% | 10 | 1.00 | 10 | L015 |
| 2 | L015 | 0/3 | 1 h | solutol | 10 | 1.00 | 10 | |
| 3 | L015 | 0/3 | 10 h | | 10 | 1.00 | 10 | |

Note: (1) Animal certificate number: 110324200103036532, CD-1 mice, SPF (Beijing) Biotechnology Co., Ltd.; (2) three groups of rats fasted overnight before administration with free access to water; the food was returned 4 hours after administration; (3) the tissue collection time points were determined by referring to the previous PK results of 1, 3, and 10 mpk mice: after oral administration of L015 in mice at a dose of 10 mg/kg, the absorption phase was at 0.167 hours, and the test substance reached peak plasma concentration at 1 hour; it was in the elimination phase at around 10 hours.

1.4 Sample Collection and Preparation

After the administration was completed, the animals in each group were anesthetized by intraperitoneal injection of 1% pentobarbital sodium (the administration volume was 0.06 mL/10 g) 5 minutes before their respective time points, and about 0.3 mL of blood was collected in an anticoagulant EP tube (containing 4 μL of EDTA-$K_2$, 375 mg/mL), which was gently inverted for 3 times and stored in an ice box (no more than 30 minutes), centrifuged at 4° C. for 10 minutes with 3500×g. The supernatant was transferred to a labeled EP tube for bioanalytical test. If it could not be analyzed the same day, it was stored at −80° C. until further testing (be careful not to perform multiple freezing/thawing processes).

After the blood was taken, the abdominal cavity was quickly opened, and the abdominal aorta and vein of the rat were cut. After the blood was drained, the heart, liver, spleen, lung, kidney, and brain of the rat were taken, respectively. After the tissue was taken, the tissue was immediately rinsed with normal saline to remove any residual blood on the surface, blotted dry with filter paper, and the connective tissue was removed and weighed. The homogenization tube was placed in an ice water bath, and the tissue sample homogenate was thoroughly homogenized with a high-speed homogenizer and sent for bioanalytical test. If it could not be analyzed the same day, it was stored at −80° C. until further testing (be careful not to perform multiple thawing/freezing processes).

1.5 Sample Analysis Method 1.5.1 Experimental Instruments

High performance liquid chromatography pump (pump): Exion LC AD Pump, Sciex Company Auto sampler: Exion LC AD Autosampler, Sciex Company Column oven: Exion LC AD Column Oven, Sciex Company Mass spectrometer: AB Sciex Qtrap 4500

High-speed refrigerated centrifuge (centrifuge): Thermo Fisher, ST16R, GG1206085-093

Analytical balance (electronic balance): Mettler Toledo, MS-105D, GG1206363

Micro vortex (vortex): Shanghai Huxi Analysis Instrument Factory, WH-2, GG1206487

1.5.2 Experimental Materials: Mouse Plasma and Tissue 1.5.3 Analyte: L015

1.5.4 Internal Standard: Labetalol 1.5.5 Analytical Method: Liquid Chromatography-Mass Spectrometry (LC-MS)

1.5.6 Mass Spectrometry Conditions 1.5.6.1 Mass Spectrometry Parameters

Ion source: ion electrospray (ESI)

Ionization mode: positive ion mode (Positive)

Detection mode (mode): multi-reaction monitoring (MRM)

Ion spray voltage: 5500

Ion spray temperature (turbo ion spray temp): 550° C.

Curtain gas: 35

Collision cell gas (CAD gas): medium

Nebulizing gas (gas 1): 55.00

Auxiliary gas (gas 2): 55.00

1.5.6.2. Detection of Ion Pairs

TABLE 16

| Compound | Molecular ion (m/z) | Fragment ion (m/z) | Residence time (msec) | Declustering potential (DP) (V) | Collision energy (CE) (eV) |
|---|---|---|---|---|---|
| Labetalol | 329.2 | 294.3 | 15 | 80 | 27 |
| L015 | 442.2 | 406.2 | 30 | 97 | 36 |

1.5.7 Liquid Phase Method

Chromatographic column: Agilent poroshell 120 EC-C18 (4.6×50 mm, 2.7 m)

Mobile Phase A: 0.1% formic acid aqueous solution

Mobile Phase B: a solution of 0.1% formic acid in methanol

Auto sampler wash solution (rinse port wash solution): methanol:water:acetonitrile:isopropanol=1:1:1:1

Column temperature: 40° C.

Flow rate: 0.8 mL/min

Auto sampler temperature (sample tray temp): 15° C.

Injection volume: 10 μL (L015)

Height of presser foot (needle stroke): 49 mm

Auto sampler rinse setting (rinse pump setting): rinse only the injection port

Auto sampler rinse mode (rinse mode): rinse before inhalation

Auto sampler rinse volume for needle (rinse volume): 500 μL

Dip time when rinsing the injection needle (rinse dip time): 2 seconds

Elution Gradient:

TABLE 17

| Time (min) | Module | Function | Value (%) |
|---|---|---|---|
| 0.01 | Pumps | Pump B Conc. | 35 |
| 0.20 | Pumps | Pump B Conc. | 35 |
| 1.20 | Pumps | Pump B Conc. | 98 |
| 2.40 | Pumps | Pump B Conc. | 98 |
| 2.41 | Pumps | Pump B Conc. | 35 |
| 3.00 | System Controller | Stop | 35 |

1.5.8 Pretreatment Method

Sample pretreatment process: 3 μL of working solution was taken, and 57 μL of blank matrix was added into a 1.5 mL centrifuge tube, and then 240 μL of acetonitrile solution containing 200 ng/mL tolbutamide and labetalol mixed with 0.1% formic acid was added to precipitate protein. The mixture was vortexed and mixed for 1 minute, and then centrifuged in a 4° C. centrifuge at 13000 rpm for 15 minutes. 100 μL of supernatant was taken and added to another 96 deep well plate, and 100 μL of methanol:water (1:3, v:v) solution containing 0.1% FA was added. The mixture was mixed with shaking for 1 min, and centrifuged at 3500 rpm for 5 min in a 96-well plate centrifuge and the sample was injected directly.

1.6 Data Analysis

The concentration of L015 in plasma and each tissue at each time point was calculated, and the data were analyzed.

1.7 Experimental Conclusion

20% solutol was used as a vehicle, and after single intragastric administration to male CD-1 mice with L015 at a dose of 10 mg/kg: 0.167 hours after intragastric administration, L015 was widely distributed in the liver (3260 ng/g) and kidney (1467 ng/g) (5.55 times and 2.50 times of the plasma concentration, respectively), wherein L015 was less distributed in brain (0.05 times of the plasma concentration); 1 hour and 10 hours after administration, L015 was still mainly distributed in the liver and kidney (4.53 to 5.05 times and 2.51 to 1.50 times of the plasma concentration, respectively), and the concentrations of L015 in brain were 161 ng/g and 25.9 ng/g, respectively (0.19 to 0.09 times of the plasma concentration, respectively), suggesting that L015 is less distributed in brain at 10 mg/kg. See the FIGURE for details. It shows that the compounds of the present disclosure are mainly distributed in the liver and the target organ (kidney).

What is claimed is:

1. A compound represented by formula I-a, a tautomer thereof, a pharmaceutically acceptable salt thereof, a solvate thereof, or a solvate of the pharmaceutically acceptable salt thereof;

I-a

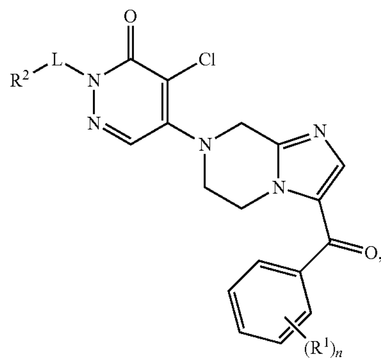

wherein n is 0, 1, 2, 3, or 4;

$R^1$ is independently —CN, halogen, —OH, $C_1$-$C_4$ alkyl, or $C_1$-$C_4$ alkyl substituted by 1, 2, 3, or 4 $R^{1-1}$ groups;

$R^{1-1}$ is independently —CN, halogen, or —OH;

L is a single bond or —$CR^aR^b$—;

$R^a$ is H or $C_1$-$C_3$ alkyl;

$R^b$ is H, halogen, or $C_1$-$C_3$ alkyl;

$R^2$ is

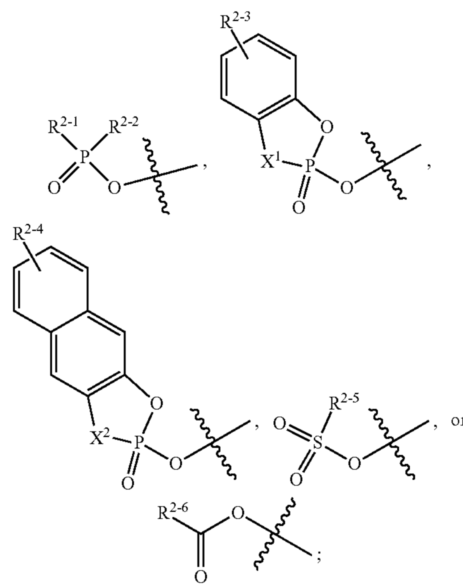

$X^1$ is —O—, —S—, —NH—, —O—$CH_2$—, —S—$CH_2$—, —NH—$CH_2$—, —$CH_2$—, or —$CH_2$—$CH_2$—;

$X^2$ is —O—, —S—, —NH—, —O—$CH_2$—, —S—$CH_2$—, —NH—$CH_2$—, —$CH_2$—, or —$CH_2$—$CH_2$—;

$R^{2-1}$ and $R^{2-2}$ are independently —$OR^{2-1-1}$, —$SR^{2-1-1}$, or —$NR^{2-1-2}R^{2-1-3}$;

$R^{2-1-1}$ is independently H, $C_1$-$C_6$ alkyl, $C_3$-$C_6$ cycloalkyl, $C_1$-$C_6$ alkyl substituted by 1, 2, 3, or 4 $R^{2-1-1-1}$ groups, or $C_3$-$C_6$ cycloalkyl substituted by 1, 2, 3, or 4 $R^{2-1-1-1}$ groups;

$R^{2-1-1-1}$ is independently —CN, F, Cl, Br, I, —OH, —$NH_2$, —COOH, or —$NO_2$;

$R^{2-1-2}$ and $R^{2-1-3}$ are independently H or $C_1$-$C_6$ alkyl;

$R^{2-3}$ is H, F, Cl, Br, I, —CN, —$NO_2$, —$NH_2$, $C_1$-$C_3$ alkyl, or $C_1$-$C_3$ alkoxy;

$R^{2-4}$ is H, F, Cl, Br, I, —CN, —$NO_2$, —$NH_2$, $C_1$-$C_3$ alkyl, or $C_1$-$C_3$ alkoxy;

$R^{2-5}$ is —$OR^{2-5-1}$, —$SR^{2-5-1}$, or —$NR^{2-5-2}R^{2-5-3}$;

$R^{2-5-1}$ is independently H, $C_1$-$C_6$ alkyl, $C_3$-$C_6$ cycloalkyl, $C_1$-$C_6$ alkyl substituted by 1, 2, 3, or 4 $R^{2-5-1-1}$ groups, or $C_3$-$C_6$ cycloalkyl substituted by 1, 2, 3, or 4 $R^{2-5-1-1}$ groups;

$R^{2-5-1-1}$ is independently —CN, F, Cl, Br, I, —OH, —$NH_2$, —COOH, or —$NO_2$;

$R^{2-2}$ and $R^{2-5-3}$ are independently H or $C_1$-$C_6$ alkyl;

$R^{2-6}$ is $C_1$-$C_8$ alkyl, $C_3$-$C_6$ cycloalkyl, —$NR^{2-6-2}R^{2-6-3}$, $C_1$-$C_8$ alkyl substituted by 1, 2, 3, or 4 $R^{2-6-1}$ groups, or $C_3$-$C_6$ cycloalkyl substituted by 1, 2, 3, or 4 $R^{2-6-1}$ groups;

$R^{2-6-1}$ is independently —CN, F, Cl, Br, I, —OH, —$NH_2$, —COOH, or —$NO_2$;

$R^{2-6-2}$ and $R^{2-6-3}$ are independently H or $C_1$-$C_6$ alkyl.

2. The compound represented by formula I-a, the tautomer thereof, the pharmaceutically acceptable salt thereof, the solvate thereof, or the solvate of the pharmaceutically acceptable salt thereof according to claim 1, wherein n is 2;

or, $R^1$ is independently halogen or $C_1$-$C_4$ alkyl substituted by 1, 2, 3 or 4 $R^{1-1}$ groups;

or, $R^{1-1}$ is independently halogen;

or, L is —$CR^aR^b$—;

or, $R^a$ is H;

or, $R^b$ is H;

or, $R^2$ is

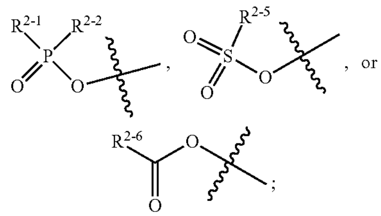

or, $R^{2-1}$ and $R^{2-2}$ are independently —$OR^{2-1-1}$;

or, $R^{2-1-1}$ is H;

or, $R^{2-5}$ is —$OR^{2-5-1}$;

or, $R^{2-5-1}$ is H;

or, $R^{2-6}$ is —$NR^{2-6-2}R^{2-6-3}$ or $C_1$-$C_8$ alkyl substituted by 1, 2, 3, or 4 $R^{2-6-1}$ groups;

or, $R^{2-6-1}$ is —$NH_2$;

or, $R^{2-6-2}$ and $R^{2-6-3}$ are independently methyl or ethyl; or

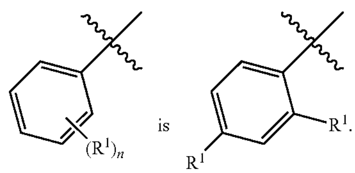

3. The compound represented by formula I-a, the tautomer thereof, the pharmaceutically acceptable salt thereof, the solvate thereof, or the solvate of the pharmaceutically acceptable salt thereof according to claim 2, wherein $R^1$ is independently fluorine or trifluoromethyl;

or, L is —$CH_2$—;

or, $R^2$ is

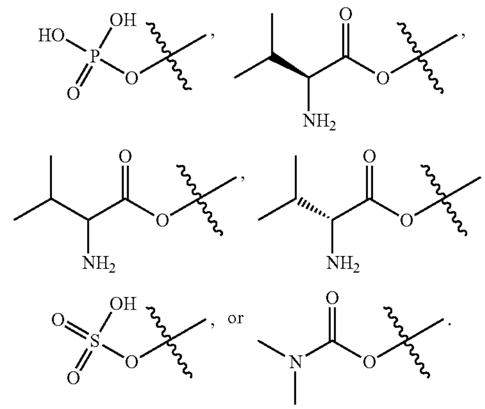

4. The compound represented by formula I-a, the tautomer thereof, the pharmaceutically acceptable salt thereof, the solvate thereof, or the solvate of the pharmaceutically acceptable salt thereof according to claim 3, wherein

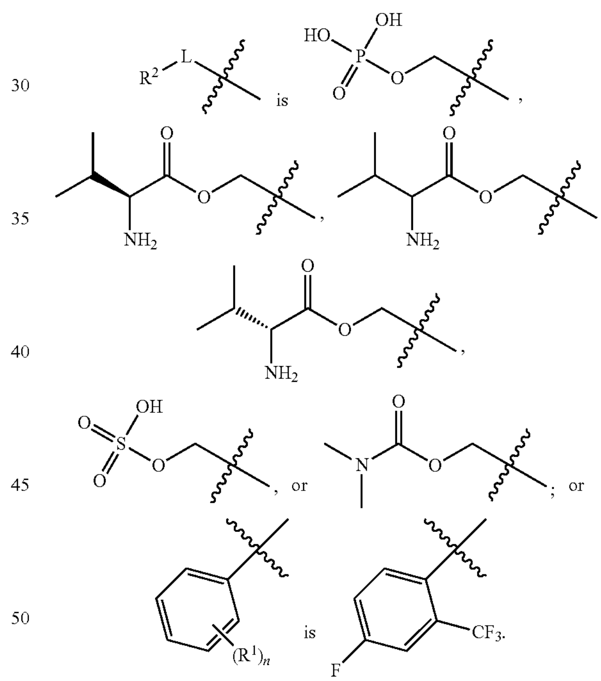

5. The compound represented by formula I-a, the tautomer thereof, the pharmaceutically acceptable salt thereof, the solvate thereof, or the solvate of the pharmaceutically acceptable salt thereof according to claim 1, wherein n is 2;

$R^1$ is independently halogen or $C_1$-$C_4$ alkyl substituted by 1, 2, 3, or 4 $R^{1-1}$ groups;

$R^{1-1}$ is independently halogen;

L is —$CR^aR^b$—;

$R^a$ is H;

$R^b$ is H;

$R^2$ is

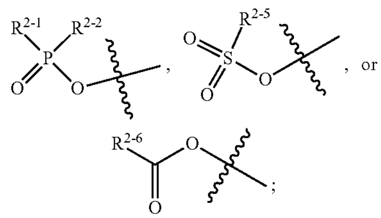

, or ;

$R^{2-1}$ and $R^{2-2}$ are independently —$OR^{2-1-1}$;

$R^{2-1-1}$ is H;

$R^{2-5}$ is —$OR^{2-5-1}$;

$R^{2-5-1}$ is H;

$R^{2-6}$ is —$NR^{2-6-2}R^{2-6-3}$ or $C_1$-$C_8$ alkyl substituted by 1, 2, 3, or 4 $R^{2-6-1}$ groups;

$R^{2-6-1}$ is —$NH_2$;

$R^{2-6-2}$ and $R^{2-6-3}$ are independently methyl or ethyl.

6. The compound represented by formula I-a, the tautomer thereof, the pharmaceutically acceptable salt thereof, the solvate thereof, or the solvate of the pharmaceutically acceptable salt thereof according to claim 1, wherein when $R^1$ is independently halogen, the halogen is fluorine, chlorine, or bromine;

or, when $R^1$ is independently $C_1$-$C_4$ alkyl substituted by 1, 2, 3, or 4 $R^{1-1}$ groups, the $C_1$-$C_4$ alkyl is independently methyl, ethyl, n-propyl, isopropyl, n-butyl, isobutyl, sec-butyl, or tert-butyl;

or, when $R^1$ is independently $C_1$-$C_4$ alkyl substituted by 1, 2, 3, or 4 $R^{1-1}$ groups, the $R^{1-1}$ is independently halogen;

or, when $R^1$ is independently $C_1$-$C_4$ alkyl substituted by 1, 2, 3, or 4 $R^{1-1}$ groups, the number of $R^{1-1}$ groups is 2 or 3;

or, when $R^{2-6}$ is $C_1$-$C_8$ alkyl substituted by 1, 2, 3, or 4 $R^{2-6-1}$ groups, the $C_1$-$C_8$ alkyl is $C_1$-$C_4$ alkyl;

or, when $R^{2-6}$ is $C_1$-$C_8$ alkyl substituted by 1, 2, 3, or 4 $R^{2-6-1}$ groups, the $R^{2-6-1}$ is independently —$NH_2$;

or, when $R^{2-6}$ is $C_1$-$C_8$ alkyl substituted by 1, 2, 3, or 4 $R^{2-6-1}$ groups, the number of $R^{2-6-1}$ groups is 1;

or, when $R^{2-6-2}$ and $R^{2-6-3}$ are independently $C_1$-$C_6$ alkyl, the $C_1$-$C_6$ alkyl is $C_1$-$C_3$ alkyl.

7. The compound represented by formula I-a, the tautomer thereof, the pharmaceutically acceptable salt thereof, the solvate thereof, or the solvate of the pharmaceutically acceptable salt thereof according to claim 6, wherein when $R^1$ is independently halogen, the halogen is fluorine;

or, when $R^1$ is independently $C_1$-$C_4$ alkyl substituted by 1, 2, 3, or 4 $R^{1-1}$ groups, the $C_1$-$C_4$ alkyl is independently methyl;

or, when $R^1$ is independently $C_1$-$C_4$ alkyl substituted by 1, 2, 3, or 4 $R^{1-1}$ groups, the $R^{1-1}$ is independently fluorine;

or, when $R^1$ is independently $C_1$-$C_4$ alkyl substituted by 1, 2, 3, or 4 $R^{1-1}$ groups, the number of $R^{1-1}$ groups is 3;

or, when $R^{2-6}$ is $C_1$-$C_8$ alkyl substituted by 1, 2, 3, or 4 $R^{2-6-1}$ groups, the $C_1$-$C_8$ alkyl is isobutyl;

or, when $R^{2-6-2}$ and $R^{2-6-3}$ are independently $C_1$-$C_6$ alkyl, the $C_1$-$C_6$ alkyl is methyl.

8. The compound represented by formula I-a, the tautomer thereof, the pharmaceutically acceptable salt thereof, the solvate thereof, or the solvate of the pharmaceutically acceptable salt thereof according to claim 7, wherein when $R^1$ is independently $C_1$-$C_4$ alkyl substituted by 1, 2, 3, or 4

$R^{1-1}$ groups, the $C_1$-$C_4$ alkyl substituted by 1, 2, 3, or 4 $R^{1-1}$ groups is difluoromethyl or trifluoromethyl;

or, when $R^{2-6}$ is $C_1$-$C_8$ alkyl substituted by 1, 2, 3, or 4 $R^{2-6-1}$ groups, the $R^{2-6}$ is

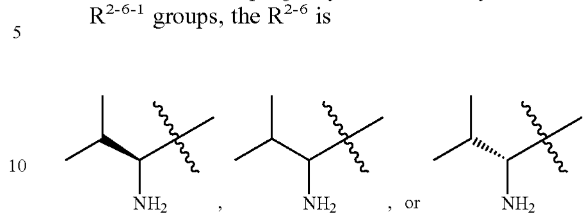

, , or ;

or, when $R^{2-6}$ is —$NR^{2-6-2}R^{2-6-3}$, the $R^{2-6}$ is

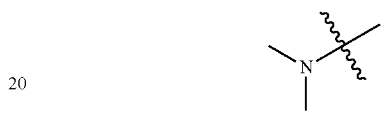

.

9. The compound represented by formula I-a, the tautomer thereof, the pharmaceutically acceptable salt thereof, the solvate thereof, or the solvate of the pharmaceutically acceptable salt thereof according to claim 1, wherein

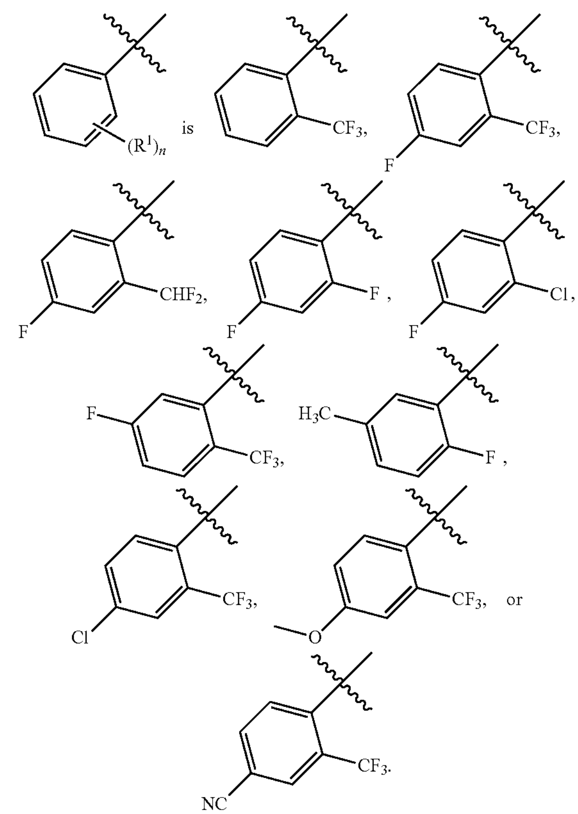

is , , , , , , , , or .

10. The compound represented by formula I-a, the tautomer thereof, the pharmaceutically acceptable salt thereof, the solvate thereof, or the solvate of the pharmaceutically acceptable salt thereof according to claim 1, wherein the compound represented by formula I-b has a structure as shown in formula I-b:

I-b

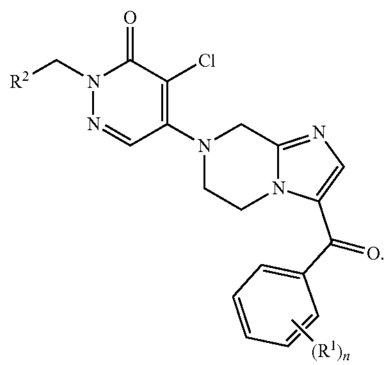

11. The compound represented by formula I-a, the tautomer thereof, the pharmaceutically acceptable salt thereof, the solvate thereof, or the solvate of the pharmaceutically acceptable salt thereof according to claim 1, wherein the compound represented by formula I-a is selected from the following compounds:

1

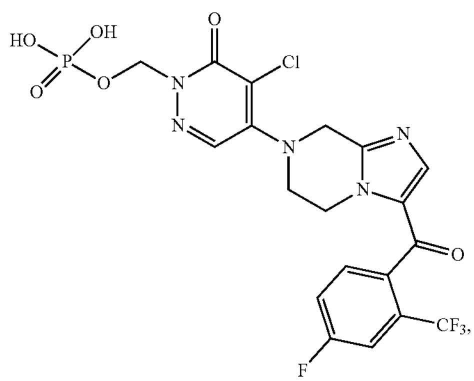

2

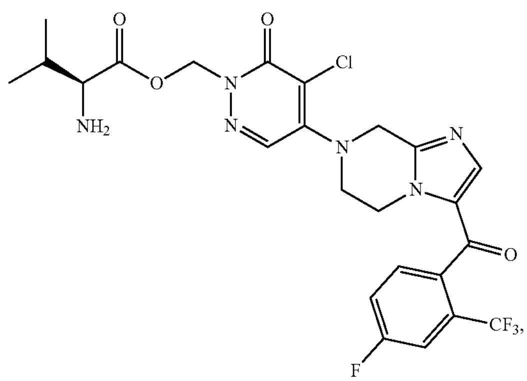

-continued

3

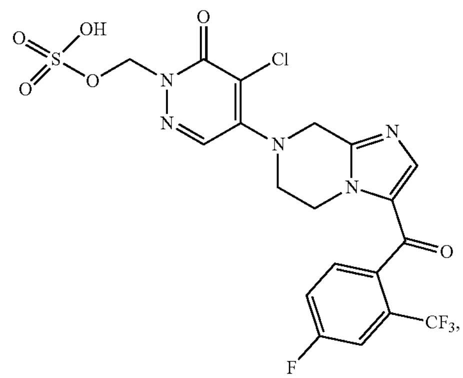

4

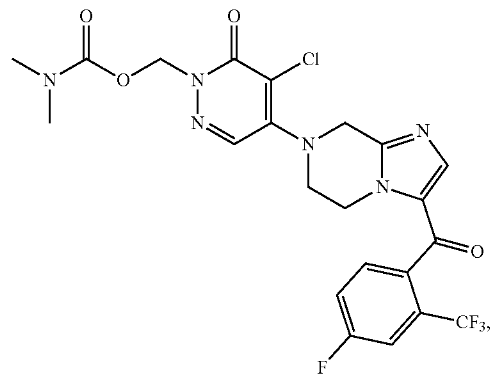

5

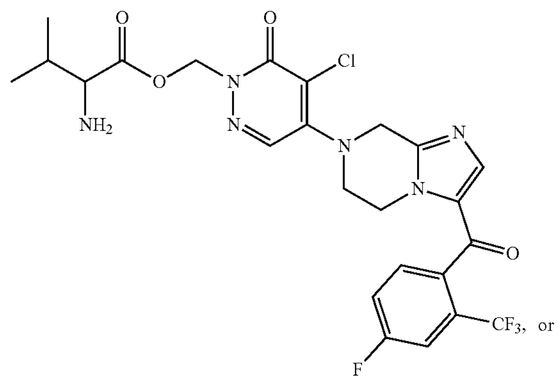

or

6

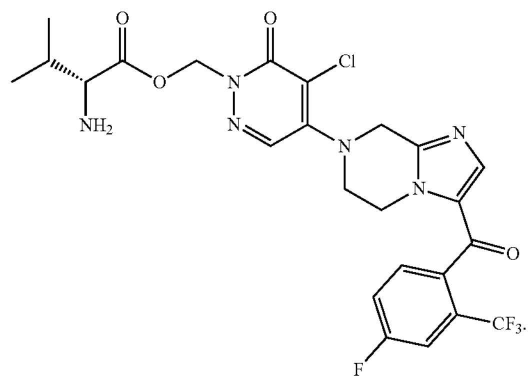

12. A preparation method for a compound represented by formula I-b, which is method 1 or method 2:

the method 1 comprises the following step: in a solvent, in the presence of an acid, carrying out a deprotection reaction on compound I-c to obtain the compound represented by formula I-b;

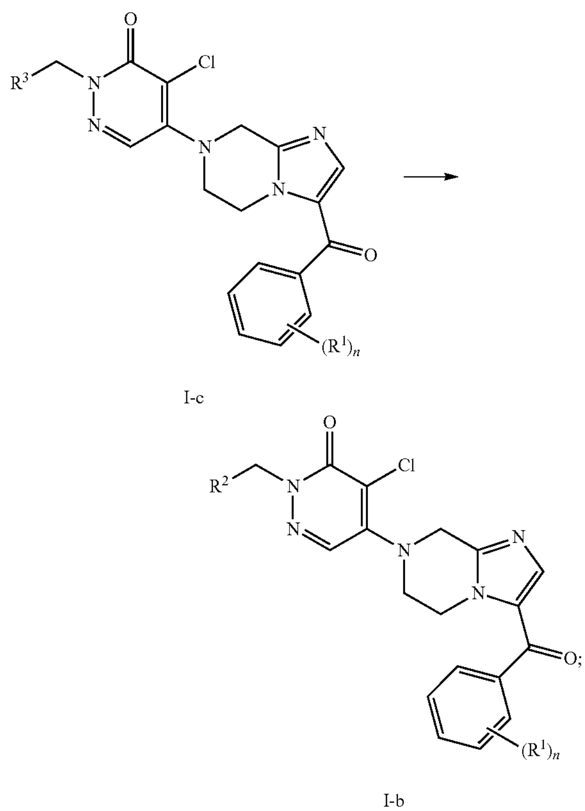

I-c

I-b wherein $R^2$ is

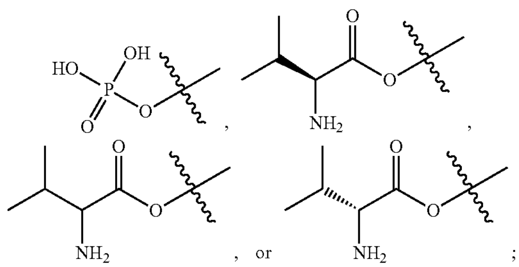

, , , or ;

$R^3$ is

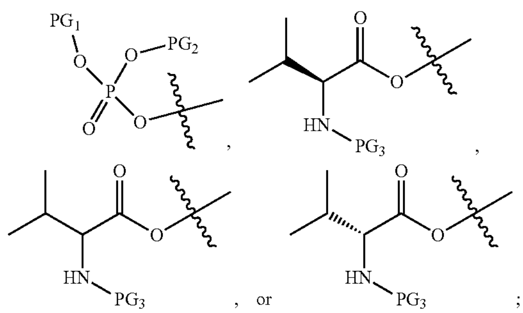

, , , or ;

$PG_1$ and $PG_2$ are hydroxy protective groups; $PG_3$ is an amino protective group; $R^1$ and n are as defined in claim 1;

the method 2 comprises the following step: in a solvent, carrying out a substitution reaction between compound III-1 with chlorosulfonic acid or dimethylcarbamoyl chloride to obtain the compound represented by formula I-b;

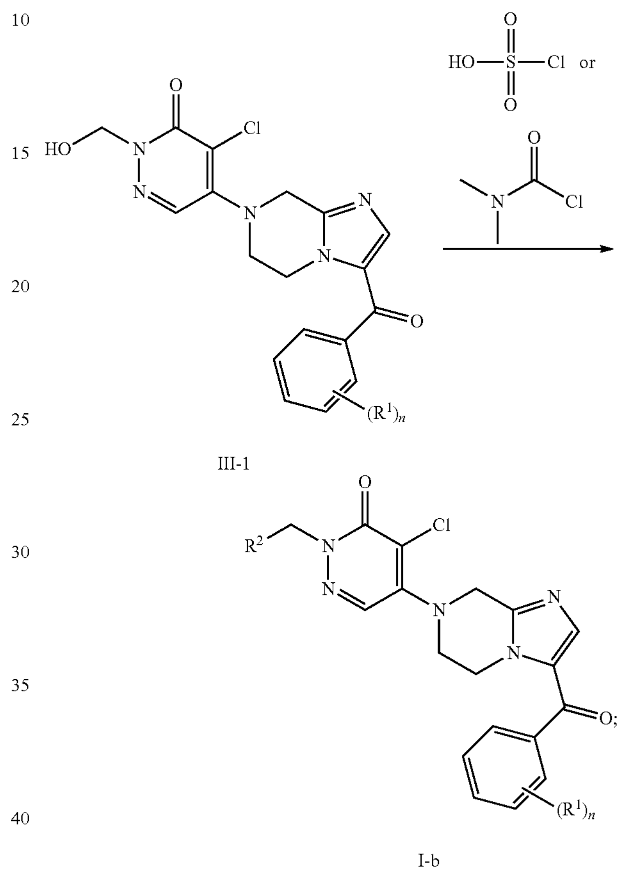

III-1

I-b wherein $R^2$ is

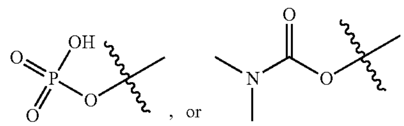

, or ;

$R^1$ and n are as defined in claim 1.

13. The preparation method for the compound represented by formula I-b according to claim 12, wherein in method 1, both $PG_1$ and $PG_2$ are t-Bu;

or, in method 1, $PG_3$ is Boc;

or, in method 1, the acid is trifluoroacetic acid or a 1,4-dioxane solution of hydrogen chloride;

or, in method 1, the solvent is dichloromethane and/or ethyl acetate;

or, in method 2, when $R^2$ is

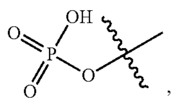

the solvent is acetonitrile;

or, in method 2, when $R^2$ is

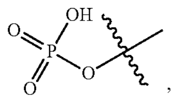

the molar ratio of the chlorosulfonic acid to the compound III-1 is (3 to 6):1;

or, in method 2, when $R^2$ is

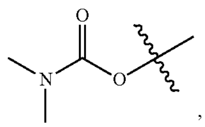 [SMILES: *OC(=O)N(C)C]

the solvent is tetrahydrofuran;

or, in method 2, when $R^2$ is

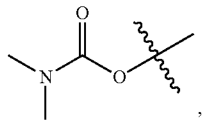 [SMILES: *OC(=O)N(C)C]

the molar ratio of the dimethylcarbamoyl chloride to the compound III-1 is (1 to 2):1.

14. A compound represented by formula I-c-1, I-c-2, or III-1:

I-c-1

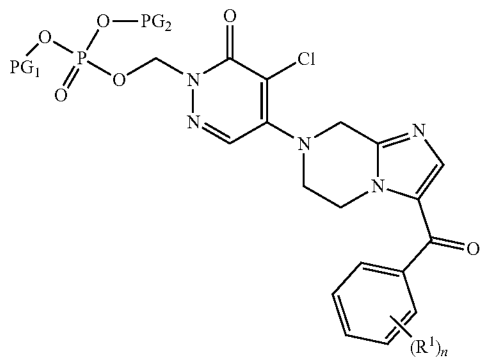

-continued

I-c-2

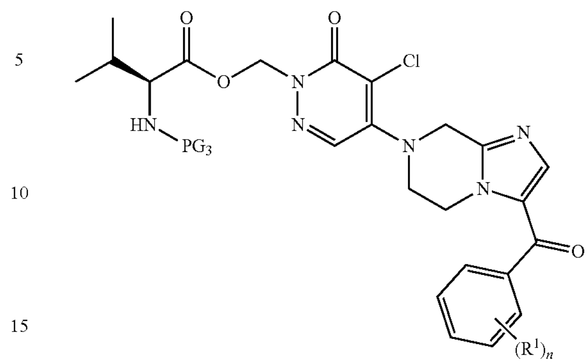

III-1

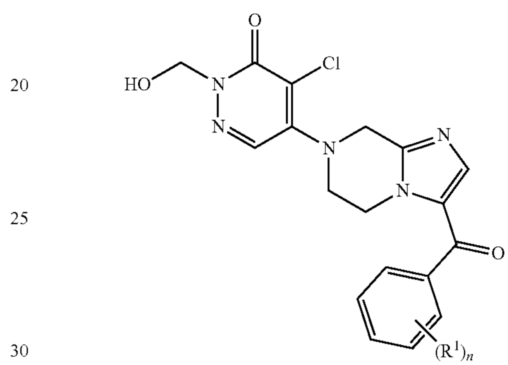

wherein $R^1$ is independently —CN, halogen, —OH, $C_1$-$C_4$ alkyl, or $C_1$-$C_4$ alkyl substituted by 1, 2, 3, or 4 $R^{1-1}$ groups;

n is 0, 1, 2, 3, or 4;

$PG_1$ and $PG_2$ are hydroxy protective groups;

$PG_3$ is an amino protective group.

15. The compound according to claim 14, wherein the compound represented by formula I-c-1 is the following compound:

1-7

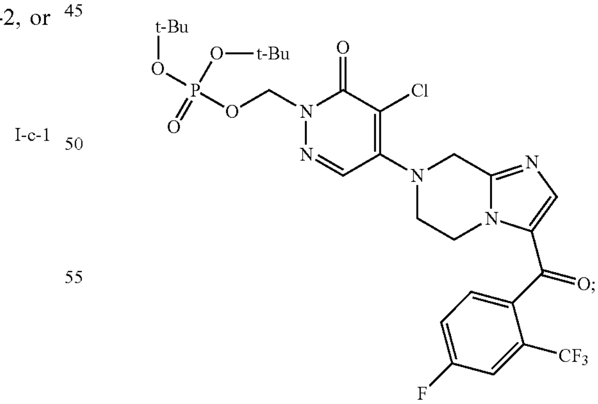

or, the compound represented by formula I-c-2 is the following compound:

2-2

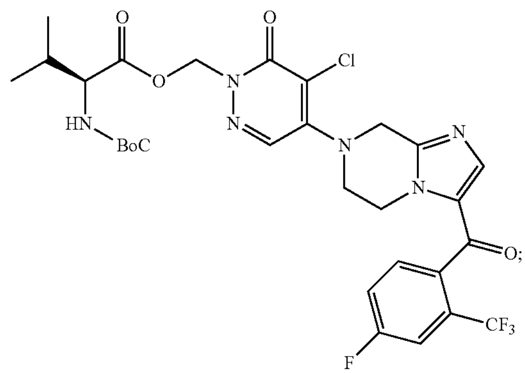

or, the compound represented by formula III-1 is the following compound:

3-1

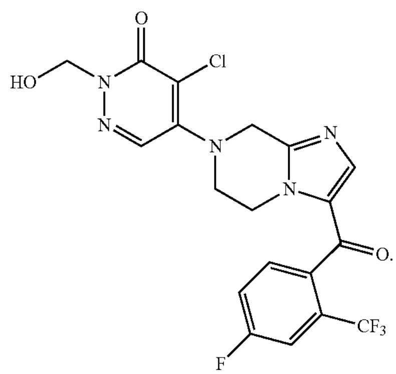

16. A pharmaceutical composition, wherein the pharmaceutical composition comprises the compound represented by formula I-a, the tautomer thereof, the pharmaceutically acceptable salt thereof, the solvate thereof, or the solvate of the pharmaceutically acceptable salt thereof according to claim 1 and a pharmaceutical excipient.

17. A method for inhibiting TRPC5 in a subject in need thereof, comprising: administering the compound represented by formula I-a, the tautomer thereof, the pharmaceutically acceptable salt thereof, the solvate thereof, or the solvate of the pharmaceutically acceptable salt thereof according to claim 1 to the subject.

18. A method for treating and/or preventing a disease mediated by TRPC5, wherein the method comprises administering a therapeutically effective amount of the compound represented by formula I-a, the tautomer thereof, the pharmaceutically acceptable salt thereof, the solvate thereof, or the solvate of the pharmaceutically acceptable salt thereof according to claim 1 to a subject in need thereof.

19. The method for treating and/or preventing the disease mediated by TRPC5 according to claim 18, wherein the disease mediated by TRPC5 is a psychiatric disorder, a neurological disorder, a neurodegenerative disorder, or nephropathy.

20. The method for treating and/or preventing the disease mediated by TRPC5 according to claim 19, wherein the psychiatric disorder, neurological disorder, or neurodegenerative disorder is selected from: a disease associated with dysregulated emotional processing, a disorder associated with anxiety and fear, a memory disorder, a disorder associated with impaired impulse control and addiction, Alzheimer's disease, Parkinson's disease, Huntington's disease, amyotrophic lateral sclerosis, epilepsy, and other brain disorders caused by trauma or other injury;

the nephropathy is focal segmental glomerulosclerosis, minimal change nephropathy, or diabetic nephropathy.

21. The method for treating and/or preventing the disease mediated by TRPC5 according to claim 20, wherein the disease associated with dysregulated emotional processing is borderline personality disorder or depression;

or, the disorder associated with anxiety and fear is post-traumatic stress disorder, panic disorder, agoraphobia, social phobia, generalized anxiety disorder, panic disorder, social anxiety disorder, obsessive-compulsive disorder, or separation anxiety;

or, the memory disorder is Alzheimer's disease, amnesia, aphasia, brain injury, brain tumor, chronic fatigue syndrome, Creutzfeldt-Jakob disease, dissociative amnesia, fugue amnesia, Huntington's disease, learning disorder, sleeping disorder, multiple personality disorder, pain, post-traumatic stress disorder, schizophrenia, sports injury, stroke, or Wernicke-Korsakoff Syndrome.

22. The method for treating and/or preventing the disease mediated by TRPC5 according to claim 20, wherein the disease associated with dysregulated emotional processing is major depression, major depressive disorder, psychiatric depression, dysthymia, postpartum depression, or bipolar disorder.

* * * * *